(12) United States Patent
Friary et al.

(10) Patent No.: US 7,645,774 B2
(45) Date of Patent: Jan. 12, 2010

(54) CANNABINOID RECEPTOR LIGANDS

(75) Inventors: Richard J. Friary, Florence, MT (US); Joseph A. Kozlowski, Princeton, NJ (US); Bandarpalle B. Shankar, Branchburg, NJ (US); Michael K. C. Wong, North Brunswick, NJ (US); Guowei Zhou, Livingston, NJ (US); Brian J. Lavey, Chatham, NJ (US); Neng-Yang Shih, North Caldwell, NJ (US); Ling Tong, Warren, NJ (US); Lei Chen, Roselle Park, NJ (US); Youheng Shu, Blue Bell, PA (US)

(73) Assignee: Schering Corporation, Kenilworth, NJ (US)

(*) Notice: Subject to any disclaimer, the term of this patent is extended or adjusted under 35 U.S.C. 154(b) by 506 days.

(21) Appl. No.: 11/197,979

(22) Filed: Aug. 5, 2005

(65) Prior Publication Data
US 2005/0282861 A1    Dec. 22, 2005

Related U.S. Application Data

(62) Division of application No. 10/292,778, filed on Nov. 12, 2002, now Pat. No. 7,071,213.

(60) Provisional application No. 60/332,911, filed on Nov. 14, 2001.

(51) Int. Cl.
*A61K 31/445* (2006.01)
*C07D 211/26* (2006.01)

(52) U.S. Cl. .................. 514/317; 514/327; 546/192; 546/216; 546/226; 546/229

(58) Field of Classification Search ................ 514/317, 514/327; 546/192, 216, 226, 229
See application file for complete search history.

(56) References Cited

U.S. PATENT DOCUMENTS

| | | | |
|---|---|---|---|
| 4,466,965 A | 8/1984 | Stout et al. | |
| 4,567,184 A | 1/1986 | Musser et al. | |
| 5,332,820 A | 7/1994 | Duncia et al. | |
| 5,338,753 A | 8/1994 | Burstein et al. | |
| 5,462,960 A | 10/1995 | Barth et al. | |
| 5,486,525 A | 1/1996 | Summers, Jr. et al. | |
| 5,532,237 A | 7/1996 | Gallant et al. | |
| 5,866,589 A | 2/1999 | Romero et al. | |
| 5,925,768 A | 7/1999 | Barth et al. | |
| 5,948,777 A | 9/1999 | Bender et al. | |
| 5,990,170 A | 11/1999 | Della Valle et al. | |
| 6,013,648 A | 1/2000 | Rinaldi et al. | |
| 6,017,919 A | 1/2000 | Inaba et al. | |
| 6,506,901 B2* | 1/2003 | Steffan et al. ............ 546/192 |
| 7,067,539 B2 | 6/2006 | Kozlowski et al. | |
| 7,297,796 B2* | 11/2007 | Dolle et al. ............ 546/205 |

FOREIGN PATENT DOCUMENTS

| | | |
|---|---|---|
| DE | 19533644 | 9/1995 |
| EP | 0181568 | 5/1986 |
| EP | 0401030 | 12/1990 |
| EP | 0407217 | 1/1991 |
| EP | 1031571 | 8/2000 |
| EP | 1283039 | 2/2003 |
| EP | 1314733 | 5/2003 |
| JP | 06072929 | 3/1994 |
| WO | WO 93/21158 | 10/1993 |
| WO | WO 96/23783 | 8/1996 |
| WO | WO 97/03953 | 2/1997 |
| WO | WO 98/10763 | 3/1998 |
| WO | WO 98/31227 | 7/1998 |
| WO | WO 98/33769 | 8/1998 |
| WO | WO 98/41519 | 9/1998 |
| WO | WO 99/26612 | 6/1999 |
| WO | WO 99/36393 | 7/1999 |
| WO | WO 99/50245 | 10/1999 |
| WO | WO 00/06146 | 2/2000 |
| WO | WO 01/37826 | 5/2001 |
| WO | WO 01/44172 | 6/2001 |
| WO | WO 01/44239 | 6/2001 |
| WO | WO 01/64642 | 9/2001 |
| WO | WO 01/70753 | 9/2001 |
| WO | WO 01/74762 | 10/2001 |
| WO | WO 01/83460 | 11/2001 |
| WO | WO 02/062750 | 8/2002 |
| WO | WO 03/042174 | 5/2003 |

OTHER PUBLICATIONS

George et al. "dihydroisoindoles . . . " CA113:58970 (1990).*
Hasegawa et al. "Preparation 2-1-benzyl . . . " CA 117:69851 (1992).*
Islam et al. "preparation of aryl sulfonamide . . . " CA 127:95085 (1997).*
Takatani et al. "Fused imidazopyridine . . . " CA 128:3692 (1997).*
Bergeron et al. "Methods and bicyclic . . . " CA130:33012 (1998).*
Gong et al. "Arylcarbamoylalkylpiperazines . . . " CA 130:196670 (1999).*
Mantell et al. "Preparation of 2-aminocarbonyl-9H . . . " CA 136:37902 (2001).*

(Continued)

*Primary Examiner*—Celia Chang
(74) *Attorney, Agent, or Firm*—Keith D. MacMillan; Serena Farquharson Torres; Palaiyur S. Kalyanaraman

(57) ABSTRACT

There are disclosed compounds of the formula I:

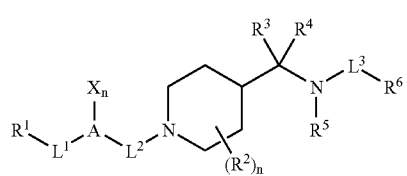

or a pharmaceutically acceptable salt of the compound, which exhibit anti-inflammatory and immunomodulatory activity. Also disclosed are pharmaceutical compositions containing said compounds.

30 Claims, No Drawings

OTHER PUBLICATIONS

Chemcats 203081445, RN 838884-31-4 (2008).*
Greene "Protective groups in Organic synthesis" p. 218-220, 224, 251 (1982).*
Curtin et al., "Discovery and Evaluation of a Series of 3-Acylindole Imidazopyridine Platelet-Activating Factor Antagonists"; 41(I) *J. Med. Chem.* 74-95 (1998).
Hartman et al., "4-Substituted Thiophene—and Furan—2-sulfonamides as topical carbonic anhydrase inhibitors" 35(21) *J. Med. Chem.* 203-208 1983.
Hartman et al., "Synthesis and derivatization of 4-(arylsulfonyl) thiophene—and-furan-2 sulfonamides", 27(2) *J. Heterocycl. Chem.* 127-34 1990.
Cozzi et al., "New N-(2-ethoxyethyl)-N-(4-phenoxybenzyl) dichloroacetamides as potent antiamoebic agents", 18(3) *Eur. J. Med. Chem.* 203-208 (1983).
U.S. Appl. No. 10/464,174 (AL01561K) for "Cannabinoid Receptor Agonists", filed Jun. 17, 2003.
Pertwee, T. G., "Pharmacology of Cannabinoid Receptor Ligands", *Curr. Med. Chem.* 6(8) (1999).
Greene et al. "Protective Groups in Organic Synthesis" 1981, Wiley, New York.
Higuchi T. and Stella V., "Pro-drugs as Novel Drug Delivery Systems" (1975) 14 of the A. C.S. Symposium Series.
Roche, Edward B., "Bio reversible Carriers in Drug Design", ed., *American Pharmaceutical Association and Pergamon Press* (1987).
Berge et al., "Pharmaceutical Salts", *Journal of Pharmaceutical Sciences* (1977) 66(1) 1-19.
Gould P., "Salt Selection for Basic Drugs", *International J. of Pharmaceutics* (1986) 33 201-217.
Anderson et al., "The Practice of Medicinal Chemistry" (1996), *Academic Press*. New York.

Swain et al., "Dihydroergot analogs 1-(3-Indolylmethyl) piperidinecarboxamides". *Chemical Abstract* 52:21120 (1958).
Howlett et al., "Cannabinoid receptor agonists and antagonists", *Chemical Abstract* 124:219022 (1996).
Sacerdote et al, "In vivo and in vitro treatment with the synthetic cannabinoid CP55, 940 decreases the in vitro migration of macrophages in the rat: involvement of both Cb1 and CB2 receptors". *Chemical Abstract* 134:13272 (2000).
Sasaki et al., "Nitrogen containing aromatic heterocyclic compounds and pharmaceuticals for treatment of pollakiuria, urinary incontinence, and inflammation", *Chemical Abstract* 135:14337(2001).
Sato et al, Preparation of sulfonylaminomethylpiperidinylethylamines for antiobesity, antidiabetics, and antihypertensives, *Chemical Abstract* 135:81247 (2001).
Lutz B., "Molecular biology of cannabinoid receptors". *Chemical Abstract* 138:526698 (2002).
Boss et al., "Preparation of substituted 3- and 4- (aminomethyl) piperidines for use as β-secretase inhibitors in the treatment of Alzheimer's disease", Chemical Abstract 140:77034 (2004).
Romero et al., Anti-AIDS heteroaryl-substituted piperazines. aminopiperidines, and piperidines, *Chemical Abstract* 125:142777 (1996).
Shiota et al., "Preparation of cyclic amine derivatives as remedies or preventives for diseases in association with chemokines or chemokine receptors", *Chemical Abstract* 134:5154 (2000).
Nazare et al., "Preparation of indole-2-carboxamides as factor Xa inhibitors", *Chemical Abstract* 139:6766 (2000).
Hickey et al, "Preparation of novel amino nitriles useful as reversible inhibitors of cysteine proteases", *Chemical Abstract* 138:24952 (2002).

* cited by examiner

CANNABINOID RECEPTOR LIGANDS

This application is a divisional of U.S. application Ser. No. 10/292,778, filed Nov. 12, 2002, and claims the benefit of U.S. Provisional Application Ser. No. 60/332,911 filed Nov. 14, 2001.

BACKGROUND

The present invention relates to cannabinoid receptor ligands and, more particularly, to compounds that bind to cannabinoid ($CB_2$) receptors. Compounds according to the present invention generally exhibit anti-inflammatory and immunomodulatory activity and are useful in treating conditions characterized by inflammation and immunomodulatory irregularities. Examples of conditions which may be treated include, but are not limited to, rheumatoid arthritis, asthma, allergy, psoriasis, Crohn's disease, systemic lupus erythematosus, multiple sclerosis, diabetes, cancer, glaucoma, osteoporosis, renal ischemia, cerebral stroke, cerebral ischemia, and nephritis. The invention also relates to pharmaceutical compositions containing said compounds.

Cannabinoid receptors belong to the superfamily of G-protein coupled receptors. They are classified into the predominantly neuronal CB1 receptors and the predominantly peripheral CB2 receptors. While the effects of CB1 receptors are principally associated with the central nervous system, CB2 receptors are believed to have peripheral effects related to bronchial constriction, immunomodulation and inflammation. As such, a selective CB2 receptor binding agent is expected to have therapeutic utility in the control of diseases associated with inflammation, immunomodulation and bronchial constriction such as rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (see, e.g., R. G. Pertwee, Curr. Med. Chem. 6(8), (1999), 635).

Various compounds have reportedly been developed which interact with $CB_2$ receptors and/or which have, inter alia, anti-inflammatory activity associated with cannabinoid receptors. See, e.g., U.S. Pat. Nos. 5,338,753, 5,462,960, 5,532,237, 5,925,768, 5,948,777, 5,990,170, 6,013,648 and 6,017,919.

SUMMARY OF THE INVENTION

In its many embodiments, the present invention provides compounds of formula I:

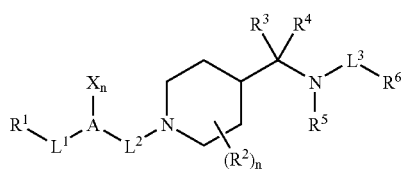

I or a pharmaceutically acceptable salt or solvate of said compound, wherein:

$L^1$ is a covalent bond, —$CH_2$—, —C(O)—, —C(O)O—, $S(O_2)$—, —S(O)—, —S—, —O—, —NH—, or —N($R^7$)—;

$L^2$ is —$CH_2$—, —C(H)(alkyl)-, —C(alkyl)$_2$—, —C(O)—, —SO—, —S($O_2$,)—, —C(=N$R^7$)—, —C(=N—CN)— or —C(=N—O$R^7$);

$L^3$ is a covalent bond, —C(O)— or —S($O_2$)—;

$R^1$ is selected from the group consisting of H, halogen, alkyl, haloalkyl, cycloalkyl, cycloalkylalkyl, heterocyclylalkyl, —NH$R^7$, —N($R^7$)$_2$, —C(O)$R^7$, —C(O)O$R^7$, —S($O_2$)$R^7$, —Si(alkyl)$_n$(aryl)$_{3-n}$, aryl and heteroaryl, wherein each of said aryl or heteroaryl can be unsubstituted or optionally substituted with one to five moieties which can be the same or different and are independently selected from the group consisting of halogen, alkyl, cycloalkyl, cycloalkylalkyl, haloalkyl, haloalkoxy, alkoxy, —N($R^7$)$_2$, —C(O)O$R^7$, —C(O)N($R^7$)$_2$, —NC(O)$R^7$, —NC(O)O$R^7$, —NC(O)N($R^7$)$_2$, —NO$_2$, —CN, —S($O_2$)$R^7$, —S($O_2$)N($R^7$)$_2$, —NC(=N—CN)NH$R^7$, and OH, with the proviso that:
 a) when $R^1$ is halogen, $L^1$ is a covalent bond;
 b) when $R^1$ is —NH$R^7$ or —N($R^7$)$_2$, $L^1$ is a covalent bond, —$CH_2$—, —C(O)—, —S($O_2$)— or —SO—;
 c) when $R^1$ is —C(O)$R^7$ or —C(O)O$R^7$, $L^1$ is a covalent bond, —$CH_2$—, —NH— or —N(alkyl)-; and
 d) when $R^1$ is —S($O_2$)$R^7$ or —C(O)O$R^7$, $L^1$ is a covalent bond, —$CH_2$—, —NH— or —N(alkyl)-;

$R^2$ is H, —OH, halogen, —N($R^7$)$_2$, —CF$_3$, alkoxy, alkyl, haloalkyl, cycloalkyl or cycloalkylalkyl;

$R^3$ and $R^4$ are the same or different, and are independently H or alkyl, or $R^3$ and $R^4$ taken together form a carbonyl group, i.e. C(=O);

$R^5$ is H or alkyl;

$R^6$ is selected from the group consisting of H, alkyl, haloalkyl, cycloalkyl, NH$R^7$, N($R^7$)$_2$, aryl and heteroaryl, wherein each of said aryl and heteroaryl can be unsubstituted or optionally substituted with one to five moieties which moieties can be the same or different and are independently selected from the group consisting of halogen, alkyl, cycloalkyl, haloalkyl, haloalkoxy, alkoxy and OH;

$R^7$ is selected from H, alkyl, haloalkyl, cycloalkyl, heterocyclylalkyl, aryl and heteroaryl, wherein each of said aryl and heteroaryl can be unsubstituted or optionally substituted with one to five moieties which moieties can be the same or different and are independently selected from the group consisting of halogen, alkyl, cycloalkyl, haloalkyl, haloalkoxy, alkoxy and/or OH;

A is selected from phenyl, naphthyl, pyridyl, thienyl, thiazolyl, and indolyl, quinolyl, isoquinolyl, pyrazinyl, pyridazinyl, furanyl, pyrrolyl, pyrimidyl, quinazolinyl, quinoxalinyl, phthalazinyl, benzofuranyl, benzothienyl;

X is independently selected from the group consisting of H, halogen, alkyl, cycloalkyl, haloalkyl, hydroxy, alkoxy, alkoxycarbonyl, haloalkoxy, —N($R^7$)$_2$, —N($R^7$)(C(O)$R^7$), —N($R^7$)(C(O)O$R^7$), —NO$_2$ and CN, and when A is selected from the group consisting of pyridyl, thienyl, thiazolyl, indolyl, quinolyl, isoquinolyl, pyrazinyl, pyridazinyl, pyrrolyl, pyrimidyl, cinnolinyl, quinazolinyl, quinoxalinyl, phthalazinyl, and benzothienyl, X can be oxide; and n is 0-3, with the proviso that (i) the two $R^7$ moieties in —N($R^7$)$_2$ can be the same or different and are independently selected, and (ii) the moiety —N($R^5$)-$L^3$-$R^6$ can optionally form a ring system.

The compounds of the present invention can be useful as cannabinoid receptor ligands. The compounds can have anti-inflammatory activity and/or immunomodulatory activity and can be useful in the treatment of various medical conditions including, e.g., cutaneous T-cell lymphoma, rheumatoid arthritis, systemic lupus erythematosus, multiple sclerosis, glaucoma, diabetes, sepsis, shock, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD) or bronchitis. It is contemplated that a compound of this invention may be useful in treating one or more of the diseases listed.

DETAILED DESCRIPTION

In one embodiment, the present invention discloses cannabinoid receptor ligands represented by structural formula I, or a pharmaceutically acceptable salt or solvate thereof, wherein the various moieties are described above.

In a preferred embodiment of compounds of formula I, $L^1$ is —$CH_2$—, —C(O)—, —S(O)—, —C(O)O— or —S($O_2$)—.

In another preferred embodiment, $L^2$ is —$CH_2$—, —C(H)(alkyl)-, —C(alkyl)$_2$—, —C(O)—, —SO— or —S($O_2$)—.

In another preferred embodiment, $L^3$ is —C(O)— or —S($O_2$)—.

In another preferred embodiment, $R^1$ is alkyl, haloalkyl, cycloalkyl, aryl or heteroaryl, wherein each of said aryl and heteroaryl can be unsubstituted or optionally independently substituted with one to three moieties which can be the same or different and are independently selected from halogen, alkyl, cycloalkyl, haloalkyl, haloalkoxy, —N($R^7$)$_2$, —CN, ($C_1$-$C_6$)alkoxy and OH.

In another preferred embodiment, $R^2$ is H, OH, halogen, $CF_3$, alkoxy, —N($R^7$)$_2$, alkyl, ($C_1$-$C_6$)haloalkyl, ($C_3$-$C_5$)cycloalkyl or —$CH_2$—($C_3$-$C_5$)cycloalkyl.

In another preferred embodiment, $R^3$ and $R^4$ are the same or different, and are independently H or $C_1$-$C_6$ alkyl.

In another preferred embodiment, $R^5$ is H or $C_1$-$C_6$ alkyl.

In another preferred embodiment, $R^6$ is H, $C_1$-$C_6$ alkyl, or haloalkyl.

In another preferred embodiment, A is phenyl, naphthyl, indolyl, furanyl or pyridyl.

In another preferred embodiment, X is selected from the group consisting of H, halogen, alkyl, haloalkyl, ($C_3$-$C_5$) cycloalkyl, hydroxy, alkoxy, and haloalkoxy.

In another preferred embodiment, n is 0-2.

In an additional preferred embodiment, $R^1$ is alkyl, haloalkyl, cycloalkyl, aryl or heteroaryl, wherein each of said aryl and heteroaryl can be unsubstituted or optionally independently substituted with one to three moieties which can be the same or different and are independently selected from the group consisting of halogen, alkyl, cycloalkyl, haloalkyl, haloalkoxy, ($C_1$-$C_6$)alkoxy and OH.

In an additional preferred embodiment, $L^1$ is —$CH_2$—, —C(O)O— or —S($O_2$)—.

In an additional preferred embodiment, $L^2$ is —$CH_2$— or —S($O_2$)—.

In an additional preferred embodiment, $L^3$ is —C(O)— or —S($O_2$)—.

In an additional preferred embodiment, $R^2$ is H, OH, halogen, $CF_3$, alkoxy, ($C_1$-$C_6$)alkyl, ($C_1$-$C_6$)haloalkyl, ($C_3$-$C_5$) cycloalkyl or —$CH_2$—($C_3$-$C_5$)cycloalkyl.

In an additional preferred embodiment, $R^3$ and $R^4$ are H.

In an additional preferred embodiment, $R^5$ is H or $C_1$-$C_6$ alkyl.

In an additional preferred embodiment, $R^6$ is H, $C_1$-$C_6$ alkyl, or haloalkyl.

In an additional preferred embodiment, A is phenyl, indolyl or pyridyl.

In an additional preferred embodiment, X is selected from H, halogen, alkyl, haloalkyl, ($C_3$-$C_5$)cycloalkyl, hydroxy, alkoxy, and haloalkoxy.

In an additional preferred embodiment, n is 0-2.

In a still additional preferred embodiment, $L^1$ is —C(O)O— or —S($O_2$)—.

In a still additional preferred embodiment, $L^2$ is —S($O_2$)—.

In a still additional preferred embodiment, $L^3$ is —C(O)— or —S($O_2$)—.

In a still additional preferred embodiment, $R^1$ is selected from t-butyl, i-propyl, neopentyl, 2-trifluoromethyl-2-propyl, 1,1-bis(trifluoromethyl)-1-ethyl, 2-fluorophenyl, 2,6-difluorophenyl, 2-pyridyl, and 2-pyrimidyl.

In a still additional preferred embodiment, $R^2$ is H, F, ($C_1$-$C_6$)alkyl, OH, or alkoxy.

In a still additional preferred embodiment, $R^3$ and $R^4$ are H.

In a still additional preferred embodiment, $R^5$ is H.

In a still additional preferred embodiment, $R^6$ is $CH_3$ or $CF_3$.

In a still additional preferred embodiment, A is phenyl, indolyl or pyridyl.

In a still additional preferred embodiment, X is selected from H, OH, Cl, Br, $CF_3$, $CH_3$O—, $CF_3$O— and $CHF_2$O—.

In a still additional preferred embodiment, n is 0-2.

A particularly preferred compounds of the invention are represented by general formulas 2 and 3:

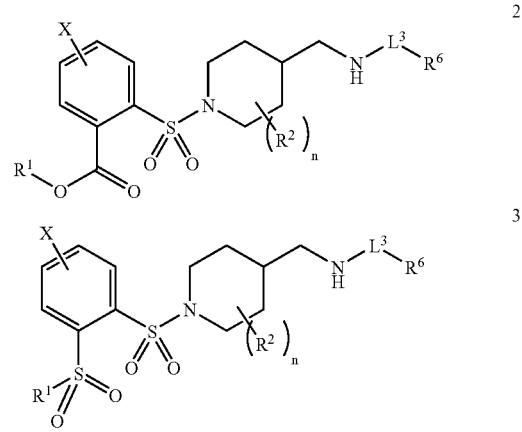

wherein:
$R^1$ is selected from the group consisting of alkyl, haloalkyl, cycloalkyl, aryl and heteroaryl, wherein each of said aryl and heteroaryl can be unsubstituted or optionally substituted with one to five moieties which moieties can be the same or different and are independently selected from the group consisting of halogen, alkyl, cycloalkyl, haloalkyl, haloalkoxy, ($C_1$-$C_6$)alkoxy and/or OH;

$R^2$ is H, OH, F, ($C_1$-$C_6$)alkyl, ($C_1$-$C_6$)haloalkyl, alkoxy or ($C_3$-$C_5$)cycloalkyl;

$R^6$ is H, $C_1$-$C_6$ alkyl or haloalkyl;

$L^3$ is —C(O)— or —S($O_2$)—; and

X is selected from H, halogen, alkyl, haloalkyl, hydroxy, alkoxy, ($C_3$-$C_5$)cycloalkyl and haloalkoxy.

In additionally preferred compounds of the formulas 2 and 3 above, X is selected from —OCH₃, —OCHF₂, —OCF₃, OH or halogen and n is 0-2.

In still additionally preferred compounds of formulas 2 and 3 above, X is selected from —OCH₃ and chlorine.

Additional preferred compounds are represented by general formulas 4 and 5:

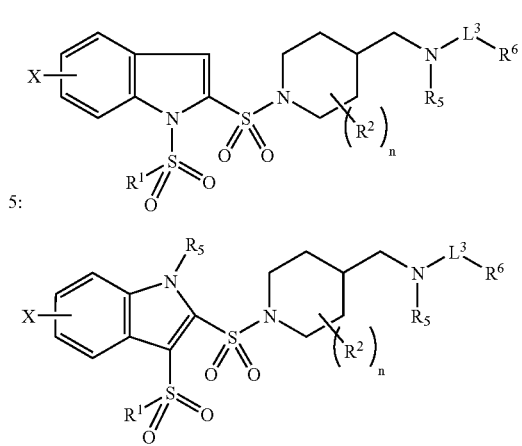

wherein, in formulas 4 and 5:

$L^3$ is —C(O)— or —S(O₂);

$R^1$ is alkyl, haloalkyl, cycloalkyl, aryl or heteroaryl, wherein said aryl and heteroaryl can be unsubstituted or optionally substituted with one to five moieties which can be the same or different and are independently selected from the group consisting of halogen, OH; alkyl, cycloalkyl, haloalkyl, haloalkoxy, and/or (C₁-C₆)alkoxy $R^2$ is H, OH, F, (C₁-C₆)alkyl, (C₁-C₆)haloalkyl, alkoxy or (C₃-C₅)cycloalkyl, CH₂—(C₃-C₅)cycloalkyl;

$R^5$ is H, alkyl, or aryl $R^6$ is H, C₁-C₆ alkyl, or haloalkyl;

X is selected from the group consisting of H, halogen, alkyl, haloalkyl, (C₃-C₅)cycloalkyl, alkoxy, hydroxy and haloalkoxy; and n is 0-2.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)₂, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Alkylene" means a difunctional group obtained by removal of a hydrogen atom from an alkyl group that is defined above. Non-limiting examples of alkylene include methylene, ethylene and propylene.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyridyl-N-oxide, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" or "halo" means fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, heteroaralkyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, and the like.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

"Halogenated alkyl" or "haloalkyl" means alkyl having 1 or more halogen atoms.

"Heteroalkyl" means straight or branched alkyl chain comprised of from 1 to 12 carbon atoms and 1 or more heteroatoms independently selected from the group consisting of N, O and S.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula II, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula III or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formula III can form salts which are also within the scope of this invention. Reference to a compound of Formula III herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula III contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula III may be formed, for example, by reacting a compound of Formula III with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula III, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The compounds of the present invention can be useful as cannabinoid receptor ligands. The compounds can have anti-inflammatory activity and/or immunomodulatory activity and can be useful in the treatment of various medical conditions including, e.g., cutaneous T-cell lymphoma, rheumatoid arthritis, systemic lupus erythematosus, multiple sclerosis, glaucoma, diabetes, sepsis, shock, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD) or bronchitis. It is contemplated that a compound of this invention may be useful in treating one or more of the diseases listed.

Additionally, a compound of the present invention may be co-administered or used in combination with disease-modifying antirheumatic drugs (DMARDS) such as methotrexate, azathioprine, leflunomide, pencillinamine, gold salts, mycophenolate mofetil, cyclophosphamide and other similar drugs. They may also be co-administered with or used in combination with NSAIDS such as piroxicam, naproxen, indomethacin, ibuprofen and the like; COX-2 selective inhibitors such as Vioxx® and Celebrex®; immunosuppressives such as steroids, cyclosporin, Tacrolimus, rapamycin and the like; biological response modifiers (BRMs) such as Enbrel®, Remicade®, IL-1 antagonists, anti-CD40, anti-CD28, IL-10, anti-adhesion molecules and the like; and other anti-inflammatory agents such as p38 kinase inhibitors, PDE4 inhibitors, TACE inhibitors, chemokine receptor antagonists, Thalidomide and other small molecule inhibitors of pro-inflammatory cytokine production.

Also additionally, a compound of the present invention may be co-administered or used in combination with an H1 antagonist for the treatment of seasonal allergic rhinitis and/or asthma. Suitable H1 antagonists may be, for example, Claritin®, Clarinex®, Allegra®, or Zyrtec®.

In another aspect, the invention provides a method for treating rheumatoid arthritis comprising administering a compound of the formula I in combination with compound selected from the class consisting of a COX-2 inhibitor e.g. Celebrex®D or Vioxx®; a COX-1 inhibitor e.g. Feldene®; an immunosuppressive e.g. methotrexate or cyclosporin; a steroid e.g. β-methasone; and anti-TNF-α compound, e.g. Enbrel® or Remicade®; a PDE IV inhibitor, or other classes of compounds indicated for the treatment of rheumatoid arthritis.

In another aspect, the invention provides a method for treating multiple sclerosis comprising administering a compound of the formula I in combination with a compound selected from the group consisting of Avonex®, Betaseron, Copaxone or other compounds indicated for the treatment of multiple sclerosis.

In another aspect, the invention relates to a pharmaceutical composition comprising a therapeutically effective amount of a compound of formula I in a pharmaceutically acceptable carrier.

In yet another aspect, the invention relates to a pharmaceutical composition for treating rheumatoid arthritis comprising a therapeutically effective amount of a compound of formula 1 in combination with a compound selected from the class consisting of a COX-2 inhibitor, a COX-1 inhibitor, an immunosuppressive, a steroid, an anti-TNF-α compound or other classes of compounds indicated for the treatment of rheumatoid arthritis. In still another aspect, the invention relates to a pharmaceutical composition for treating multiple sclerosis comprising a therapeutically effective amount of a compound of formula 1 in combination with a compound selected from the group consisting of Avonex®, Betaseron, Copazone or other compounds indicated for the treatment of multiple sclerosis.

Compounds of the present invention are generally prepared by processes known in the art, for example, by the processes described below.

The following abbreviations are used in the procedures and schemes: aqueous (aq.), anhydrous (anhyd), n-butyl (n-Bu), n-butyllithium (n-BuLi), concentrated (conc.), diethyl ether (Et$_2$O), days (d), 1-(3-dimethylaminopropyl)-3-ethylcarbodiimide hydrochloride (EDCl), dimethylformamide (DMF), ethanol (EtOH), ethyl (Et), ethyl acetate (EtOAc), hours (h), leaving group (LG), hydroxybenzotriazole (HOBT), meta-chloroperoxybenzoic acid (MCPBA), lithium diisopropylamide (LDA), methanesulfonyl chloride (MsCl), methanol (MeOH), minutes (min), methyl (Me), methyllithium (MeLi), molar (moles per liter, M), N-chlorosuccinimide (NCS), N,N-dimethylaminopyridine (DMAP), normal (N), pounds per square inch (psi), preparative thin layer chromatography (PTLC), room temperature (rt), saturated sodium chloride solution (brine), silica gel chromatography (sgc), 2-(tert-butoxycarbonyloxyimino)-2-phenylacetonitrile (BOC-ON), tert-butoxycarbonyl (BOC), trifluoroacetic anhydride (TFAA), trifluoroacetic acid (TFA), trifluoromethanesulfonic anhydride (Tf$_2$O), and tetrahydrofuran (THF). In a typical work-up procedure, the reaction mixture is diluted with a suitable solvent, such as EtOAc, Et$_2$O, or CH$_2$Cl$_2$, and washed successively with appropriate acidic, basic, or neutral aqueous solutions. The organic solution is separated, dried over an appropriate drying agent such as MgSO$_4$ or Na$_2$SO$_4$, filtered, and the solvent removed by evaporation.

General Scheme I
Preparation of Arenesulfonyl Piperidine Compounds

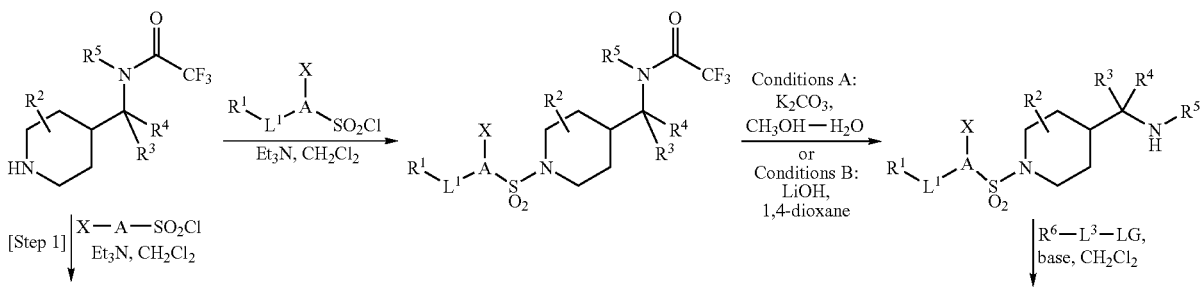

-continued

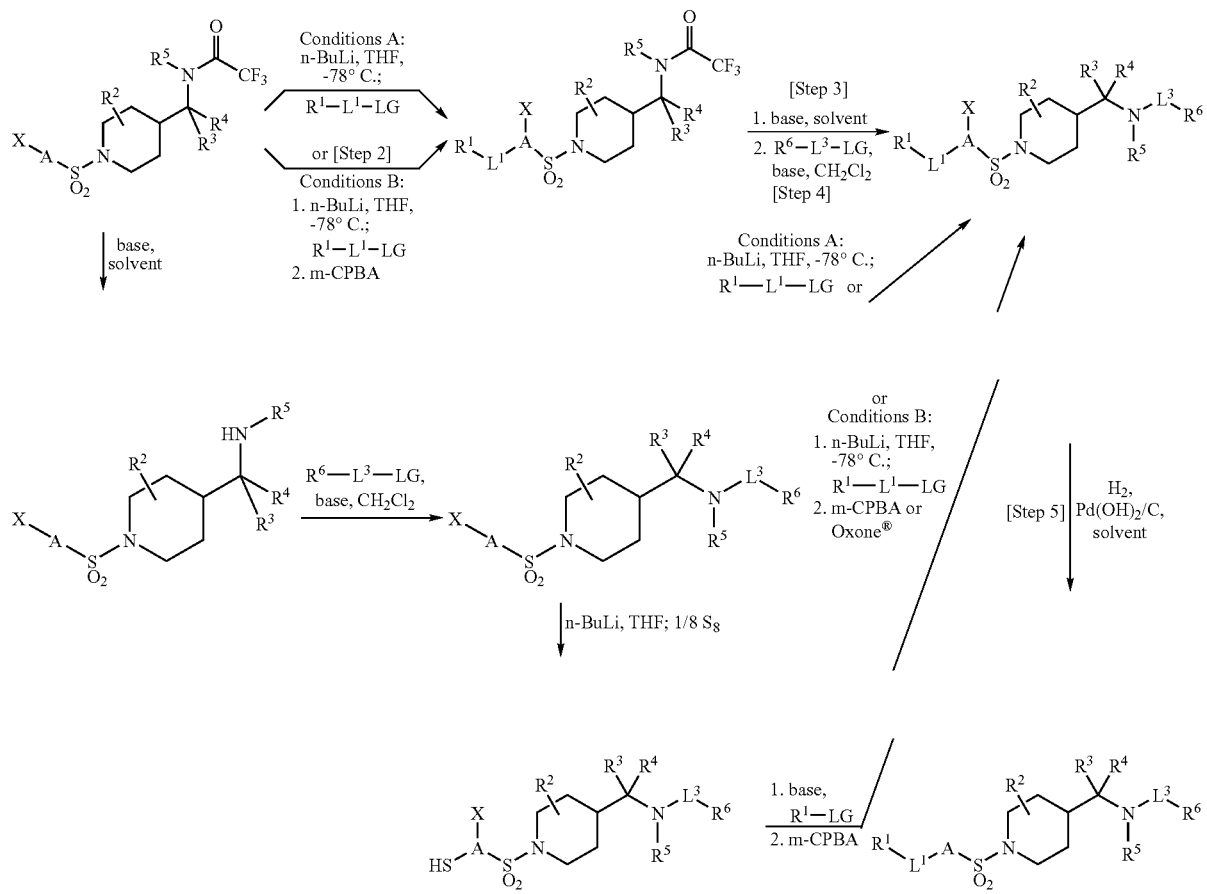

Description of Reaction Scheme I

In step 1, a suitably protected and optionally functionalized 4-(aminomethyl)piperidine derivative is dissolved in $CH_2Cl_2$, a tertiary amine base added, and the resulting solution cooled to 0° C. A solution of an arenesulfonyl chloride in $CH_2Cl_2$ is added. The reaction mixture is stirred at 0° C. to rt for 2-24 h, and then worked up. The product is isolated, and optionally purified by sgc.

In step 2, the product from step 1 is dissolved in a suitable solvent, such as THF, and cooled to −78° C. n-BuLi is added, and the resulting dianion solution is stirred for 30 min, then treated with an appropriate electrophile, such as a dialkyl dicarbonate, a sulfonyl fluoride, a disulfide, or elemental sulfur. The reaction is allowed to proceed at −78° C. to rt for 3-24 h, then worked up, and the product is purified by sgc.

In step 3, the product of step 2 is dissolved in a suitable solvent, such as MeOH or 1,4-dioxane, and an aq. base solution, such as of potassium carbonate or lithium hydroxide, is added. The reaction mixture is stirred at rt for 1-24 h and then worked up.

In step 4, the product from step 3 is dissolved in an appropriate solvent, such as $CH_2Cl_2$, and cooled to between 0° C. and −78° C. The resulting solution is combined with a tertiary amine base and a suitable acylating or sulfonylating agent such as TFAA or $Tf_2O$. The reaction is allowed to proceed at a temperature between −78° C. and rt for 1-24 h. The reaction is then worked up and the crude product purified by sgc.

In step 5, the product from step 4 is dissolved in an appropriate solvent, such as MeOH, and a suitable catalyst, such as palladium hydroxide on carbon, is added. The reaction mixture is exposed to a hydrogen atmosphere (ambient pressure to 60 psi) for 1-24 h, and then worked up. The product is isolated and purified by sgc or PTLC.

For the preparation of some compounds, step 2 may be omitted.

If the electrophile in step 2 is a disulfide, the product of step 2 is dissolved in an appropriate solvent, such as $CH_2Cl_2$, treated with an oxidant such as MCPBA, and the reaction mixture stirred for 1-24 h between 0° C. and rt. The reaction is then worked up. The product is isolated, purified by sgc, and then used in step 3.

If the electrophile in step 2 is elemental sulfur, the product of step 2 is treated with a base, such as sodium hydride, in a suitable solvent, such as THF. An appropriate electrophile is added, and the reaction mixture is stirred at 0° C. to rt for 1-24 h, then worked up, and the product isolated. This product is then dissolved in an appropriate solvent, such as $CH_2Cl_2$, treated with an oxidant such as MCPBA, and the reaction mixture stirred for 1-24 h between 0° C. and rt. The reaction is then worked up. The product is isolated, purified by sgc, and then used in step 3.

Optionally, step 2 may be postponed and carried out immediately following step 4 of the synthetic sequence.

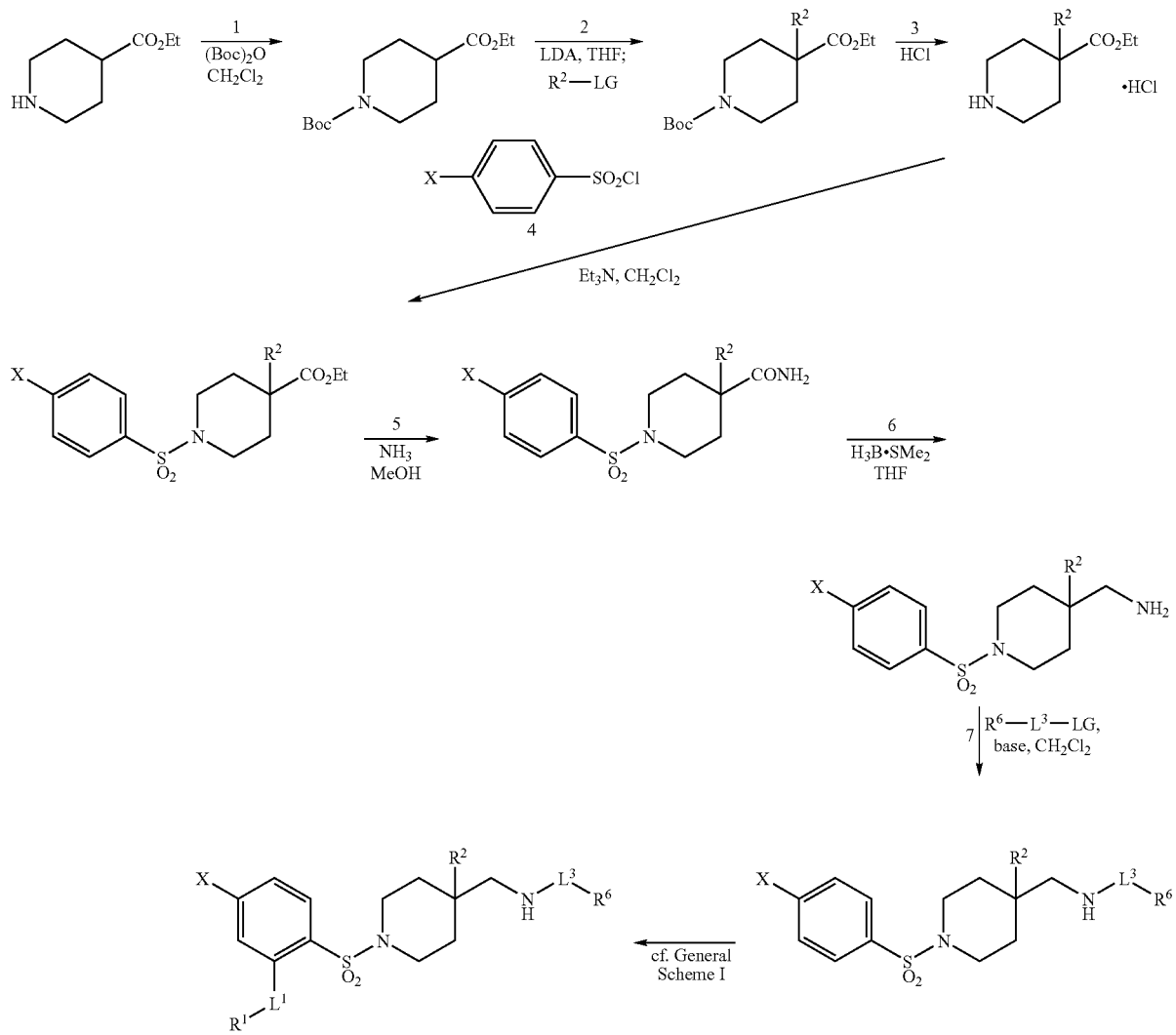

General Scheme II
Preparation of 4-Fluoro- and 4-Alkylpiperidine Compounds

Description of Reaction Scheme II

In step 1, a solution of a dialkyl dicarbonate in an appropriate solvent, such as CH$_2$Cl$_2$, is added to a solution of an alkyl isonipecotate in the same solvent. The reaction is allowed to proceed at 0° C. to rt for 2-24 h, then worked up, and the product purified by sgc.

In step 2, a solution of the product from step 1 in an appropriate solvent, such as THF, is added to a solution of a base, such as LDA, in the same solvent and allowed to react at −78° C. to 0° C. for 0.5-2 h. A suitable electrophile is added and the reaction is allowed to proceed for 2-24 h between 0° C. and rt. The reaction is worked up, and the product is isolated and purified by sgc.

In step 3, the product from step 2 is acidified, such as with a solution of hydrogen chloride in 1,4-dioxane, and stirred at rt for 1-24 h. The solvent is then removed by evaporation.

In step 4, the product from step 3 is dissolved in CH$_2$Cl$_2$ a tertiary amine base added, and the resulting solution cooled to 0° C. A solution of an appropriate arenesulfonyl chloride in CH$_2$Cl$_2$ is added. The reaction mixture is stirred at 0° C. to rt for 2-24 h, then worked up. The product is isolated and purified by sgc.

In step 5, the product from step 4 is allowed to react with a methanolic ammonia solution at rt for 2-48 h. The resulting product is isolated by evaporation of the solvent.

In step 6, a reducing agent, such as borane-methyl sulfide complex, is added to a suspension of the product from step 5 in an appropriate solvent, such as THF. The reaction is allowed to proceed for 1-24 h between room and reflux temperatures. The reaction is quenched with acid, worked up, and the product isolated.

In step 7, the product from step 6 is dissolved in CH$_2$Cl$_2$ a tertiary amine base added, and the resulting solution cooled to 0° C. A solution of an arenesulfonyl chloride in CH$_2$Cl$_2$ is added. The reaction mixture is stirred at 0° C. to rt for 2-24 h, and then worked up. The product is isolated, and optionally purified by sgc.

The product of step 7 can be converted to the final product via sequences presented in General Scheme I.

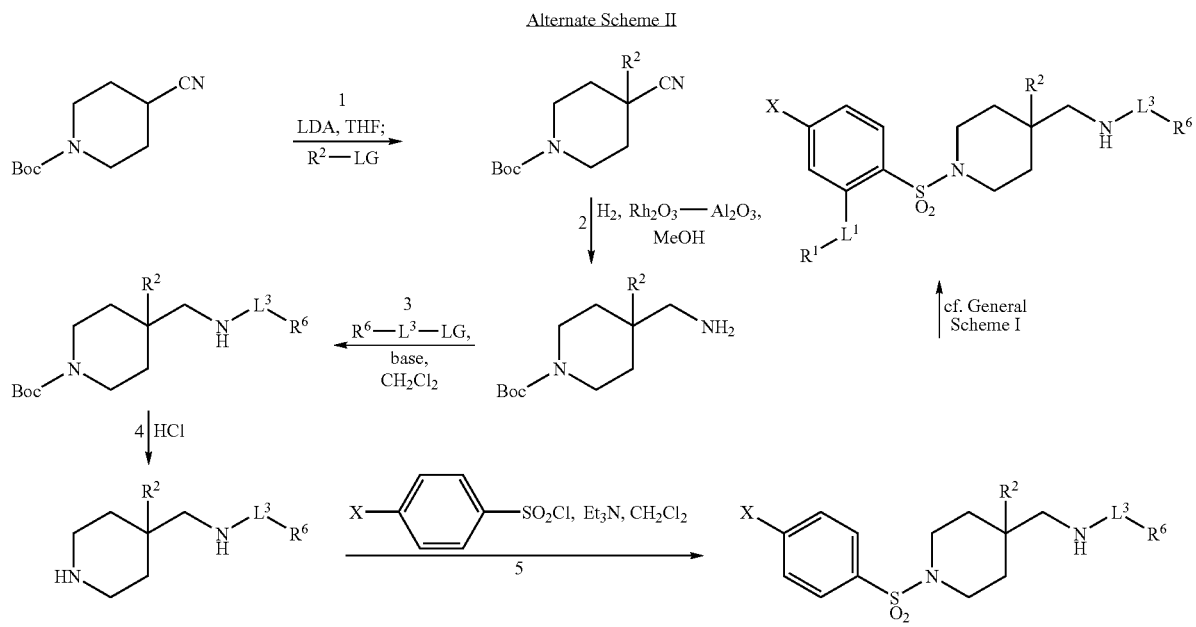

The product of step 7 can be accessed via an alternative five-step route starting with an appropriately protected 4-cyanopiperidine derivative. In step 1 of the alternative pathway, dissolution of the 4-cyanopiperidine derivative in a suitable solvent, such as THF, is followed by sequential treatment with a base, such as LDA, and an electrophile. The reaction mixture is stirred for 2-24 h between −78° C. and rt. The reaction is worked up and the product is isolated and purified by sgc.

In step 2, the product of step 1 is combined with a suitable catalyst, for example rhodium on alumina, in methanolic ammonia solution and exposed to hydrogen atmosphere between ambient and 60 psi pressure. The reaction mixture is filtered, worked up, and the product isolated.

In step 3, the product from step 2 is dissolved in an appropriate solvent, such as $CH_2Cl_2$, and cooled to between 0° C. and −78° C. The resulting solution is combined with a tertiary amine base and a suitable acylating or sulfonylating agent such as TFAA or $Tf_2O$. The reaction is allowed to proceed at a temperature between −78° C. and rt for 1-24 h. The reaction is then worked up and the crude product purified by sgc.

In step 4, the product from step 3 is acidified, such as with a solution of hydrogen chloride in 1,4-dioxane, and stirred at rt for 1-24 h. The solvent is then removed by evaporation.

In step 5, the product from step 4 is dissolved in $CH_2Cl_2$, a tertiary amine base added, and the resulting solution cooled to 0° C. A solution of an arenesulfonyl chloride in $CH_2Cl_2$ is added. The reaction mixture is stirred at 0° C. to rt for 2-24 h, and then worked up. The product is isolated, and optionally purified by sgc.

The product of step 5 can be converted to the final product via sequences presented in General Scheme I.

General Scheme III
Preparation of 4-Cyclopropylpiperidine Compounds

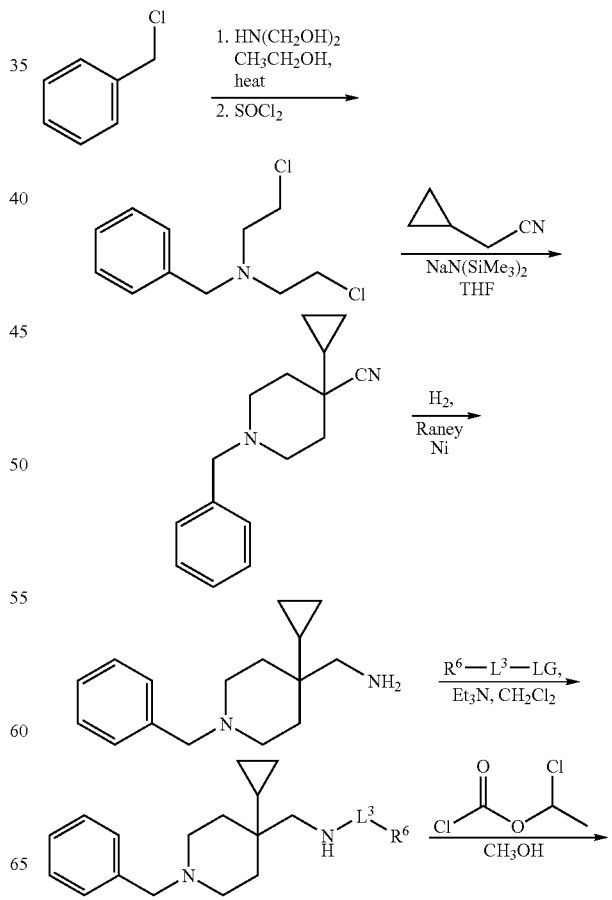

-continued

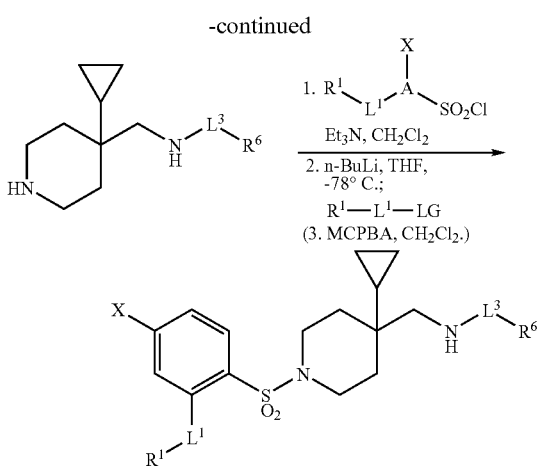

Description of Reaction Scheme III

In step 1, benzyl chloride is allowed to react with diethanolamine in a suitable solvent, such as EtOH, for 68 h at an appropriate temperature. Subsequent treatment with thionyl chloride, in an appropriate solvent, such as 1,2-dichloroethane, affords the protected amino-dichloride.

In step 2, the dichloride, dissolved in an appropriate solvent such as THF, is treated with the anion generated by treatment of cyclopropylacetonitrile with a suitable base such as sodium bis(trimethylsilyl)amide. The reaction is allowed to proceed at 0° C. for 3 h, then worked up, and the resulting cyanopiperidine is purified by sgc.

In step 3, the product of step 2 is dissolved in an appropriate solvent, such as methanolic ammonia, and combined with a suitable catalyst, such as Raney Nickel. The reaction mixture is pressurized with hydrogen gas (typically 20-50 psi) and agitated for an appropriate length of time. The solution is filtered and the reaction is worked up. The resulting amine is purified by sgc.

In step 4, the product of step 3 and an appropriate tertiary amine base are dissolved in an appropriate solvent such as $CH_2Cl_2$ and treated with a suitable electrophile. The reaction is allowed to proceed between −78° C. and rt for 1-24 h.

In step 5, the product of step 4 is dissolved in an appropriate solvent such as $CH_2Cl_2$ or dichloroethane, and combined with an appropriate chlorocarboxylate reagent. The reaction is allowed to proceed for 1-72 h at a temperature between rt and 80° C., then worked up, and the product purified by sgc.

In step 6, the product of step 5 and an appropriate tertiary amine base are dissolved in an appropriate solvent such as $CH_2Cl_2$ and treated with a suitable arenesulfonyl chloride. The reaction is allowed to proceed between 0° C. and rt for 1-24 h, and is then worked up and the product is purified by sgc.

In step 7, the product from step 6 is dissolved in a suitable solvent, such as THF, and cooled to −78° C. n-BuLi is added, and the resulting dianion solution is stirred for 30 min, then treated with an appropriate electrophile, such as a dialkyl dicarbonate, a sulfonyl fluoride, or a disulfide. The reaction is allowed to proceed at −78° C. to rt for 3-24 h, then worked up, and the product is purified by sgc. If a disulfide is used as the electrophile, the product is oxidized with MCPBA in $CH_2Cl_2$.

General Scheme IV
Preparation of 4-Hydroxy- and 4-Alkoxypiperidine Compounds

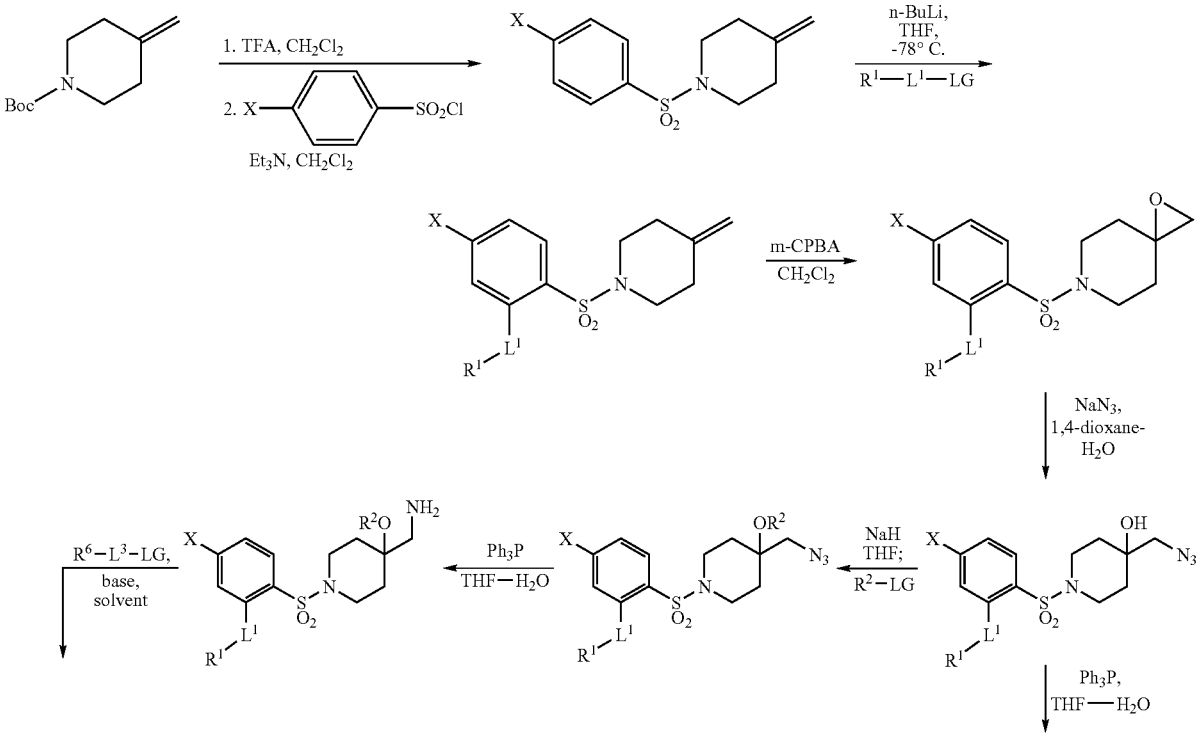

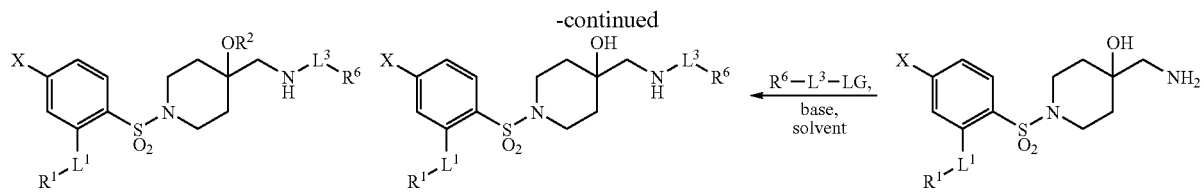

Description of Reaction Scheme IV

In step 1,1-t-butoxycarbonyl-4-methylenepiperidine is stirred in a solution of TFA and $CH_2Cl_2$ for 1-24 h. Removal of the solvent gave crude 4-methylenepiperidine. This crude product is then dissolved in $CH_2Cl_2$ a tertiary amine base added, and the resulting solution cooled to 0° C. A solution of arenesulfonyl chloride in $CH_2Cl_2$ is added. The reaction mixture is stirred at 0° C. to rt for 3-24 h, worked up, and the product purified by sgc.

In step 2, the product from step 1 is dissolved in a suitable solvent, such as THF, and cooled to −78° C. n-BuLi is added, and the resulting dianion solution is stirred for 30 min and then treated with an appropriate electrophile. The reaction is allowed to proceed at −78° C. to rt for 3-24 h further, then worked up, and the product is purified by sgc.

In step 3, the product from step 2 is dissolved in $CH_2Cl_2$ and an oxidant such as MCPBA is added. The reaction mixture is stirred at 0° C. to rt for 1-24 h, then worked up, and the crude product purified by sgc.

In step 4, the product from step 3 is dissolved in a suitable solvent system, such as dioxane and water, and solid sodium azide is added. The reaction is carried out for 2-24 h at rt to reflux temperature of the solvent. The reaction is worked up and the resulting product can be used without further purification.

In step 5. the product from step 4 is dissolved in an appropriate solvent such as THF. A suitable base, such as sodium hydride, and electrophile are added successively. The reaction mixture is stirred at rt for 1-24 h, and then worked up, and the crude product purified by sgc.

In step 6, the product from step 5 is dissolved in an appropriate solvent system, such as THF and water, and a reductant, such as triphenylphosphine, is added. The resulting mixture is stirred at rt for 2-24 h. The reaction is worked up and the product can be purified by sgc.

In step 7, the product from step 6 is dissolved in an appropriate solvent, such as $CH_2Cl_2$, and cooled to −78° C. The resulting solution is combined with a tertiary amine base and a suitable acylating or sulfonylating agent such as TFAA or $Tf_2O$. The reaction is allowed to proceed at −78° C. to rt for 1-24 h, before being worked up and the crude product purified by sgc.

Alternatively, the product from step 4 can be dissolved in an appropriate solvent system, such as THF and water, and a reductant, such as triphenylphosphine, is added. The resulting mixture is stirred at rt for 2-24 h. The reaction is worked up and the product can be purified by sgc. Subsequently, this purified product can be dissolved in an appropriate solvent, such as $CH_2Cl_2$, and cooled to −78° C. The resulting solution is combined with a tertiary amine base and a suitable acylating or sulfonylating agent such TFAA or $Tf_2O$ is added. The reaction is allowed to proceed at −78° C. to rt for 1-24 h, before being worked up and the crude product purified by sgc.

General Scheme V
Preparation of N-(Indolylsulfonyl)piperidine Compounds

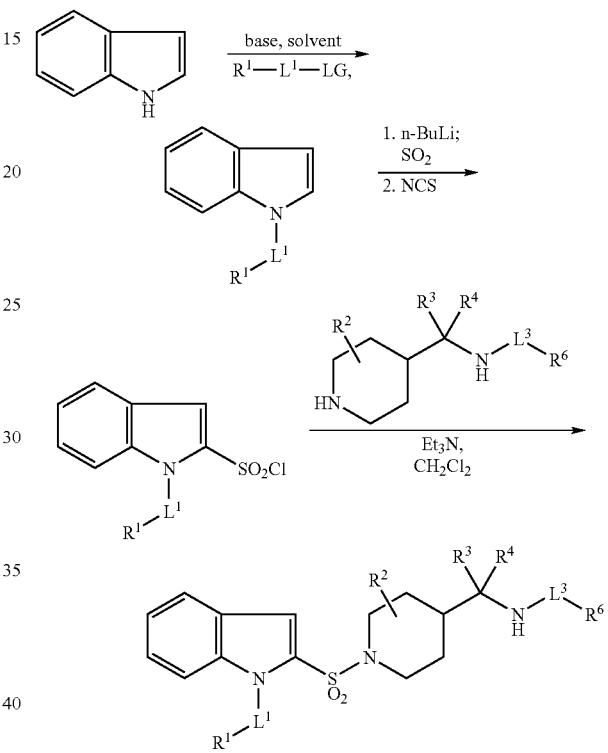

Description of Reaction Scheme V

In step 1, indole is dissolved in a suitable solvent, such as THF, and cooled to −78° C. An appropriate base, such as n-BuLi, is added and reaction mixture is stirred for 15-30 min. A solution of an appropriate electrophile, such as 2-fluorobenzenesulfonyl chloride, in THF is added, and the reaction is allowed to proceed at −78° C. to rt for 2-24 h. The reaction is worked up and the product purified by sgc.

In step 2, the product from step 1 is dissolved in a suitable solvent, such as THF, and cooled to −78° C. n-BuLi is added, and the resulting solution is stirred for 30-60 min and then treated with an appropriate electrophile such as sulfur dioxide. The reaction mixture is concentrated to minimal volume, and hexanes is added. The resulting precipitate is then washed and taken up in an appropriate solvent, such as $CH_2Cl_2$. A chlorinating agent, such as NCS, is added and the reaction mixture is stirred at rt for 2-24 h at rt. The reaction is worked up, and the product is purified by sgc.

In step 3, the product from step 2 is dissolved in a suitable solvent, such as $CH_2Cl_2$, and added to a solution of a tertiary amine base and an appropriately protected and optionally substituted secondary amine in the same solvent. The reaction is allowed to proceed at rt for 2-24 h, then worked up, and the product purified by sgc or PTLC.

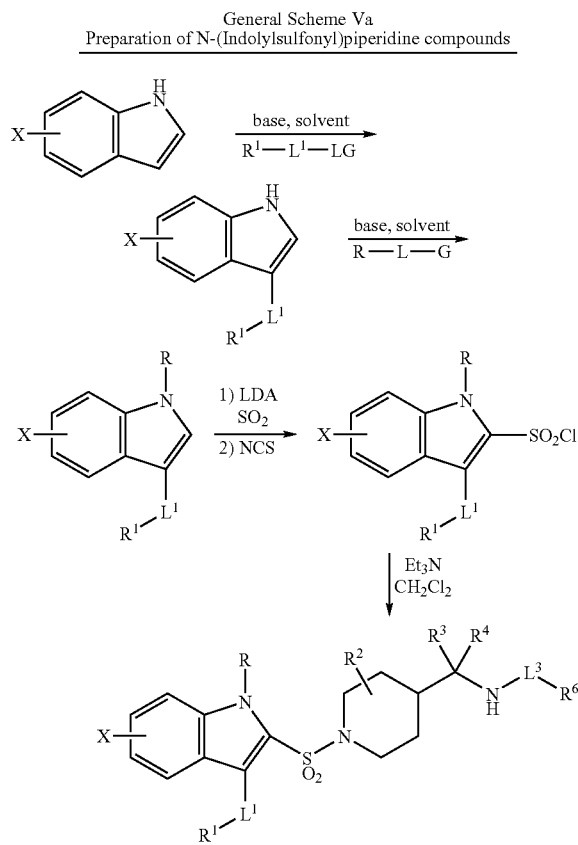

General Scheme Va
Preparation of N-(Indolylsulfonyl)piperidine compounds

Description of Reaction Scheme Va

In step 1, indole derivative is dissolved in a suitable solvent, such as DMF, THF and cooled to 0° C. An appropriate base, such as NaH, is added and the reaction mixture is stirred for 15 min. A solution of an appropriate electrophile, such as 2-fluorophenyl disulphide, is added, and the reaction is allowed to proceed at r.t. for 2-24 h. The product may be purified via sgc or crystallization.

In step 2, the product from step 1 is dissolved in a suitable solvent, such as DMF, THF. An appropriate base, such as NaH, is added and the reaction mixture is stirred for 15 min. A solution of an appropriate electrophile, such as iodomethane, is added, and the reaction is allowed to proceed at r.t. for 2-24 h. The product may be purified via sgc or crystallization.

In step 3, the product from step 2 is dissolved in THF, cooled in a dry ice/IPA bath and treated with LDA. The resulting anion is trapped with $SO_2$ gas followed by reacting with NCS. The product may be purified via chromatography or crystallization.

In step 4, the product from step 3 is dissolved in a suitable solvent, such as $CH_2Cl_2$, and added to a solution of a tertiary amine and an appropriately protected and optionally substituted secondary amine in the same solvent. The reaction is allowed to proceed at rt for 2-24 h. The product may be purified via sgc or crystallization.

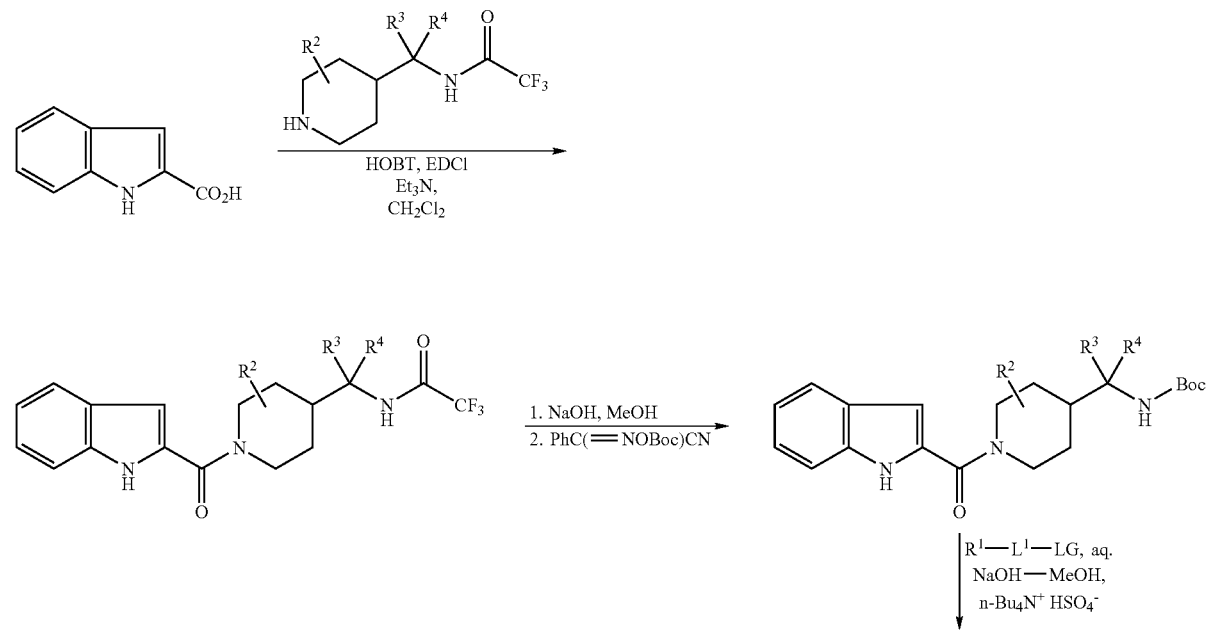

General Scheme VI
Preparation of N-(Indolylcarbonyl)piperidine Compounds

-continued

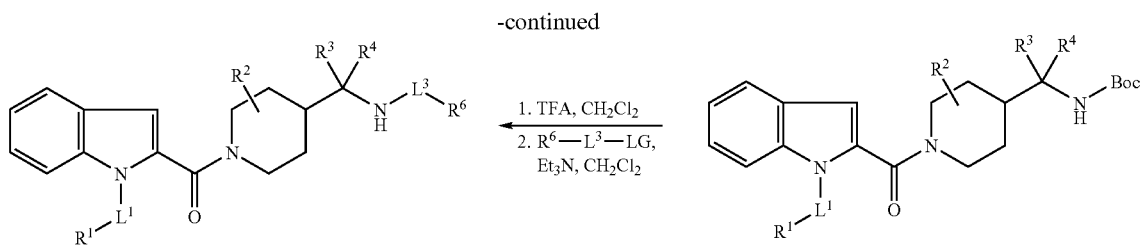

Description of Reaction Scheme VI

In step 1, indole-2-carboxylic acid and an appropriately protected, optionally substituted piperidine derivative are dissolved in a suitable solvent, such as $CH_2Cl_2$. HOBT, EDCl, and a tertiary amine base are added successively, and the reaction is allowed to proceed at rt for 2-24 h. The reaction is worked up and the product purified by sgc.

In step 2, the product from step 1 is dissolved in an alcoholic solvent, and aq. base is added. The reaction is allowed to proceed at rt for 2-24 h before being worked up. The product can be used without purification.

In step 3, the product from step 2 is dissolved in an appropriate solvent system, such as THF and $CH_2Cl_2$. BOC-ON and a catalytic amount of DMAP are added and the reaction is allowed to proceed at rt for 2-24 h. The reaction is then worked up and the crude product purified by sgc or PTLC.

In step 4, the product from step 3 is dissolved in $CH_2Cl_2$. An aq. base solution, such as sodium hydroxide, and a phase transfer catalyst, such as tetrabutylammonium hydrogen sulfate, are added successively and the resulting mixture is stirred at rt for 2-24 h. After work-up, the crude product can be purified by sgc or PTLC.

In step 5, the product from step 4 is stirred in a solution of TFA and $CH_2Cl_2$ for 1-24 h. The solvent is evaporated, and the resulting product can be used without further purification.

In step 6, the product from step 5 is dissolved in an appropriate solvent, such as $CH_2Cl_2$, and cooled to between 0° C. and −78° C. The resulting solution is combined with a tertiary amine base and a suitable acylating or sulfonylating agent such as TFAA or $Tf_2O$. The reaction is allowed to proceed at a temperature between −78° C. and rt for 1-24 h. The reaction is then worked up and the crude product purified by sgc.

General Scheme VII
Preparation of N-Arylmethyl piperidine Compounds

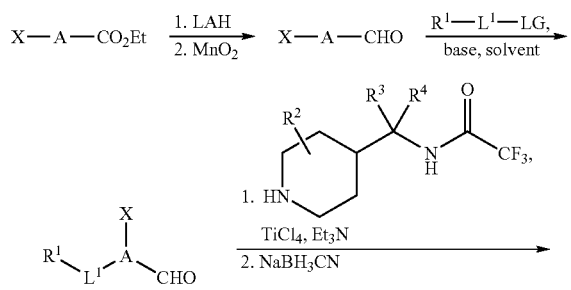

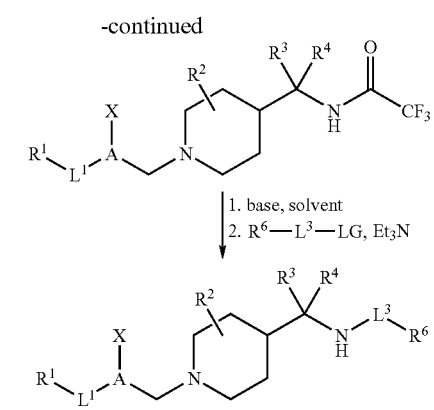

Description of Reaction Scheme VII

In step 1, an ester, such as ethyl indole-2-carboxylate, and lithium aluminum hydride are stirred at 0° C. to rt for 30 min. The reaction is quenched with water and aq. sodium hydroxide prior to work-up. The isolated alcohol intermediate is dissolved in a suitable solvent, such as $CH_2Cl_2$, and an appropriate oxidant, such as manganese dioxide is added. The reaction mixture is stirred at rt for 0.54 h, then worked up, and the product purified by sgc.

In step 2, the product from step 1 is dissolved in $CH_2Cl_2$. An aq. base solution, such as sodium hydroxide, and a phase transfer catalyst, such as tetrabutylammonium hydrogen sulfate, are added successively and the resulting mixture is stirred at rt for 2-24 h. After subsequent work-up, the crude product can be purified by sgc.

In step 3, the product of step 2 is combined with a suitably protected, optionally substituted 4-aminomethylpiperidine derivative in an appropriate solvent such as $CH_2Cl_2$. A Lewis acid, such as titanium tetrachloride, and a tertiary amine base are added and the reaction mixture is stirred for 2-24 h at rt. A reducing agent, such as sodium cyanoborohydride, is added, and the reaction is allowed to continue for a further 2 h. The reaction is worked up and the crude product is purified by sgc or PTLC.

In step 4, the product of step 3 is dissolved in a suitable solvent, such as 1,4-dioxane, and an aq. base solution, such as of lithium hydroxide, is added. The reaction mixture is stirred at rt for 1-24 h and then worked up.

In step 5, the product from step 4 is dissolved in an appropriate solvent, such as $CH_2Cl_2$, and cooled to between 0° C. and −78° C. The resulting solution is combined with a tertiary amine base and a suitable acylating or sulfonylating agent such as TFAA or $Tf_2O$. The reaction is allowed to proceed at a temperature between −78° C. and rt for 1-24 h. The reaction is then worked up and the crude product purified by sgc.

General Scheme VIII
Preparation of 4-(2'-sulfonamido-2'-propyl)piperidine ("gem-Dimethyl") Compounds

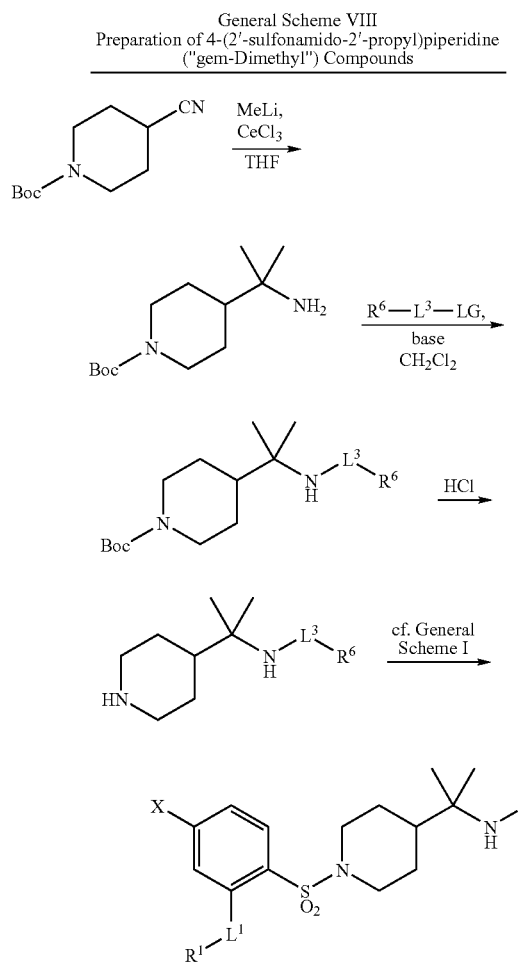

Description of Reaction Scheme VIII

In step 1, methylcerium is prepared by the combination of anhyd. cerium(III) chloride and methyllithium in an appropriate solvent, such as THF. A solution of a protected 4-cyanopiperidine derivative is added and the reaction is allowed to proceed at −78° C. for 2-24 h. The reaction is quenched and worked up, and the product isolated.

In step 2, the product from step 1 is dissolved in an appropriate solvent, such as $CH_2Cl_2$, and cooled to between 0° C. and −78° C. The resulting solution is combined with a tertiary amine base and a suitable acylating or sulfonylating agent such as TFAA or $Tf_2O$. The reaction is allowed to proceed at a temperature between −78° C. and rt for 1-24 h. The reaction is then worked up and the crude product purified by sgc.

In step 3, the product from step 2 is acidified, such as with a solution of hydrogen chloride in 1,4-dioxane, and stirred at rt for 1-24 h. The solvent is then removed by evaporation.

The product from step 3 is converted to the final product according to the procedure outlined in General Scheme I.

General Scheme IX
Preparation of p-(Difluoromethoxy)benzenesulfonyl Piperidine Compounds

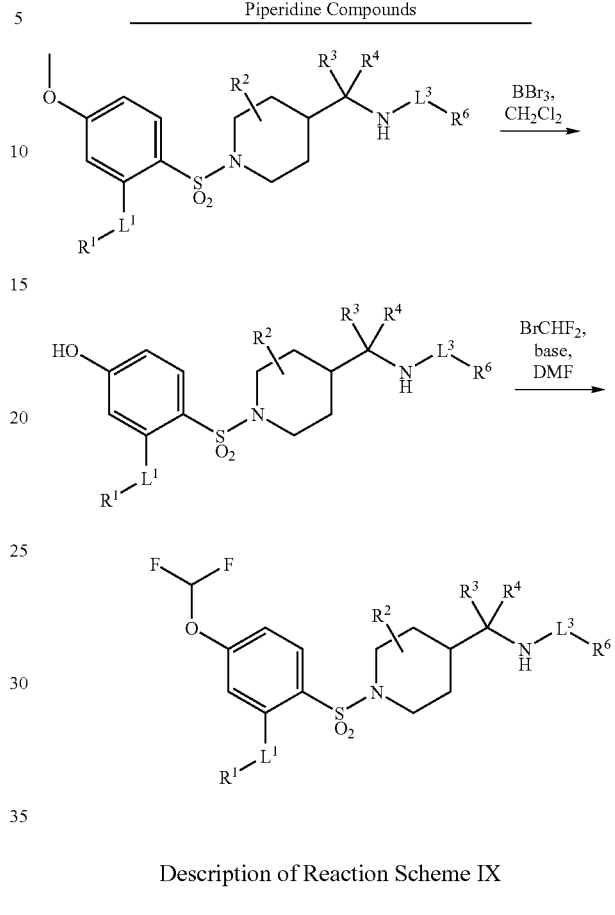

Description of Reaction Scheme IX

In step 1, a functionalized aryl methyl ether, prepared via the method described by General Scheme I, is dissolved in an appropriate solvent, such as $CH_2Cl_2$, and a Lewis acid, such as boron tribromide, is added. The reaction mixture is stirred for 2-24 h between −78° C. and rt, then worked up, and the product isolated.

In step 2, the product of step 1 is dissolved in a polar solvent, such as DMF, and combined with an appropriate base, such as cesium carbonate. Bromodifluoromethane gas is introduced, and the reaction is allowed to proceed at rt to 90° C. for 2-24 h. The reaction is quenched, and the product is isolated and purified by sgc.

General Scheme X
Conversion of t-Butyl Ester Compounds to Other Secondary and Tertiary Esters

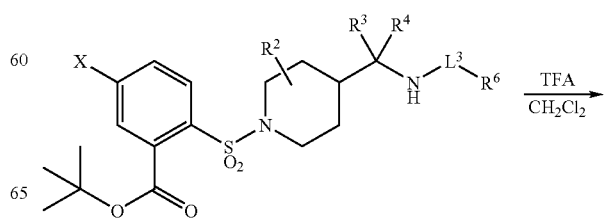

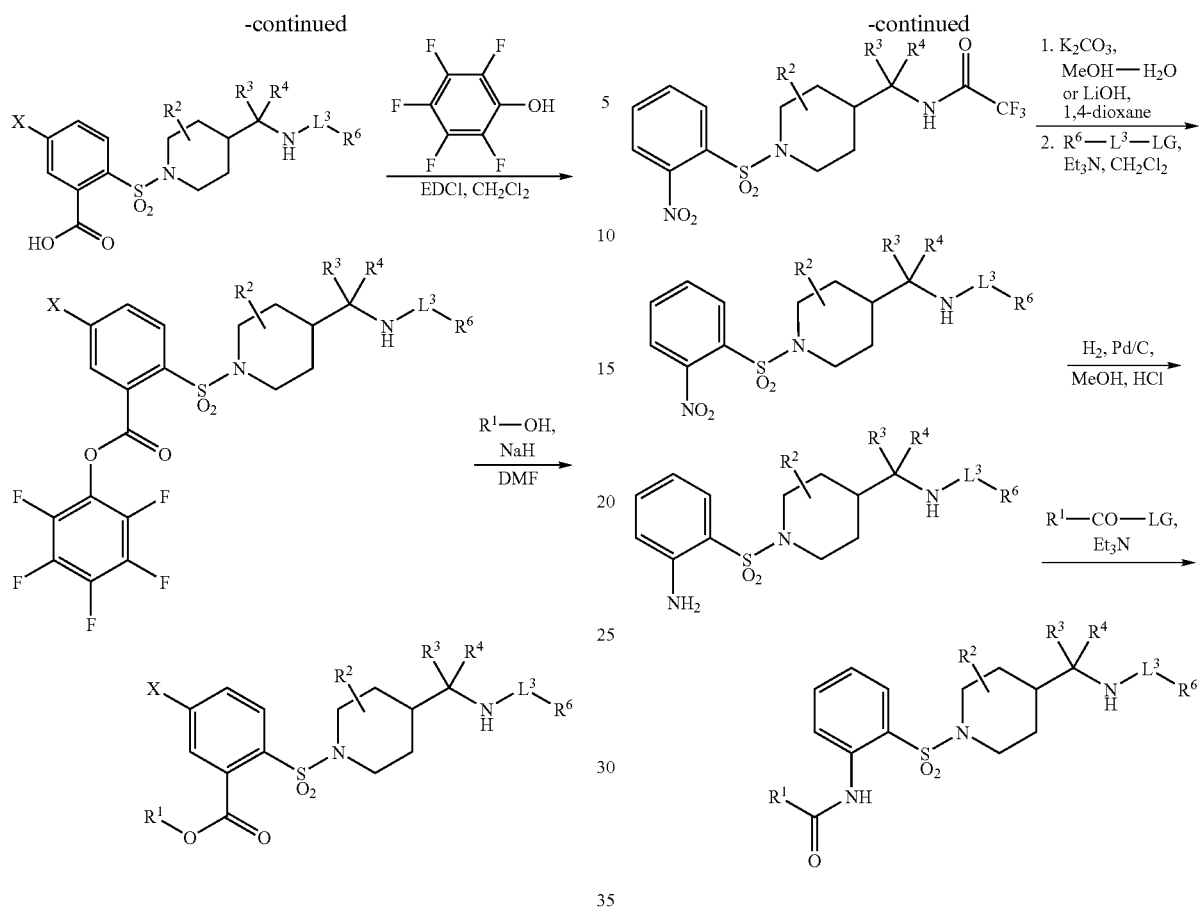

Description of Reaction Scheme X

In step 1, a functionalized t-butyl benzoate derivative, prepared via the method described by General Scheme I, is dissolved in an appropriate solvent such as $CH_2Cl_2$ and acidified, such as with TFA. The reaction mixture is stirred at rt for 1-24 h, then worked up, and the product isolated.

In step 2, the product from step 1 is combined with pentafluorophenol and EDCl in an appropriate solvent, such as $CH_2Cl_2$. The reaction is stirred at rt for 2-24 h, then worked up. The product is isolated and purified by sgc.

In step 3, an alcohol is added to a suspension of a base, such as sodium hydride, in an appropriate solvent, such as DMF. The product from step 2 is then added and the resulting mixture is stirred at rt to 60° C. for 2-24 h. The reaction is worked up, the product isolated, and then purified by sgc.

General Scheme XI
Preparation of o-Amidobenzenesulfonyl Piperidine Compounds

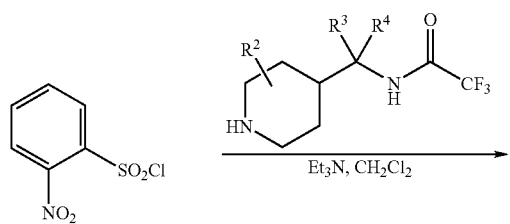

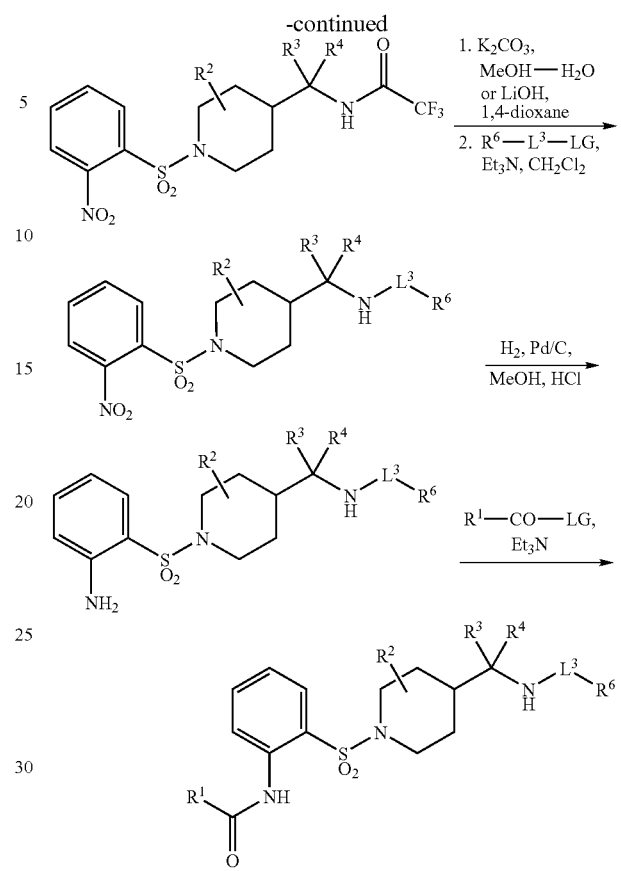

Description of Reaction Scheme XI

In step 1, a suitably protected and optionally functionalized 4-(aminomethyl)piperidine derivative is dissolved in $CH_2Cl_2$ a tertiary amine base added, and the resulting solution cooled to 0° C. A solution of 2-nitrobenzenesulfonyl chloride in $CH_2Cl_2$ is added. The reaction mixture is stirred at 0° C. to rt for 2-24 h, worked up, and the product isolated.

In step 2, the product of step 1 is dissolved in a suitable solvent, such as MeOH, and an aq. base solution, such as of lithium hydroxide, is added. The reaction mixture is stirred at rt for 1-24 h and then worked up and the product isolated.

In step 3, the product from step 2 is dissolved in an appropriate solvent, such as $CH_2Cl_2$, and cooled to between 0° C. and −78° C. The resulting solution is combined with a tertiary amine base and a suitable acylating or sulfonylating agent such as TFAA or $Tf_2O$. The reaction is allowed to proceed at a temperature between −78° C. and rt for 1-24 h. The reaction is then worked up and the crude product purified by sgc.

In step 4, the product from step 3 is dissolved in an appropriate solvent, such as MeOH, combined with conc. hydrochloric acid and a suitable catalyst, such as 10% palladium on carbon, and shaken under hydrogen atmosphere (ambient pressure to 60 psi) for 1-24 h. The reaction mixture is filtered and worked up prior to product isolation.

In step 5, the product from step 4 is dissolved in an appropriate solvent, such as $CH_2Cl_2$, and cooled to between 0° C. and −78° C. The resulting solution is combined with a tertiary amine base and a suitable acylating or sulfonylating agent such as cyclopentanecarbonyl chloride. The reaction is allowed to proceed at a temperature between −78° C. and rt for 1-24 h. The reaction is then worked up and the crude product purified by sgc.

General Scheme XII
Preparation of 5-Aryl Thiophenesulfonyl Piperidine Compounds

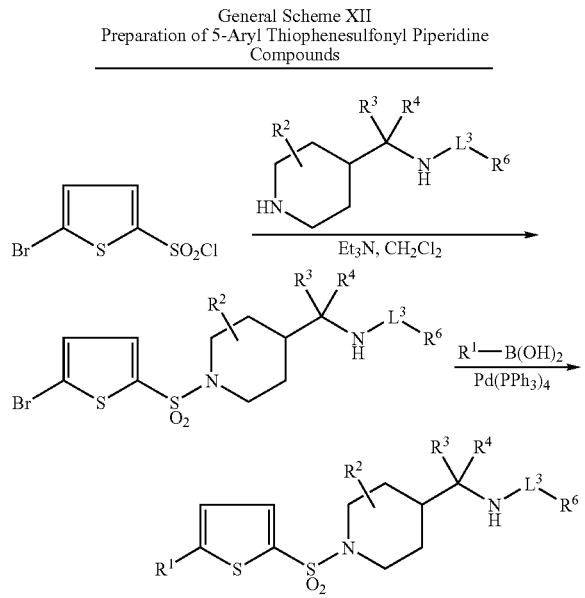

Description of Reaction Scheme XII

In step 1, a suitably protected and optionally functionalized 4-(aminomethyl)piperidine derivative is dissolved in $CH_2Cl_2$, a tertiary amine base added, and the resulting solution is cooled to 0° C. A solution of 5-bromothiophene-2-sulfonyl chloride in $CH_2Cl_2$ is added. The reaction mixture is stirred at 0° C. to rt 2-24 h, worked up, and the product isolated.

In step 2, the product from step 1 is combined with a suitable catalyst, such as tetrakis(triphenylphosphine)palladium(0), in a suitable solvent, such as THF. An aq. solution of base, such as potassium carbonate, is added, followed by an appropriate boronic acid, such as phenylboronic acid. The reaction mixture is stirred for 2-24 h between rt and reflux temperature. The reaction is then worked up. The product is isolated and purified by sgc or PTLC.

General Scheme XIII
Preparation of 5-t-Butyl Thiophenesulfonyl Piperidine Compounds

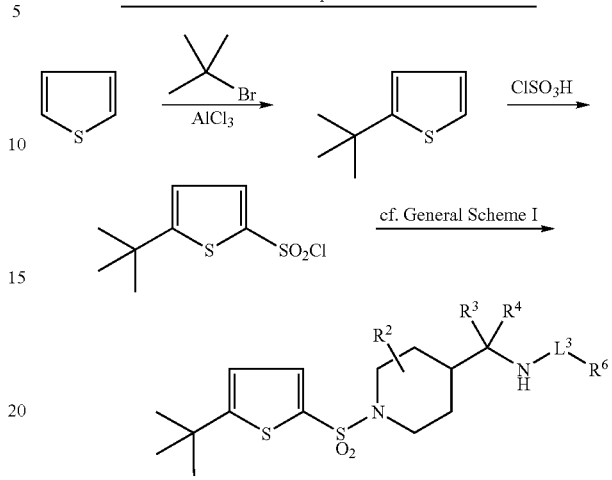

Description of Reaction Scheme XIII

In step 1, a solution of thiophene and t-butyl bromide in an appropriate solvent, such as $CH_2Cl_2$ is added slowly to a suspension of a Lewis acid, such as aluminum trichloride, in the same solvent. The reaction mixture is stirred for 2-24 h between −78° C. and rt, then worked up. The product is isolated and purified by distillation.

In step 2, the product from step 1 is dissolved in an appropriate solvent, such as $CH_2Cl_2$, and the solution added slowly to an ice-cold solution of chlorosulfonic acid in the same solvent. The reaction is allowed to proceed at 0° C. for 30 min, and is then quenched and the product isolated.

The product from step 2 is converted to the final product via the procedure presented in General Scheme 1.

Those skilled in the art will appreciate that similar reactions to those described in the above schemes may be carried out on other compounds of formula I. Starting materials for the above processes are either commercially available, known in the art, or prepared by procedures well known in the art. Exemplary compounds of the present invention are set forth below in Table I.

TABLE I

| Cmp | $R^1$ | $R^2$ | $R^3$ | $R^4$ | $R^6$ | A = | $L^1$ | $L^2$ | $L^3$ | X |
|---|---|---|---|---|---|---|---|---|---|---|
| A | (CH3)3C- | H | H | H | $CF_3$ | (phenyl) | $CO_2$ | $SO_2$ | $SO_2$ | Cl |

TABLE I-continued

Structure: R¹-L¹-A(-X)-L²-N(piperidine with R²)-C(R³)(R⁴)-N(H)-L³-R⁶

| Cmp | R¹ | R² | R³ | R⁴ | R⁶ | A = | L¹ | L² | L³ | X |
|---|---|---|---|---|---|---|---|---|---|---|
| B | tert-butyl (H₃C)₃C- | H | H | H | CH₃ | phenyl (1,3) | CO₂ | SO₂ | SO₂ | OCF₃ |
| C | (F₃C)(H₃C)₂C- | H | H | H | CF₃ | phenyl (1,3) | CO₂ | SO₂ | SO₂ | Cl |
| D | tert-butyl (H₃C)₃C- | H | H | H | CF₃ | phenyl (1,3) | CO₂ | SO₂ | SO₂ | H |
| E | tert-butyl (H₃C)₃C- | H | H | H | CF₃ | phenyl (1,3) | CO₂ | SO₂ | SO₂ | Cl |
| F | tert-butyl (H₃C)₃C- | H | H | H | CH₃ | phenyl (1,3) | CO₂ | SO₂ | SO₂ | Cl |
| G | cyclobutyl | H | H | H | CF₃ | phenyl (1,3) | CO₂ | SO₂ | SO₂ | Cl |
| H | i-propyl | H | H | H | CF₃ | phenyl (1,4) | CO₂ | SO₂ | SO₂ | Cl |
| I | tert-butyl (H₃C)₃C- | H | H | H | CH₃ | phenyl (1,3) | CO₂ | SO₂ | SO₂ | H |
| J | 2-fluorophenyl | H | H | H | CH₃ | phenyl (1,3) | SO₂ | SO₂ | SO₂ | OCH₃ |

TABLE I-continued

| Cmp | R¹ | R² | R³ | R⁴ | R⁶ | A = | L¹ | L² | L³ | X |
|---|---|---|---|---|---|---|---|---|---|---|
| K | phenyl | H | H | H | CH₃ | phenylene | SO₂ | SO₂ | SO₂ | OCH₃ |
| L | 2-F-phenyl | H | H | H | CH₃ | phenylene | SO₂ | SO₂ | SO₂ | OCF₂H |
| M | 2-F-phenyl | H | H | H | CH₃ | phenylene | SO₂ | SO₂ | SO₂ | OCF₃ |
| N | 2-F-phenyl | H | H | H | C₂H₅ | phenylene | SO₂ | SO₂ | SO₂ | OCF₂H |
| O | 2-F-phenyl | H | H | H | CH₃ | phenylene | SO₂ | SO₂ | SO₂ | Cl |
| P | 2-F-phenyl | H | H | H | C₂H₅ | phenylene | SO₂ | SO₂ | SO₂ | OCF₃ |
| Q | 2-F-phenyl | H | H | H | CF₃ | phenylene | SO₂ | SO₂ | SO₂ | CF₃ |
| R | 2,3-di-F-phenyl | H | H | H | CF₃ | phenylene | SO₂ | SO₂ | SO₂ | Cl |
| S | 2-F-phenyl | H | H | H | CF₃ | phenylene | SO₂ | SO₂ | C=O | OCH₃ |

TABLE I-continued
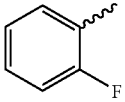
| Cmp | R¹ | R² | R³ | R⁴ | R⁶ | A = | L¹ | L² | L³ | X |
|---|---|---|---|---|---|---|---|---|---|---|
| T | 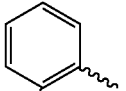 | H | H | H | CH₃ | 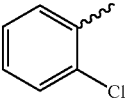 | SO₂ | SO₂ | SO₂ | H |
| U | 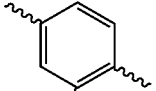 | H | H | H | CF₃ | 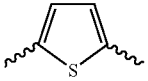 | SO₂ | SO₂ | C=O | OCH₃ |
| V | Br | H | H | H | CH₃ | 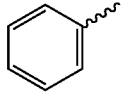 | CB | SO₂ | SO₂ | H |
| W | 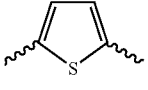 | H | H | H | CH₃ | 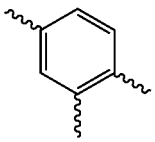 | CB | SO₂ | SO₂ | H |
| X | C₃H₇ | H | H | H | CH₃ | 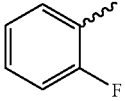 | SO₂ | SO₂ | SO₂ | OCH₃ |
| Y | 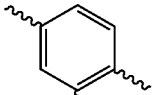 | H | H | H | CF₃ | 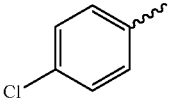 | SO | SO₂ | C=O | Cl |
| Z | 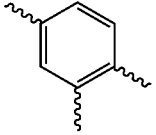 | H | H | H | CF₃ | 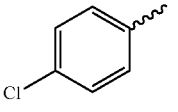 | SO₂ | CH₂ | C=O | Cl |
| AA | 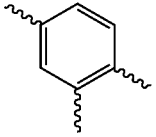 | H | H | H | CF₃ | 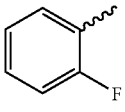 | S | CH₂ | C=O | Cl |
| AB | 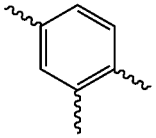 | H | H | H | CH₃ | 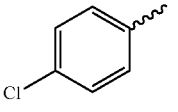 | CH₂ | SO₂ | SO₂ | Cl |

TABLE I-continued

| Cmp | R¹ | R² | R³ | R⁴ | R⁶ | A = | L¹ | L² | L³ | X |
|---|---|---|---|---|---|---|---|---|---|---|
| AC | 3-fluorophenyl | H | H | H | CH₃ | phenyl (1,3) | CH₂ | SO₂ | SO₂ | Cl |
| AD | 4-fluorophenyl | H | H | H | CH₃ | phenyl (1,3) | C=O | SO₂ | SO₂ | Cl |
| AE | H | H | H | H | CF₃ | naphthyl | CB | SO₂ | SO₂ | H |
| AF | H | H | H | H | CH₃ | naphthyl | CB | SO₂ | SO₂ | H |
| AG | 2-fluorophenyl | H | H | H | CH₃ | pyridyl | SO₂ | SO₂ | SO₂ | H |
| AH | Si(CH₃)₃ | H | H | H | CH₃ | phenyl (1,3) | CB | SO₂ | SO₂ | Cl |
| AI | Br | H | H | H | CH₃ | phenyl (1,3) | CB | SO₂ | SO₂ | H |
| AJ | cyclopentyl-C(=O)- | H | H | H | CH₃ | phenyl (1,3) | NH | SO₂ | SO₂ | H |
| AK | C(CH₃)₃ | OCH₃ | H | H | CH₃ | phenyl (1,3) | CO₂ | SO₂ | SO₂ | Cl |

TABLE I-continued

| Cmp | R¹ | R² | R³ | R⁴ | R⁶ | A = | L¹ | L² | L³ | X |
|---|---|---|---|---|---|---|---|---|---|---|
| AL | 2-F-phenyl | CH₃ | H | H | CF₃ | phenyl | SO₂ | SO₂ | SO₂ | Cl |
| AM | 2-F-phenyl | CH₃ | H | H | CH₃ | phenyl | SO₂ | SO₂ | SO₂ | Cl |
| AN | tert-butyl | CH₃ | H | H | CF₃ | phenyl | CO₂ | SO₂ | SO₂ | Cl |
| AO | 2-F-phenyl | H | H | H | CF₃ | indol-2-yl | SO₂ | SO₂ | SO₂ | H |
| AP | tert-butyl | H | H | H | CF₃ | phenyl | CO₂ | SO₂ | SO₂ | OCH₃ |
| AQ | 2-F-phenyl | F | H | H | CF₃ | phenyl | SO₂ | SO₂ | SO₂ | Cl |
| AR | tert-butyl | F | H | H | CF₃ | phenyl | CO₂ | SO₂ | SO₂ | Cl |
| AS | pyridin-2-yl | F | H | H | CF₃ | phenyl | SO₂ | SO₂ | SO₂ | Cl |
| AT | 2-F-phenyl | F | H | H | CF₃ | indol-2-yl | SO₂ | SO₂ | SO₂ | H |

TABLE I-continued

| Cmp | R¹ | R² | R³ | R⁴ | R⁶ | A = | L¹ | L² | L³ | X |
|---|---|---|---|---|---|---|---|---|---|---|
| AU | 2,3-difluorophenyl | F | H | H | CF₃ | phenyl | SO₂ | SO₂ | SO₂ | Cl |
| AV | 2-fluorophenyl | OCH₃ | H | H | CF₃ | phenyl | SO₂ | SO₂ | SO₂ | Cl |
| AW | 2-fluorophenyl | OCH₃ | H | H | CF₃ | phenyl | SO | SO₂ | SO₂ | Cl |
| AX | tert-butyl | OCH₃ | H | H | CF₃ | phenyl | CO₂ | SO₂ | SO₂ | Cl |
| AY | phenyl | H | H | H | CH₃ | phenyl | SO₂ | SO₂ | SO₂ | OCF₃ |
| AZ | 2-fluorophenyl | H | H | H | CF₃ | phenyl | SO₂ | SO₂ | SO₂ | OCF₃ |
| BA | 2-fluorophenyl | H | H | H | CF₃ | phenyl | SO₂ | SO₂ | SO₂ | Cl |
| BB | 4-methoxyphenyl | H | H | H | CF₃ | indole | SO₂ | SO₂ | SO₂ | H |
| BC | 4-methoxyphenyl | H | H | H | CH₃ | indole | SO₂ | SO₂ | SO₂ | H |

TABLE I-continued

| Cmp | R¹ | R² | R³ | R⁴ | R⁶ | A = | L¹ | L² | L³ | X |
|---|---|---|---|---|---|---|---|---|---|---|
| BD | (CH₃)₃C- | H | H | H | CF₃ | phenyl | CO₂ | SO₂ | SO₂ | OCF₃ |
| BE | (F₃C)₂(H₃C)C- | H | H | H | CF₃ | phenyl | CO₂ | SO₂ | SO₂ | Cl |
| BF | 2-F-phenyl | H | CH₃ | CH₃ | CF₃ | phenyl | SO₂ | SO₂ | SO₂ | Cl |
| BG | 2-F-phenyl | H | CH₃ | CH₃ | CF₃ | phenyl | SO₂ | SO₂ | C=O | CF₃ |
| BH | 2-F-phenyl | H | CH₃ | CH₃ | CF₃ | phenyl | SO₂ | SO₂ | C=O | Cl |
| BI | 2-F-phenyl | H | CH₃ | CH₃ | CF₃ | phenyl | SO₂ | SO₂ | SO₂ | CF₃ |
| BJ | 2-F-phenyl | H | CH₃ | CH₃ | H | phenyl | SO₂ | SO₂ | CB | CF₃ |
| BK | (CH₃)₃C- | H | CH₃ | CH₃ | CF₃ | phenyl | CO₂ | SO₂ | SO₂ | Cl |
| BL | 2-F-phenyl | F | H | H | CF₃ | phenyl | SO₂ | SO₂ | SO₂ | CF₃ |

TABLE I-continued

| Cmp | R¹ | R² | R³ | R⁴ | R⁶ | A = | L¹ | L² | L³ | X |
|---|---|---|---|---|---|---|---|---|---|---|
| BM | 2-fluorophenyl | OCH₃ | H | H | CF₃ | phenyl | S | SO₂ | SO₂ | Cl |
| BN | tert-butyl | F | H | H | CF₃ | phenyl | CO₂ | SO₂ | SO₂ | CF₃ |
| BO | 3-fluorophenyl | F | H | H | CF₃ | phenyl | SO₂ | SO₂ | SO₂ | Cl |
| BP | tert-butyl | OH | H | H | CF₃ | phenyl | CO₂ | SO₂ | SO₂ | Cl |
| BQ | tert-butyl | CH₂CH₂CF₃ | H | H | CH₃ | phenyl | CO₂ | SO₂ | SO₂ | Cl |
| BR | pyridine N-oxide | F | H | H | CF₃ | phenyl | SO₂ | SO₂ | SO₂ | Cl |
| BS | tert-butyl | CH₂-cyclopropyl | H | H | CH₃ | phenyl | CO₂ | SO₂ | SO₂ | Cl |
| BT | 2-fluorophenyl | CH₃ | H | H | CF₃ | phenyl | SO₂ | SO₂ | C=O | Cl |
| BU | tert-butyl | CH₂-cyclopropyl | H | H | CF₃ | phenyl | CO₂ | SO₂ | SO₂ | Cl |

TABLE I-continued

| Cmp | R¹ | R² | R³ | R⁴ | R⁶ | A = | L¹ | L² | L³ | X |
|---|---|---|---|---|---|---|---|---|---|---|
| BV | tert-butyl (H₃C)₃C- | OH | H | H | CH₃ | phenyl (meta) | CO₂ | SO₂ | SO₂ | Cl |
| BW | 2-fluorophenyl | F | H | H | CF₃ | phenyl (meta) | SO₂ | SO₂ | C=O | Cl |
| BX | tert-butyl (H₃C)₃C- | C₃H₇ | H | H | CF₃ | phenyl (meta) | CO₂ | SO₂ | SO₂ | Cl |
| BY | 2-(trifluoromethoxy)phenyl | F | H | H | CF₃ | phenyl (meta) | SO₂ | SO₂ | SO₂ | Cl |
| BZ | tert-butyl (H₃C)₃C- | cyclopropylmethyl | H | H | CF₃ | phenyl (meta) | CO₂ | SO₂ | SO₂ | Cl |
| CA | 2,3-difluorophenyl | H | H | H | CF₃ | phenyl (meta) | SO₂ | SO₂ | C=O | Cl |
| CB | 2-fluorophenyl | H | H | H | CF₃ | phenyl | SO₂ | SO₂ | SO₂ | H |
| CC | pyridin-2-yl | H | H | H | CF₃ | phenyl (meta) | SO₂ | SO₂ | SO₂ | Cl |
| CD | 2-fluorophenyl | H | H | H | CF₃ | phenyl (meta) | SO₂ | SO₂ | C=O | Cl |

TABLE I-continued

| Cmp | R¹ | R² | R³ | R⁴ | R⁶ | A = | L¹ | L² | L³ | X |
|---|---|---|---|---|---|---|---|---|---|---|
| CE | 2-fluorophenyl | H | H | H | CF₃ | 1,3-phenylene | SO₂ | SO₂ | C=O | OCF₂H |
| CF | phenyl | H | H | H | CH₃ | 1,2-phenylene | SO₂ | SO₂ | SO₂ | H |
| CG | phenyl | H | H | H | CF₃ | 1,2-phenylene | SO₂ | SO₂ | C=O | H |
| CH | phenyl | H | H | H | CF₃ | 1,3-phenylene | SO₂ | SO₂ | C=O | OCH₃ |
| CI | phenyl | H | H | H | C₂H₅ | 1,3-phenylene | SO₂ | SO₂ | SO₂ | OCF₃ |
| CJ | 2-methylfuran-3-yl | H | H | H | CH₃ | 1,3-phenylene | SO₂ | SO₂ | SO₂ | OCF₃ |
| CK | 2-methylfuran-3-yl | H | H | H | CF₃ | 1,4-phenylene | SO₂ | SO₂ | SO₂ | OCF₃ |
| CL | phenyl | H | H | H | CF₃ | 1,3-phenylene | SO₂ | SO₂ | C=O | OCF₃ |
| CM | 2-fluorophenyl | H | H | H | CF₃ | 1,3-phenylene | SO₂ | SO₂ | C=O | CF₃ |

TABLE I-continued

| Cmp | R¹ | R² | R³ | R⁴ | R⁶ | A = | L¹ | L² | L³ | X |
|---|---|---|---|---|---|---|---|---|---|---|
| CN | 2-fluorophenyl | H | H | H | CF₃ | phenyl (1,3) | SO₂ | SO₂ | C=O | OCF₃ |
| CO | isobutyl | H | H | H | CH₃ | phenyl (1,3) | SO₂ | SO₂ | SO₂ | Cl |
| CP | C₄H₉ | H | H | H | CH₃ | phenyl (1,3) | SO₂ | SO₂ | SO₂ | Cl |
| CQ | tert-butyl | H | H | H | C₂H₅ | phenyl (1,3) | CO₂ | SO₂ | SO₂ | Cl |
| CR | CH₃ | H | H | H | CF₃ | phenyl (1,2) | CO₂ | SO₂ | C=O | H |
| CS | tert-butyl | H | H | H | CF₃ | phenyl (1,3) | CO₂ | SO₂ | SO₂ | CF₃ |
| CT | 2-pyridyl | H | H | H | CF₃ | thiophene (2,5) | CB | SO₂ | C=O | H |
| CU | tert-butyl | H | H | H | CH₃ | thiophene (2,5) | CB | SO₂ | SO₂ | H |
| CV | Cl | H | H | H | CH₃ | thiophene (2,5) | CB | SO₂ | SO₂ | Br |
| CW | 3-isoxazolyl | H | H | H | CH₃ | thiophene (2,5) | CB | SO₂ | SO₂ | H |

TABLE I-continued

Structure: R¹–L¹–A(–X)–L²–N(piperidine with R²)–C(R³)(R⁴)–NH–L³–R⁶

| Cmp | R¹ | R² | R³ | R⁴ | R⁶ | A = | L¹ | L² | L³ | X |
|---|---|---|---|---|---|---|---|---|---|---|
| CX | tert-butyl | F | H | H | CF₃ | 5-(tert-butoxycarbonyl)-1,3-phenylene | CO₂ | SO₂ | C=O | Cl |
| CY | H | H | H | H | CH₃ | naphthalen-1-yl | CB | SO₂ | SO₂ | H |
| CZ | 2-fluorophenyl | H | H | H | CF₃ | 1H-indol-2-yl | SO₂ | C=O | SO₂ | H |
| DA | pyridin-2-yl | F | H | H | CF₃ | 1,3-phenylene | SO | SO₂ | SO₂ | Cl |
| DB | 2-(trifluoromethoxy)phenyl | F | H | H | CF₃ | 1,3-phenylene | SO | SO₂ | SO₂ | Cl |
| DC | 2,6-difluorophenyl | H | H | H | CF₃ | 1,3-phenylene | SO₂ | CH₂ | C=O | OCF₃ |
| DD | CH₃ | H | O* | O* | H | thiophen-2,3-diyl | CO₂ | SO₂ | CB | H |
| DE | pyridin-2-yl | H | H | H | CH₃ | thiophen-2,5-diyl | CB | SO₂ | SO₂ | H |

TABLE I-continued

| Cmp | R¹ | R² | R³ | R⁴ | R⁶ | A = | L¹ | L² | L³ | X |
|---|---|---|---|---|---|---|---|---|---|---|
| DF | phenyl | H | H | H | CH₃ | thiophene | CB | SO₂ | SO₂ | H |
| DG | t-butyl | H | H | H | N(CH₃)₂ | phenyl | CO₂ | SO₂ | SO₂ | Cl |
| DH | Br | H | H | H | CH₃ | phenyl | CB | SO₂ | SO₂ | H |
| DI | CH₃ | H | H | H | CH₃ | phenyl | CB | SO₂ | SO₂ | t-butyl |
| DJ | t-butyl | F | H | H | CF₃ | indole | CO₂ | SO₂ | SO₂ | H |
| DK | pyridyl | OCH₃ | H | H | CF₃ | phenyl | SO₂ | SO₂ | SO₂ | Cl |
| DL | 2-F-phenyl | OC₂H₅ | H | H | H | phenyl | S | SO₂ | CB | Cl |
| DM | 2-F-phenyl | OCH₃ | H | H | CH₃ | phenyl | SO₂ | SO₂ | SO₂ | Cl |
| DN | pyrimidyl | F | H | H | CF₃ | phenyl | SO₂ | SO₂ | SO₂ | Cl |

TABLE I-continued

| Cmp | R¹ | R² | R³ | R⁴ | R⁶ | A = | L¹ | L² | L³ | X |
|---|---|---|---|---|---|---|---|---|---|---|
| DO | 2-fluorophenyl | $OC_2H_5$ | H | H | $CF_3$ | phenyl | $SO_2$ | $SO_2$ | $SO_2$ | Cl |
| DP | pyridinyl | $OCH_3$ | H | H | $CH_3$ | phenyl | $SO_2$ | $SO_2$ | $SO_2$ | Cl |
| DQ | 4-(trifluoromethoxy)phenyl | F | H | H | $CF_3$ | phenyl | $SO_2$ | $SO_2$ | $SO_2$ | Cl |
| DR | piperidinyl | F | H | H | $CF_3$ | phenyl | $SO_2$ | $SO_2$ | $SO_2$ | Cl |
| DS | (CH₃)₃C-NH- | F | H | H | $CF_3$ | phenyl | $SO_2$ | $SO_2$ | $SO_2$ | Cl |
| DT | $CH_3$ | H | H | H | $CH_3$ | phenyl | $SO_2$ | $SO_2$ | $SO_2$ | Cl |
| DU | 2-fluorophenyl | H | H | H | $CF_3$ | indolyl | $SO_2$ | $CH_2$ | $SO_2$ | H |

CB = covalent bond
*R³ and R⁴ taken together form a carbonyl group (C=O).

In a preferred embodiment, representative compounds of the present invention, or a pharmaceutically acceptable salt of the compounds set forth in Table 2 below:

TABLE 2

| Cmp. | R¹ | R² | R⁶ | A | L¹ | X |
|---|---|---|---|---|---|---|
| A | neopentyl (H₃C)₃C-CH₂- | H | $CF_3$ | phenyl | $CO_2$ | Cl |
| C | (CF₃)(CH₃)₂C- | H | $CF_3$ | phenyl | $CO_2$ | Cl |
| D | t-butyl (H₃C)₃C- | H | $CF_3$ | phenyl | $CO_2$ | H |
| E | t-butyl (H₃C)₃C- | H | $CF_3$ | phenyl | $CO_2$ | Cl |
| F | t-butyl (H₃C)₃C- | H | $CH_3$ | phenyl | $CO_2$ | Cl |
| G | cyclobutyl | H | $CF_3$ | phenyl | $CO_2$ | Cl |
| H | i-propyl | H | $CF_3$ | phenyl | $CO_2$ | Cl |
| J | 2-fluorophenyl | H | $CH_3$ | phenyl | $SO_2$ | $OCH_3$ |
| L | 2-fluorophenyl | H | $CH_3$ | phenyl | $SO_2$ | $OCF_2H$ |

TABLE 2-continued

| Cmp. | R¹ | R² | R⁶ | A | L¹ | X |
|---|---|---|---|---|---|---|
| M | 2-F-phenyl | H | $CH_3$ | indole | $SO_2$ | $OCF_3$ |
| N | 2-F-phenyl | H | $C_2H_5$ | phenyl | $SO_2$ | $OCF_2H$ |
| Q | 2-F-phenyl | H | $CF_3$ | phenyl | $SO_2$ | $CF_3$ |
| AK | tert-butyl | $OCH_3$ | $CH_3$ | phenyl | $CO_2$ | Cl |
| AL | 2-F-phenyl | $CH_3$ | $CF_3$ | phenyl | $SO_2$ | Cl |
| AM | 2-F-phenyl | $CH_3$ | $CH_3$ | phenyl | $SO_2$ | Cl |
| AN | tert-butyl | $CH_3$ | $CF_3$ | phenyl | $CO_2$ | Cl |
| AO | 2-F-phenyl | H | $CF_3$ | indole | $SO_2$ | H |
| AP | tert-butyl | H | $CF_3$ | phenyl | $CO_2$ | $OCH_3$ |

TABLE 2-continued

| Cmp. | R¹ | R² | R⁶ | A | L¹ | X |
|---|---|---|---|---|---|---|
| AQ | 2-fluorophenyl | F | $CF_3$ | 1,3-phenylene | $SO_2$ | Cl |
| AR | tert-butyl | F | $CF_3$ | 1,3-phenylene | $CO_2$ | Cl |
| AS | 2-pyridyl | F | $CF_3$ | 1,3-phenylene | $SO_2$ | Cl |
| AT | 2-fluorophenyl | F | $CF_3$ | indol-2-yl | $SO_2$ | H |
| AU | 2,3-difluorophenyl | F | $CF_3$ | 1,3-phenylene | $SO_2$ | Cl |
| AV | 2-fluorophenyl | $OCH_3$ | $CF_3$ | 1,3-phenylene | $SO_2$ | Cl |
| AW | 2-fluorophenyl | $OCH_3$ | $CF_3$ | 1,3-phenylene | SO | Cl |
| AX | tert-butyl | $OCH_3$ | $CF_3$ | 1,3-phenylene | $CO_2$ | Cl |
| AZ | 2-fluorophenyl | H | $CF_3$ | 1,3-phenylene | $SO_2$ | $OCF_3$ |

TABLE 2-continued
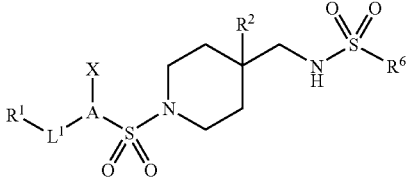
| Cmp. | R¹ | R² | R⁶ | A | L¹ | X |
|---|---|---|---|---|---|---|
| BB | 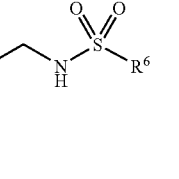 | H | $CF_3$ | 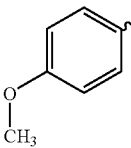 | $SO_2$ | H |
| BD | 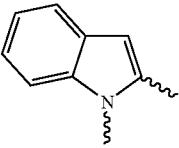 | H | $CF_3$ | 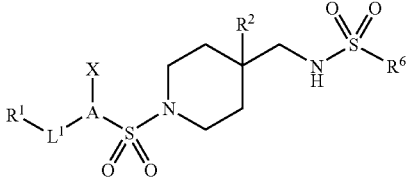 | $CO_2$ | $OCF_3$ |
| BE | 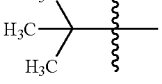 | H | $CF_3$ | 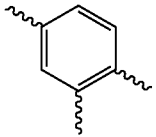 | $CO_2$ | Cl |
| DK | 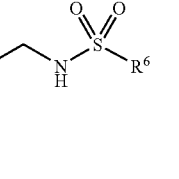 | $OCH_3$ | $CF_3$ | 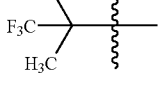 | $SO_2$ | Cl |
| DM | 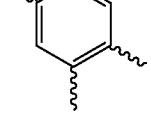 | $OCH_3$ | $CH_3$ | 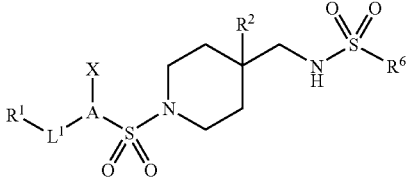 | $SO_2$ | Cl |
| DO | 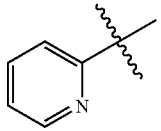 | $OC_2H_5$ | $CF_3$ | 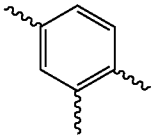 | $SO_2$ | Cl |
| DP | 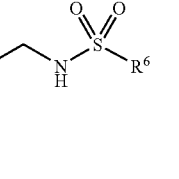 | $OCH_3$ | $CH_3$ | 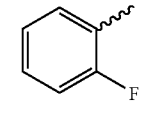 | $SO_2$ | Cl |
| EF | 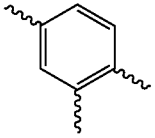 | H | $CH_3$ | 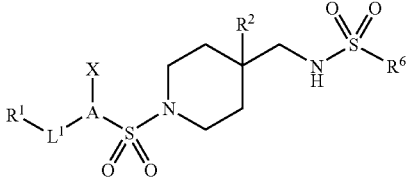 | $SO_2$ | $OCH3$ |

TABLE 2-continued

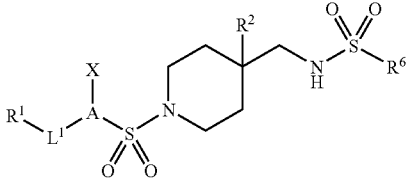

| Cmp. | R¹ | R² | R⁶ | A | L¹ | X |
|---|---|---|---|---|---|---|
| EG | 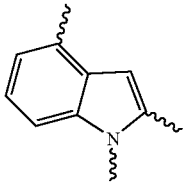 | H | CH₃ | 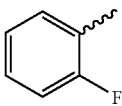 | SO₂ | OH |
| EH | 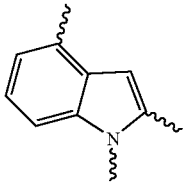 | F | CF₃ |  | SO₂ | OCH3 |
| EI | 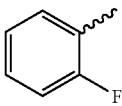 | CH₃ | CF₃ | 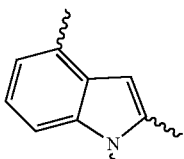 | SO₂ | H |
| FG |  | H | CF₃ | 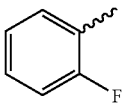 | SO₂ | H |
| FH | 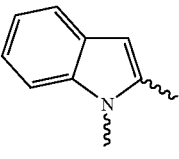 | CH₃ | CF₃ |  | SO₂ | H |

Spectral Data for selected Compounds in Table 2

Compound A

¹H NMR (300 MHz, CDCl₃) δ7.77 (d, J=8.4 Hz, 1H), 7.56 (dd, J=8.4, 2.4 Hz, 1H), 7.46 (d, J=2.4 Hz, 1H), 5.20 (t, J=6.3 Hz, 1H), 4.05 (s, 2H), 3.90 (br d, J=12.3 Hz, 2H), 3.19 (t, J=6.6 Hz, 2H), 2.59 (dd, J=12.3, 2.4 Hz, 2H), 1.81 (br d, J=12.6 Hz, 2H), 1.52-1.68 (m, 1H), 1.20-1.40 (m, 2H), 1.01 (s, 9H).

Compound C

¹H NMR (300 MHz, CDCl₃) δ7.75 (d, J=7.2 Hz, 1H), 7.60 (dd, J=7.2, 2.1 Hz, 1H), 7.44 (d, J=2.1 Hz, 1H), 5.19 (t, J=6.3 Hz, 1H), 3.85 (d, J=12.3 Hz, 2H), 3.19 (t, J=6.3 Hz, 2H), 2.55 (td, J=12.3, 2.4 Hz, 2H), 2.04 (s, 6H), 1.80 (br d, J=12.9 Hz, 2H), 1.52-1.72 (m, 1H), 1.22-1.44 (m, 2H).

Compound D

¹H NMR (300 MHz, CDCl₃) S7.77 (d, J=7.8 Hz, 1H), 7.50-7.65 (m, 2H), 7.44 (dd, J=7.8, 1.2 Hz, 1H), 5.15 (t, J=6.0 Hz, 1H), 3.95 (br d, J=12.0 Hz, 2H), 3.17 (t, J=6.3 Hz, 2H), 2.56 (t, J=12.0 Hz, 2H), 1.80 (d, J=12.0 Hz, 2H), 1.61 (s, 9H), 1.49-1.72 (m, 1H), 1.22-1.42 (m, 2H).

Compound E

¹H NMR (300 MHz, CDCl₃) δ7.73 (d, J=8.6 Hz, 1H), 7.50 (dd, J=8.6, 2.1 Hz, 1H), 7.41 (d, J=2.1 Hz, 1H), 4.95 (t, J=6 Hz, 1H), 3.93 (br d, J=12.3 Hz, 2H), 3.18 (t, J=6.3 Hz, 2H), 2.59 (td, J=12.3, 2.4 Hz, 2H), 1.82 (br d, J=12.6 Hz, 2H), 1.61 (s, 9H), 1.19-1.42 (m, 3H).

Compound F $^1$H NMR (300 MHz, CDCl$_3$) δ7.72 (d, J=8.4 Hz, 1H), 7.50 (dd, J=8.4, 2.3 Hz, 1H), 7.41 (d, J=2.3 Hz, 1H), 4.26 (t, J=6.3 Hz, 1H), 3.92 (br d, J=12.4 Hz, 2H), 3.03 (t, J=6.3 Hz, 2H), 2.96 (s, 3H), 2.59 (td, J=12.4, 2.3 Hz, 2H), 1.83 (br d, J=12.6 Hz, 2H), 1.61 (s, 9H), 1.50-1.64 (m, 1H), 1.22-1.42 (m, 2H).

Compound G $^1$H NMR (300 MHz, CDCl$_3$) δ7.74 (d, J=8.4 Hz, 1H), 7.51 (dd, J=8.4, 2.1 Hz, 1H), 7.42 (d, J=2.1 Hz, 1H), 5.15 (m, 1H), 4.22 (quint, J=2.4 Hz, 1H), 3.90 (br d, J=12.6 Hz, 2H), 3.17 (d, J=6.6 Hz, 2H), 2.57 (dd, J=12.6, 2.4 Hz, 2H), 1.81 (br d, J=12.9 Hz, 2H), 1.34-1.74 (m, 9H).

Compound H $^1$H NMR (300 MHz, CDCl$_3$) δ7.74 (d, J=8.4 Hz, 1H), 7.53 (dd, J=8.4, 2.1 Hz, 1H), 7.44 (d, J=2.1 Hz, 1H), 5.18-5.34 (m, 2H), 3.90 (br d, J=12.6 Hz, 2H), 3.17 (d, J=6.6 Hz, 2H), 2.57 (dd, J=12.6, 2.4 Hz, 2H), 1.81 (br d, J=12.9 Hz, 2H), 1.49-1.68 (m, 1H), 1.39 (d, J=6.3 Hz, 6H), 1.20-1.40 (m, 2H).

Compound J $^1$H NMR (300 MHz, CDCl$_3$) δ8.10-8.24 (m, 2H), 8.00 (d, J=9 Hz, 1H), 7.54-7.66 (m, 1H), 7.37 (t, J=9 Hz, 1H), 7.17-7.22 (m, 1H); 7.06-7.07 (m, 1H); 4.30-4.48 (m, 1H); 3.98 (s, 3H); 3.90-3.98 (m, 2H); 2.97-3.04 (m, 2H); 2.95 (s, 3H); 2.60-2.76 (m, 2H); 1.72-1.86 (m, 2H); 1.50-1.70 (m, 1H); 1.20-1.38 (m, 2H)

Compound L $^1$H NMR (300 MHz, CDCl$_3$) δ8.22 (t, J=2.7 Hz, 1H), 7.97 (td, J=7.7, 1.8 Hz, 1H), 7.90 (d, J=8.7 Hz, 1H), 7.38-7.48 (m, 1H), 7.31 (dd, J=8.7, 2.4 Hz, 1H), 7.18 (td, J=6.6, 1.2 Hz, 1H), 6.91 (td, J=8.8, 1.2 Hz, 1H), 6.31 (t, J$_{H-F}$=54 Hz, 1H), 4.41 (t, J=6.3 Hz, 1H), 3.79 (d, J=12.9 Hz, 2H), 2.83 (t, J=6.6 Hz, 2H), 2.77 (s, 3H), 2.56 (td, J=12.9, 2.4 Hz, 2H), 1.63 (br d, J=10.8 Hz, 2H), 1.38-1.57 (m, 1H), 1.02-1.20 (m, 2H).

Compound M $^1$H NMR (300 MHz, CDCl$_3$) δ8.52 (s, 1H), 8.07-8.21 (m, 2H), 7.57-7.68 (m, 2H), 7.38 (t, J=7.5 Hz, 1H), 7.09 (t, J=8.4 Hz, 1H), 4.58 (t, J=6.3 Hz, 1H), 4.00 (d, J=12.7 Hz, 2H), 3.02 (t, J=6.7 Hz, 2H), 2.98 (s, 3H), 2.78 (t, J=12.7 Hz, 2H), 1.82 (br d, J=10.2 Hz, 2H), 1.18-1.40 (m, 3H).

Compound N $^1$H NMR (300 MHz, CDCl$_3$) δ8.22 (t, J=2.4 Hz, 1H), 7.99 (td, J=7.5, 1.5 Hz, 1H), 7.90 (d, J=8.7 Hz, 1H), 7.38-7.45 (m, 1H), 7.30 (dd, J=8.7, 1.8 Hz, 1H), 7.15 (td, J=7.8, 2.4 Hz, 1H), 6.90 (td, J=9.6, 1.0 Hz, 1H), 6.55 (t, J$_{H-F}$=72 Hz, 1H), 4.32 (t, J=6.6 Hz, 1H), 3.78 (d, J=12.5 Hz, 2H), 2.78-2.90 (m, 4H), 2.55 (td, J=12.5, 2.1 Hz, 2H), 1.63 (br d, J=10.8 Hz, 2H), 1.38-1.54 (m, 1H), 1.17 (t, J=7.2 Hz, 3H), 1.00-1.20 (m, 2H).

Compound Q $^1$H NMR (300 MHz, CDCl$_3$) δ8.96 (s, 1H), 8.21 (d, J=7.5 Hz, 1H), 8.17 (d, J=7.5 Hz, 1H), 8.02 (d, J=7.5 Hz, 1H), 7.58-7.69 (m, 1H), 7.32-7.42 (m, 1H), 7.09 (d, J=7.8 Hz, 1H), 6.33 (br s, 1H), 4.02 (br d, J=12.1 Hz, 2H), 3.30 (t, J=6.5 Hz, 2H), 2.80 (t, J=12.1 Hz, 2H), 1.66-1.83 (m, 3H), 1.20-1.42 (m, 2H).

Compound AK $^1$H NMR (300 MHz, CDCl$_3$) δ7.71 (d, J=8.3 Hz, 1H), 7.49 (dd, J=8.7, 2.1 Hz, 1H), 7.39 (d, J=2.1 Hz, 1H), 4.37 (t, J=5.7 Hz, 1H), 3.59 (m, 2H), 3.13 (d, J=4.9 Hz, 2H), 3.12 (s, 3H), 2.97 (s, 3H), 2.93 (m, 2H), 1.92 (m, 2H), 1.60 (s, 9H), 1.57 (m, 2H).

Compound AL $^1$H NMR (300 MHz, CD$_3$OD) δ8.54 (t, J=2 Hz, 1H), 8.08 (td, J=8, 2 Hz, 1H), 8.00 (d, J=8 Hz, 1H), 7.92 (dd, J=8, 2 Hz, 1H), 7.63-7.77 (m, 1H), 7.41 (t, J=8 Hz, 1H), 7.21 (t, J=8 Hz, 1H), 3.30-3.42 (m, 2H), 3.10 (ddd, J=13, 11, 4 Hz, 2H), 2.83 (br s, 2H), 1.48-1.62 (m, 2H), 1.23-1.41 (m, 2H), 0.89 (s, 3H).

Compound AM $^1$H NMR (300 MHz, CDCl$_3$) δ8.66 (t, J=2 Hz, 1H), 8.15 (td, J=8, 2 Hz, 1H), 8.02 (d, J=8 Hz, 1H), 7.95 (dd, J=8, 2 Hz, 1H), 7.57-7.66 (m, 1H), 7.36 (t, J=7.5 Hz, 1H), 7.09 (t, J=7.5 Hz, 1H), 4.29 (t, J=7 Hz, 1H), 3.58 (ddd, J=14, 6, 6 Hz, 2H), 3.46 (d, J=7.5 Hz, 1H), 3.41 (d, J=7.5 Hz, 1H), 3.08 (ddd, J=14, 11, 4 Hz, 2H), 2.96 (s, 3H), 1.52-1.62 (m, 2H), 1.21-1.36 (m, 2H), 0.98 (s, 3H).

Compound AN $^1$H NMR (300 MHz, CDCl$_3$) δ7.74 (d, J=8 Hz, 1H), 7.54 (dd, J=8, 2 Hz, 1H), 7.41 (d, J=2 Hz, 1H), 5.10 (br s, 1H), 3.52 (ddd, J=12, 6, 6 Hz, 2H), 3.04-3.14 (m, 2H), 3.00 (ddd, J=12, 11, 4 Hz, 2H), 1.61 (s, 9H), 1.40-1.62 (m, 4H), 0.97 (s, 3H).

Compound AO $^1$H NMR (300 MHz, CDCl$_3$) δ8.25 (d, J=9.3 Hz, 1H), 8.03 (dt, J=1.6, 7.0 Hz, 1H), 7.64 (d, J=8 Hz, 1H), 7.51-7.60 (m, 2H), 7.47 (b, 1H), 7.37 (t, J=7.7 Hz, 1H), 7.28 (t, J=7.7 Hz, 1H), 7.05 (t, J=9.6 Hz, 1H), 5.6 (b, 1H), 3.95 (d, J=13 Hz, 2H), 3.19 (d, J=6.6 Hz, 2H), 2.84 (t, J=11.5 Hz, 2H), 1.81 (d, J=13.3 Hz, 2H), 1.70 (m, 1H), 1.35 (dt, J=4.0 Hz, 11.6 Hz, 2H)

Compound AP $^1$H NMR (300 MHz, CDCl$_3$) δ7.71 (d, J=9 Hz, 1H), 7.00 (dd, J=9, 2.7 Hz, 1H), 6.88 (dd, J=2.7 Hz, 1H), 5.16 (t, J=6 Hz, 1H), 3.93 (brd, J=12 Hz, 2H), 3.90 (s, 3H), 3.19 (d, J=6.3 Hz, 1H), 3.17 (d, J=6.3 Hz, 1H), 2.56 (ddd, J=12.3, 12.1, 2.4 Hz, 2H), 1.80 (br d, J=11.7 Hz, 2H), 1.61 (s, 9H), 1.50-1.61 (m, 1H), 1.22-1.41 (m, 2H).

Compound AQ $^1$H NMR (300 MHz, CDCl$_3$) δ8.66 (t, J=2.4 Hz, 1H), 8.07 (td, J=8, 1 Hz, 1H), 8.05 (d, J=8.4 Hz, 1H), 7.74 (dd, J=8.4, 2.4 Hz, 1H), 7.59-7.68 (m, 1H), 7.37 (td, J=8, 1 Hz, 1H), 7.10 (td, J=8, 1 Hz, 1H), 5.07 (t, J=6.3 Hz, 1H), 3.81-3.97 (m, 2H), 3.45 (d, J=6.3 Hz, 1H), 3.38 (d, J=6.3 Hz, 1H), 3.11 (ddd, J=10.5, 10.5, 3 Hz, 2H), 1.97-2.07 (m, 2H), 1.62-1.88 (m, 2H).

Compound AR $^1$H NMR (300 MHz, CDCl$_3$) δ7.71 (d, J=8.7 Hz, 1H), 7.51 (dd, J=8.7, 2.1 Hz, 1H), 7.42 (d, J=2.1 Hz, 1H), 5.16 (t, J=6.8 Hz, 1H), 3.78-3.88 (m, 2H), 3.44 (d, J=6.8 Hz, 1H), 3.37 (d, J=6.8 Hz, 1H), 2.94 (ddd, J=11.2, 11.2, 3 Hz, 2H), 1.97-2.07 (m, 2H), 1.64-1.89 (m, 2H), 1.62 (s, 9H).

Compound AS $^1$H NMR (300 MHz, CDCl$_3$) δ8.69 (d, J=2.1 Hz, 1H), 8.50-8.55 (m, 1H), 8.19 (d, J=8 Hz, 1H), 8.02 (d, J=8 Hz, 1H), 7.94-8.05 (m, 1H), 7.77 (dd, J=2.4, 8.0 Hz, 1H), 7.45-7.55 (m, 1H), 5.13 (t, J=6.6 Hz, 1H), 3.83-3.93 (m, 2H), 3.41 (dd, J=6.0, 20 Hz, 2H), 3.01-3.11 (m, 2H), 1.83-2.05 (m, 2H), 1.62-1.85 (m, 2H)

Compound AT $^1$H NMR (300 MHz, CDCl$_3$) δ8.26 (d, J=8.8 Hz, 1H), 8.04 (dt, J=1.8, 7.5 Hz, 1H), 7.65 (d, J=8.2 Hz, 1H), 7.49-7.61 (m, 3H), 7.38 (t, J=7.5 Hz, 1H), 7.29 (t, J=8.2 Hz, 1H), 7.06 (t, J=8.9 Hz, 1H), 5.43 (t, J=6.3 Hz, 1H), 3.87 (d, J=15 Hz, 2H), 3.43 (dd, J=6.3 Hz, 20 Hz, 2H), 3.2 (dt, J=2.8 Hz, 12.3 Hz, 2H), 2.0 (dt, J=2.9 Hz, 12.1 Hz, 2H), 1.80 (m, 2H).

Compound AU $^1$H NMR (300 MHz, CDCl$_3$) δ8.58 (dd, J=1.2 Hz, J=1.2 Hz, 1H), 8.05 (dd, J=8.4 Hz, J=1.15 Hz, 1H), 7.76 (dd, J=8.4 Hz, J=2.2 Hz, 1H), 7.48-7.6 (m, 1H), 5.34 (t, J=6.5 Hz, 2H), 3.9 (dt, J=13.7 Hz, J=2.5 Hz, 2H), 3.4 (dd, J=20.5 Hz, J=6.3 Hz, 2H), 3.12 (dt, J=12.9 Hz, J=2.6 Hz, 2H), 2.04-1.91 (m, 2H), 1.88-1.6 (m, 2H).

Compound AV $^1$H NMR (300 MHz, CDCl$_3$) δ8.66 (t, J=2.3 Hz, 1H), 8.13 (m, 1H), 8.02 (d, J=8.4 Hz, 1H), 7.74 (dd, J=8.3, 2.2 Hz, 1H), 7.61 (m, 1H), 7.36 (t, J=7.8 Hz, 1H), 7.09 (m, J=9.5 Hz, 1H), 5.17 (b, 1H), 3.69 (m, 2H), 3.27 (d, J=2.9 Hz, 2H), 3.16 (s, 3H), 3.09 (m, 2H), 1.92 (m, 2H), 1.57 (m, 2H).

Compound AW $^1$H NMR (300 MHz, CDCl$_3$) δ8.37 (s, 1H), 7.83 (d, J=8.4 Hz, 1H), 7.66 (dd, J=2.1 Hz, 8.4 Hz, 1H), 7.50 (m, 1H), 7.40 (m, 1H), 7.25 (t, J=8.0 Hz, 1H), 7.16 (t, J=8.7 Hz, 1H), 5.00 (b, 1H), 3.65 (m, 1H), 3.54 (m, 1H), 3.28 (t, J=6.6 Hz, 2H), 3.14 (s, 3H), 2.88 (m, 2H), 1.94 (m, 2H), 1.60 (m, 2H).

Compound AX $^1$H NMR (300 MHz, CDCl$_3$) δ7.72 (d, J=8.8 Hz, 1H), 7.49 (dd, J=8.6 Hz, 2.1 Hz, 1H), 7.39 (d, J=2.1 Hz, 1H), 5.04 (d, 1H), 3.59 (m, 2H), 3.25 (s, 2H), 3.12 (s, 3H), 2.94 (m, 2H), 1.91 (m, 2H), 1.59 (s, 9H), 1.58 (m, 2H).

Compound AZ $^1$H NMR (300 MHz, CDCl$_3$) δ 8.52 (s, 1H), 8.15-8.25 (m, 2H), 7.82 (d, J=8.7 Hz, 1H), 7.56-7.71 (m, 1H), 7.32-7.50 (m, 1H), 7.02-7.19 (m, 1H), 5.07 (s, 1H), 4.01 (br d, J=12.9 Hz, 2H), 3.20 (t, J=6.3 Hz, 2H), 2.79 (td, J=12.9, 2.4 Hz, 2H), 1.83 (s, 2H), 1.22-1.50 (m, 3H).

Compound BB $^1$H NMR (300 MHz, CDCl$_3$) δ8.28 (dd, J=1 Hz, 8.6 Hz, 1H), 8 (td, J=2 Hz, 9 Hz, 2H), 7.59 (td, J=1 Hz, 8 Hz, 1H), 7.52 (td, J=1.4 Hz, 8 Hz, 1H), 7.48 (d, J=1 Hz, 1H), 7.33 (dt, J=1.2 Hz, 7.7 Hz, 1H), 6.86 (td, J=2.2 Hz, 9.2 Hz, 2H), 5.17 (b, 1H), 4.01 (d, J=13 Hz, 2H), 3.79 (s, 3H), 3.23 (d, J=7 Hz, 2H), 2.91 (dt, J=2.6 Hz, 13, 2H), 1.83 (d, J=13 Hz, 2H), 1.72 (m, 1H), 1.41 (dt, J=3.5 Hz, 13 Hz, 2H)

Compound BD $^1$H NMR (300 MHz, CDCl$_3$) δ7.82 (d, J=8.2 Hz, 1H), 7.37 (dd, J=8.2, 2.3 Hz, 1H), 7.23 (d, J=2.3 Hz, 1H), 6.63 (br s, 1H), 3.92 (d, J=12.4 Hz, 2H), 3.24 (t, J=6.3 Hz, 2H), 2.60 (td, J=12.4, 2.3 Hz, 2H), 1.78 (br d, J=12.6 Hz, 2H), 1.63 (s, 9H), 1.20-1.47 (m, 3H).

Compound BE $^1$H NMR (300 MHz, CDCl$_3$) δ7.76 (d, J=7.2 Hz, 1H), 7.61 (dd, J=7.2, 2.1 Hz, 1H), 7.44 (d, J=2.1 Hz, 1H), 5.19 (t, J=6.3 Hz, 1H), 3.89 (d, J=12.3 Hz, 2H), 3.18 (t, J=6.3 Hz, 2H), 2.57 (td, J=12.3, 2.4 Hz, 2H), 2.16 (s, 3H), 1.82 (br d, J=12.9 Hz, 2H), 1.50-1.71 (m, 1H), 1.20-1.41 (m, 2H).

Compound DK $^1$H NMR (300 MHz, CDCl$_3$) δ8.68 (d, J=2.26 Hz, 1H), 8.51 (m, 1H), 8.18 (d, J=7.9 Hz, 1H), 7.98 (m, 2H), 7.76 (dd, J=8.4, 2.1 Hz, 1H), 7.48 (m, 1H), 5.28 (b, 1H), 3.67 (m, 2H), 3.26 (s, 2H), 3.14 (s, 3H), 3.04 (m, 2H), 1.90 (m, 2H), 1.54 (m, 2H).

Compound DM $^1$H NMR (300 MHz, CDCl$_3$) δ 8.66 (t, J=2.33 Hz, 1H), 8.14 (td, J=7.5 Hz, 1.8 Hz, 1H), 8.01 (d, J=8.6 Hz, 1H), 7.74 (dd, J=8.6 Hz, 2.3 Hz, 1H), 7.61 (m, 1H), 7.36 (t, J=8.1 Hz, 1H), 7.09 (t, J=9.0 Hz, 1H), 4.47 (t, J=5.7 Hz, 1H), 3.69 (m, 1H), 3.16 (s, 3H), 3.15 (d, J=6.3 Hz, 2H), 3.09 (m, 2H), 2.99 (s, 3H), 1.93 (m, 2H), 1.57 (m, 2H).

Compound DO $^1$H NMR (300 MHz, CDCl$_3$) δ 8.66 (t, J=2.4 Hz, 1H), 8.14 (m, 1H), 8.04 (d, J=8.6 Hz, 1H), 7.74 (dd, J=8.4 Hz, 2.3 Hz, 1H), 7.62 (m, 1H), 7.36 (t, J=8.0 Hz, 1H), 7.10 (t, J=9.2 Hz, 1H), 5.03 (b, 1H), 3.68 (m, 2H), 3.33 (q, J=7.1 Hz, 2H), 3.28 (s, 2H), 3.14 (m, 2H), 1.92 (m, 2H), 1.58 (m, 2H), 1.19 (t, J=7.1 Hz, 3H).

Compound DP $^1$H NMR (300 MHz, CDCl$_3$) δ 8.69 (d, J=2.3 Hz, 1H), 8.52 (m, 1H), 8.19 (d, J=8.0 Hz, 1H), 7.97 (m, 2H), 7.76 (dd, J=2.4 Hz, 8.6 Hz, 1H), 7.48 (m, 1H), 4.46 (t, J=6.5 Hz, 1H), 3.68 (m, 2H), 3.15 (s, 3H), 3.13 (d, J=6.1 Hz, 2H), 3.04 (m, 2H), 2.98 (s, 3H), 1.91 (m, 2H), 1.55 (m, 2H).

Compound EG $^1$H NMR (CDCl$_3$) δ 7.99 (t, J=8 Hz, 1H), 7.72 (d, J=9 Hz, 1H), 7.59 (s, 1H), 7.53 (m, 2H), 7.32-7.19 (m, 2H), 7.04 (t, J=9 Hz, 1H), 6.73 (d, J=8 Hz, 1H), 6.42 (b, 1H), 4.68 (m, 1H), 3.89 (d, J=14 Hz, 2H), 3.0 (t, J=7 Hz, 2H), 2.94 (s, 3H), 2.81 (t, J=12 Hz, 2H), 1.78 (t, J=12 Hz, 2H), 1.64 (b, 1H), 1.28 (m, 2H).

The compounds of the present invention exhibit anti-inflammatory and/or immunomodulatory activity and are useful in the treatment of various medical conditions including, e.g., rheumatoid arthritis, systemic lupus erythematosus, multiple sclerosis, glaucoma, diabetes, osteoporosis, renal ischemia, cerebral stroke, cerebral ischemia, nephritis, psoriasis, allergy, inflammatory disorders of the lungs and gastrointestinal tract such as Crohn's disease, and respiratory tract disorders such as reversible airway obstruction, asthma, chronic obstructive pulmonary disease (COPD) and bronchitis. This utility is manifested as demonstrated by activity in the following assay.

Potential cannabinoid receptor ligands were screened for the ability to compete with [$^3$H] CP-55,940 for binding to recombinant cannabinoid receptors. Test compounds were serially diluted in Diluent Buffer (50 mM Tris pH 7.1, 1 mM EDTA, 3 mM MgCl$_2$, 0.1% BSA, 10% DMSO, 0.36% methyl cellulose (Sigma M-6385)) from stocks prepared in 100% DMSO. Aliquots (10 μL) were transferred into 96-well microtiter plates. Membrane preparations of recombinant human cannabinoid CB2 receptor (Receptor Biology #RB-HCB2) or recombinant human cannabinoid CB1 receptor (Receptor Biology #RB-HCB1) were diluted to 0.3 mg/mL in Binding Buffer (50 mM Tris pH 7.2, 1 mM EDTA, 3 mM MgCl$_2$, 0.1% BSA). Aliquots (50 μL) were added to each well of the microtiter plate. The binding reactions were initiated by addition of [$^3$H] CP-55,940 (New England Nuclear # NET 1051; specific activity=180 Ci/mmol) to each well of the microtiter plate. Each 100 μl reaction mixture contained 0.48 nM [$^3$H] CP-55,940, 15 μg membrane protein in binding buffer containing 1% DMSO and 0.036% methyl cellulose. Following incubation for 2 hours at room temperature, the reactions were filtered through 0.5% polyethylenimine-coated GF/C filter plates (UniFilter-96, Packard) with a TomTec Mark 3U Harvester (Hamden, Conn.). The filter plate was washed 5 times with binding buffer, rotated 180°, then re-washed 5 times with binding buffer. Bound radioactivity was quantitated following addition of 30 μl of Packard Microscint 20 scintillant in a Packard TopCount NXT microplate scintillation counter. Non-linear regression analysis of the resulting data was performed using Prism 2.0b (GraphPad, San Diego, Calif.).

Compounds of the present invention were found to exhibit CB2 receptor binding activity in the range of 0.1 to 1000 nM.

The present invention also relates to a pharmaceutical composition comprising a compound of formula I of this invention and a pharmaceutically acceptable carrier. The compounds of formula I can be administered in any conventional dosage form known to those skilled in the art. Pharmaceutical compositions containing the compounds of formula I can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like. All routes of administration are contemplated including, but not limited to, parenteral, transdermal, subcutaneous, intramuscular, sublingual, inhalation, rectal and topical.

Thus, appropriate unit forms of administration include oral forms such as tablets, capsules, powders, cachets, granules and solutions or suspensions, sublingual and buccal forms of administration, aerosols, implants, subcutaneous, intramuscular, intravenous, intranasal, intraocular, subcutaneous or rectal forms of administration.

When a solid composition is prepared in the form of tablets, e.g., a wetting agent such as sodium lauryl sulfate can be added to micronized or non-micronized compounds of formula I and mixed with a pharmaceutical vehicle such as silica, gelatin starch, lactose, magnesium stearate, talc, gum arabic or the like. The tablets can be coated with sucrose, various polymers, or other appropriate substances. Tablets can be treated so as to have a prolonged or delayed activity and so as to release a predetermined amount of active principle continuously or at predetermined intervals, e.g., by using ionic resins and the like.

A preparation in the form of gelatin capsules may be obtained, e.g., by mixing the active principle with a diluent, such as a glycol or a glycerol ester, and incorporating the resulting mixture into soft or hard gelatin capsules.

A preparation in the form of a syrup or elixir can contain the active principle together, e.g., with a sweetener, methylparaben and propylparaben as antiseptics, flavoring agents and an appropriate color.

Water-dispersible powders or granules can contain the active principle mixed, e.g., with dispersants, wetting agents or suspending agents, such as polyvinylpyrrolidone, as well as with sweeteners and/or other flavoring agents.

Rectal administration may be provided by using suppositories which may be prepared, e.g., with binders melting at the rectal temperature, for example cocoa butter or polyethylene glycols.

Parenteral, intranasal or intraocular administration may be provided by using, e.g., aqueous suspensions, isotonic saline solutions or sterile and injectable solutions containing pharmacologically compatible dispersants and/or solubilizers, for example, propylene glycol or polyethylene glycol.

Thus, to prepare an aqueous solution for intravenous injection, it is possible to use a co-solvent, e.g., an alcohol such as ethanol or a glycol such as polyethylene glycol or propylene glycol, and a hydrophilic surfactant such as Tween® 80. An oily solution injectable intramuscularly can be prepared, e.g., by solubilizing the active principle with a triglyceride or a glycerol ester.

Topical administration can be provided by using, e.g., creams, ointments or gels.

Transdermal administration can be provided by using patches in the form of a multilaminate, or with a reservoir, containing the active principle and an appropriate solvent.

Administration by inhalation can be provided by using, e.g., an aerosol containing sorbitan trioleate or oleic acid, for example, together with trichlorofluoromethane, dichlorofluoromethane, dichlorotetrafluoroethane or any other biologically compatible propellant gas; it is also possible to use a system containing the active principle, by itself or associated with an excipient, in powder form.

The active principle can also be formulated as microcapsules or microspheres, e.g., liposomes, optionally with one or more carriers or additives.

Implants are among the prolonged release forms which can be used in the case of chronic treatments. They can be prepared in the form of an oily suspension or in the form of a suspension of microspheres in an isotonic medium.

The daily dose of a compound of formula I for treatment of a disease or condition cited above is about 0.001 to about 100 mg/kg of body weight per day, preferably about 0.001 to about 10 mg/kg. For an average body weight of 70 kg, the dosage level is therefore from about 0.1 to about 700 mg of drug per day, given in a single dose or 2-4 divided doses. The exact dose, however, is determined by the attending clinician and is dependent on the potency of the compound administered, the age, weight, condition and response of the patient.

Compounds of the present invention can be can be used in combination with disease modifying antirheumatic agents described herein above, the administration and dosage of such agents is as according to the schedule listed in the product information sheet of the approved agents, in the Physicians Desk Reference (PDR) as well as therapeutic protocols well known in the art.

Compounds of the present invention can be can be used in combination with H1 antagonists described herein above, the administration and dosage of such agents is as according to the schedule listed in the product information sheet of the approved agents, in the Physicians Desk Reference (PDR) as well as therapeutic protocols well known in the art.

Compounds of the present invention can be can be used in combination with compounds useful in the treatment of multiple sclerosis described herein above, the administration and dosage of such agents is as according to the schedule listed in the product information sheet of the approved agents, in the *Physicians Desk Reference* (PDR) as well as therapeutic protocols well known in the art.

Compounds of the present invention can be can be used in combination with compounds useful in the treatment of psoriasis described herein above, the administration and dosage of such agents is as according to the schedule listed in the product information sheet of the approved agents, in the Physicians Desk Reference (PDR) as well as therapeutic protocols well known in the art.

Compounds of the present invention can be can be used in combination with compounds useful in the treatment of psoriasis described herein above, the administration and dosage of such agents is as according to the schedule listed in the product information sheet of the approved agents, in the Physicians Desk Reference (PDR) as well as therapeutic protocols well known in the art.

It will be apparent to those skilled in the art that the administration of the agents used in combination with the compounds of the present invention can be varied depending on the disease being treated and the known effects of the agents on that disease. Also, in accordance with the knowledge of the skilled clinician, the therapeutic protocols (e.g. dosage amounts and times of administration) can be varied in view of the observed effects of the administered agents on the patients, and in view of the observed responses of the disease to the administered agents.

The following examples illustrate the preparation of some of the compounds of the invention and are not to be construed as limiting the invention disclosed herein. Alternate mechanistic pathways and analogous structures will be apparent to those skilled in the art.

EXAMPLE I

Compound 1

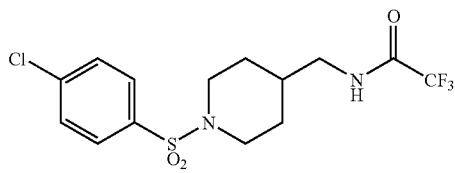

Step 1. A mixture of 4-(trifluoroacetamidomethyl)piperidinium trifluoroacetate (16.1 g, 49.6 mmol) and triethylamine (15 mL, 11 g, 109 mmol) in $CH_2Cl_2$ (100 mL) was cooled to 0° C. and a solution of p-chlorobenzenesulfonyl chloride (11.5 g, 54.5 mmol) in $CH_2Cl_2$ (100 mL) was added dropwise by cannula over 5 min. The ice bath was removed and the reaction was allowed to proceed for 18 h at rt. The reaction mixture was poured into water. The layers were separated and the aq. layer was extracted with $CH_2Cl_2$. The combined organic layers were washed with brine, dried over $MgSO_4$, and filtered. The solvent was evaporated to afford 16.8 g (96%) of Compound 1.

Compound 2

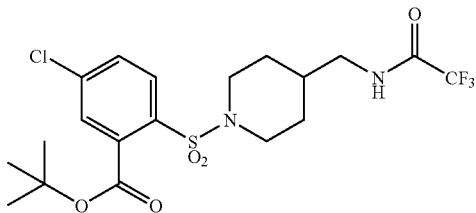

Step 2. n-BuLi (9.8 mL, 1.7 M in hexane, 17 mmol) was added dropwise over 10 min to a solution of Compound 1 (4.92 g, 14.0 mmol) in THF (100 mL) at −78° C. The resulting orange-yellow solution was stirred at −78° C. for 30 min. A solution of di-t-butyl dicarbonate (3.7 g, 17 mmol) in THF (40 mL) was added by cannula and the reaction mixture was stirred at −78° C. for 5 h. The reaction mixture was partitioned between water (200 mL) and EtOAc (200 mL). The aq. layer was extracted again with EtOAc. The combined organic layers were washed with brine, dried over $MgSO_4$, and filtered. The solvent was evaporated to yield 5.54 g (82%) of Compound 2.

Compound 3

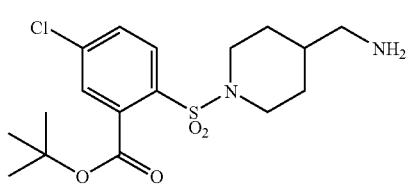

Step 3. Compound 2 (5.54 g, 11.4 mmol) was dissolved in MeOH (110 mL).

A solution of potassium carbonate (11.1 g, 80.0 mmol) in water (100 mL) was added and the reaction mixture was stirred at rt for 12 h. The solvent was removed under reduced pressure and the resulting white paste was diluted with water (~20 mL) and extracted with EtOAc (3×100 mL). The combined organic extracts were washed with brine, dried over $MgSO_4$, and filtered. The solvent was evaporated to yield 3.41 g (84%) of Compound 3.

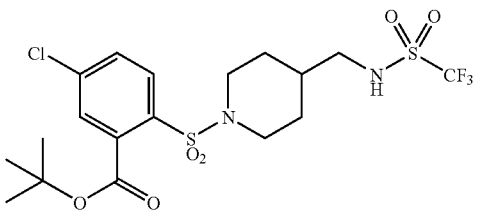

Step 4. Compound E A solution of Compound 3 (3.14 g, 8.80 mmol) and triethylamine (2.5 mL, 1.8 g, 18 mmol) in $CH_2Cl_2$ (90 mL) was cooled to −78° C. and a solution of trifluoromethanesulfonic anhydride (1.6 mL, 2.7 g, 9.7 mmol) in $CH_2Cl_2$ (10 mL) was added dropwise over 5 min. The reaction mixture was stirred at −78° C. for 1 h, then poured into saturated aq $NaHCO_3$ solution. The organic layer was withdrawn and the aq. layer was extracted with EtOAc. The combined organic layers were washed with brine, dried over $MgSO_4$, and filtered. Solvent was evaporated to afford an oil. Further purification by sgc (4:1 hexane-EtOAc) afforded 2.545 g (56%) of Compound 4 (E).

EXAMPLE II

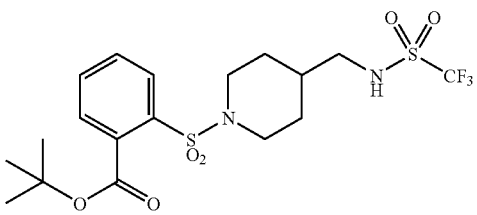

Compound I. Compound 4, from Example I, step 4 (65 mg, 0.12 mmol) was dissolved in MeOH (1 mL) and palladium(II) hydroxide on carbon (4 mg, 20 wt % Pd, 0.006 mmol) was added. The reaction mixture was stirred under hydrogen atmosphere (ambient pressure) for 15 h, then filtered through a short pad of silica gel, eluting with EtOAc. The solvent was removed to provide a clear film, which was purified by sgc (2:1 hexane-EtOAc) to yield 55 mg (91%) of Compound 5(I).

EXAMPLE III

Compound 6

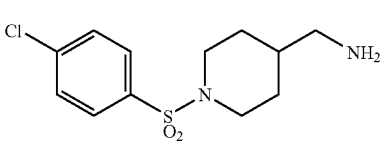

Step 1. To a solution of Compound 1 (34.6 g, 93 mmol) in MeOH (1800 mL) was added a solution of potassium carbonate (90 g, 650 mmol) in water (700 mL). The solution was stirred at rt for 18 h. The solvent was evaporated and the residue was partitioned between EtOAc (500 mL) and water (1000 mL). The organic layer was withdrawn, and the aq. layer was extracted further with EtOAc (5×200 mL). The combined organic layers were dried over MgSO₄ and then filtered. Solvent was removed under reduced pressure to yield 21.5 g (80%) of Compound 6.

Compound 7

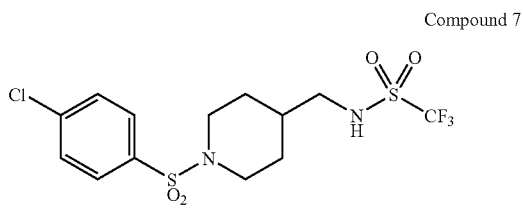

Step 2. A solution of Compound 6 above (21.5 g, 77.6 mmol) and triethylamine (32 mL, 24 g, 233 mmol) in CH₂Cl₂ (350 mL) was cooled to −78° C. and a solution of trifluoromethanesulfonic anhydride (22 g, 78 mmol) in CH₂Cl₂ (250 mL) was added dropwise over 2 h. The reaction mixture was stirred for a further 2 h at −78° C., then diluted with CH₂Cl₂ (500 mL). The organic solution was washed with 1 N HCl, water, and brine, then dried over MgSO₄, and filtered. Solvent was evaporated to afford 28.3 g (87%) of Compound 7.

Compound 8

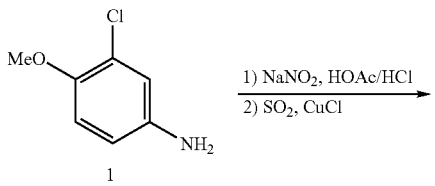

Step 3. n-BuLi (4.7 mL, 2.5 M in hexane, 12 mmol) was added dropwise over 10 min to a solution of Compound 7 (2.33 g, 5.55 mmol) in THF (50 mL) at −78° C. The resulting solution was stirred at −78° C. for 30 min. A solution of bis(2-fluorophenyl) disulfide (1.4 g, 5.5 mmol) in THF (40 mL) was added by cannula and the reaction mixture was stirred at −78° C. for 5 h, and then allowed to warm to rt over 12 h. The reaction mixture was neutralized with saturated aq NaHSO₄ solution and was partitioned between water (200 mL) and EtOAc (200 mL). The aq. layer was extracted again with EtOAc. The combined organic layers were washed with brine, dried over MgSO₄, and filtered. The solvent was evaporated to a solid. After purification by sgc (2:1 hexane-EtOAc), 2.52 g (83%) of Compound 8 was obtained.

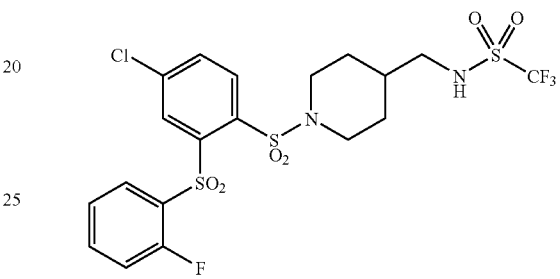

Step 4. Compound BA Compound 8 (1.42 g, 2.59 mmol) was dissolved in dry CH₂Cl₂ (25 mL) and cooled to 0° C. Solid MCPBA (3.58 g, ~50 wt %. 1.79 g, 10.4 mmol) was added portionwise. The resulting suspension was stirred at 0° C. for 5 min and at rt for 18 h. The reaction mixture was diluted with CH₂Cl₂ (~500 mL) and washed successively with saturated aq NaHCO₃, water, and brine, dried over MgSO₄, and filtered. Evaporative removal of the solvent afforded a solid that was purified by sgc (2:1 hexanes-EtOAc) to yield 1.34 g (89%) of Compound 9.

Compound 9A

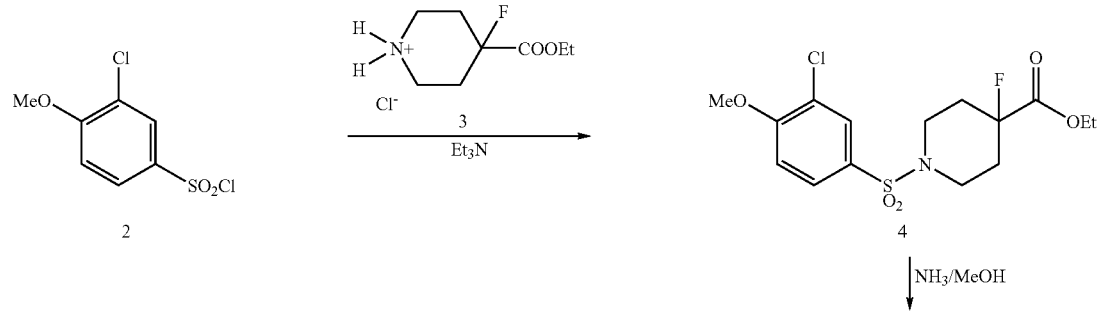

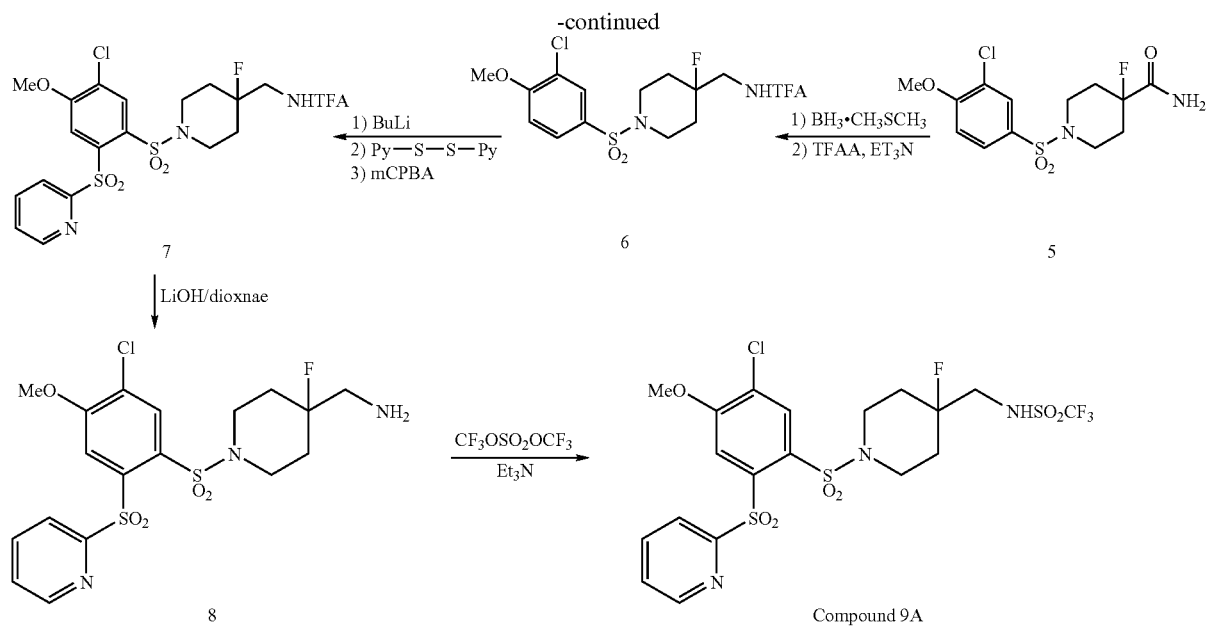

Compound 2: Compound 1 (4.82 g, 30.6 mmol) was dissolved in HOAc (60 mL) at 0° C. Then HCl (con. 40 mL) was added followed by addition of NaNO₂ (6.33 g, 92 mmol) in H₂O (40 mL). This mixture was stirred at 0° C. for 30 min. Meanwhile in another container SO₂ was bubbled into HOAc (100 mL) at 0° C. for 40 min. CuCl (cat.) was added to this mixture followed by addition of the diazonium salt. The reaction was stirred at 0° C. for 1.5 h. The reaction mixture was poured into ice (500 g) and stirred for 1.5 h. The solid was collected by suction filtration. The solid was dissolved in CH₂Cl₂ (50 mL) and washed by brine. The organic layer was separated and dried over Na₂SO₄, and concentrated to dryness to give 4 g (54%) crude compound 2 as a yellow solid.

Compound 4: Compound 2 (2.41 g, 10 mmol) was dissolved in CH₂Cl₂ (10 mL) at room temperature. Compound 3 (2.1 g, 10 mmol) was added followed by addition of triethylamine (5.6 mL, 40 mol). The mixture was stirred at rt for 0.5 h. It was extracted with brine (30 mL). The organic layer was dried over Na₂SO₄, and concentrated to dryness. The crude product was purified with via sgc (33% EtOAc/hexanes) to give 3.2 (84%) compound 4 as a white powder.

Compound 5: Compound 4 (3.2 g, 8.44 mmol) was suspended in an ammonia solution (30 mL; 7N in MeOH) and was stirred at rt for 24 h. The solvent was removed under reduced pressure to afford 2.96 g (100%) compound 5 as white solid.

Compound 6: Borane-methyl sulfide complex (2.85 mL, 10 M in THF, 28.5 mmol) was added to a suspension of Compound 5 (2.96 g, 8.44 mmol) in THF (30 mL). The reaction mixture was stirred at reflux for 3 h, then cooled to 0° C. Concentrated HCl (2 mL) was added dropwise. The pH of the solution was adjusted tp neutrality was addition of 1 M of NaOH (~15 mL). The mixture was diluted with EtOAc (~30 mL) and water (100 mL). The organic layer was separated and dried over Na₂SO₄ and concentrated to dryness. This material (1.86 g, 5.52 mmol) was dissolved in CH₂Cl₂ (30 mL) and cooled to −78° C. Et₃N (1.92, 13.9 mmol) was added followed by the addition of TFAA (0.78 mL, 5.52 mmol). The reaction mixture was stirred for 1.5 h before warming up to 0° C. Brine (15 mL) was added and the product was extracted with CH₂Cl₂ (50 mL). The organic layer was dried over Na₂SO₄ and concentrated to dryness. The crude product was purified via sgc (50% EtOAc/hexanes) to give 507 mg (16%) compound 6 as a white solid.

Compound 7: In a flame dried flask under N₂ blanket, compound 6 (507 mg, 1.17 mmol) was dissolved in dry THF (30 mL) and cooled to −78° C. n-Butyl lithium (2.0 M in hexanes, 1.23 mL, 2.46 mmol) was added followed after 45 min by pyridine disulfide (258 mg, 1.17 mmol). The cold bath was removed after 2 h and the reaction mixture was allowed to warm to rt over 45 minutes then quenched with aq NH₄Cl. EtOAc (30 mL) was added to dilute the reaction. The reaction mixture was washed with brine (100 mL×2). The organic layer was dried over Na₂SO₄ and then concentrated to dryness. The crude material was dissolved in CH₂Cl₂ (30 mL) and HOAc (1 mL) and cooled to 0° C. MCPBA (2.4 g, ca 1.38 mmol) was added. The ice bath was removed and the reaction mixture was stirred at rt overnight. Aqueous NaHCO₃ (200 mL) and CH₂Cl₂ were added and the layers were separated. The organic layer was washed with aq NaHSO₃, NaHCO₃, H₂O, and brine then dried with Na₂SO₄. The crude product is purified by sgc (50% EtOAc/hexanes) to give 210 mg (31%) of compound 7 as a white solid.

Compound 8: Compound 7 (205 mg, 0.36 mmol) was dissolved in dioxane (8 mL) at room temperature. LiOH (1.0 M, 8.0 mL, 8.0 mmol) was added and the mixture was stirred at room temperature for overnight. The solvent was removed and CH₂Cl₂ (15 mL) and brine (15 mL) was added and the layers were separated. The aqueous layer was extracted with additional CH₂Cl₂ (15 mL) and the combined organic layers were dried over Na₂SO₄ and concentrated to dryness to give compound 8 (170 mg, 99%) as a white powder.

Compound 9A: Compound 8 (76 mg, 0.16 mmol) was dissolved in CH₂Cl₂ (15 mL) and cooled to −78° C. Et₃N (40 mg, 0.4 mmol) was added followed by the addition of trifluoromethanesulfonic anhydride (45 mg, 0.16 mmol). The reaction mixture was stirred for 30 min before warming up to 0° C. Brine (15 mL) was added and the product was extracted with CH₂Cl₂ (15 mL). The organic layer was dried over Na₂SO₄ and concentrated to dryness. The crude product was purified via PTLC (33% EtOAc/hexanes) to give 47 mg (47%) Compound 9A as a white solid.

EXAMPLE IV

Compound 10

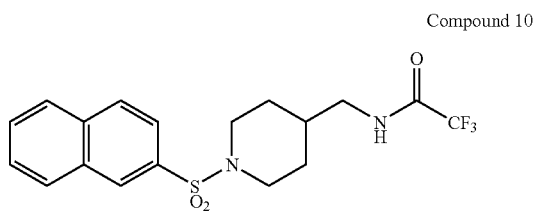

Step 1. A mixture of 4-(trifluoroacetamidomethyl)piperidinium trifluoroacetate (500 mg, 1.54 mmol) and triethylamine (470 μL, 343 mg, 3.39 mmol) in CH$_2$Cl$_2$ (1 mL) was cooled to 0° C. and a solution of 2-naphthalenesulfonyl chloride (350 mg, 1.54 mmol) in CH$_2$Cl$_2$ (0.5 mL) was added in one portion by cannula. The ice bath was removed and the reaction was allowed to proceed for 16 h at rt. The reaction mixture was diluted with CH$_2$Cl$_2$ and washed successively with 1 N HCl, water, and brine. The organic phase was dried over MgSO$_4$ and filtered. Evaporation of the solvent afforded an oil that was then purified by sgc (1:1 hexanes-EtOAc) to give 532 mg (86%) of Compound 10.

Compound 11

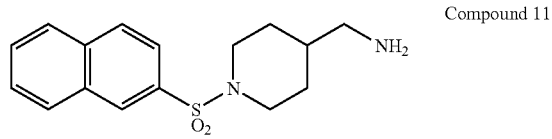

Step 2. Compound 10 (299 mg, 0.745 mmol) was dissolved in MeOH (4 mL) and THF (4 mL) and a solution of potassium carbonate (721 mg, 5.22 mmol) in water (2 mL) was added. The solution was stirred at rt for 15 h. The solvent was evaporated under reduced pressure and the aq. residue was partitioned between EtOAc (~50 mL) and water (~25 mL). The organic layer was washed with brine, dried over MgSO$_4$, and filtered. Evaporation of the solvent provided 125 mg (55%) of product.

Compound 12

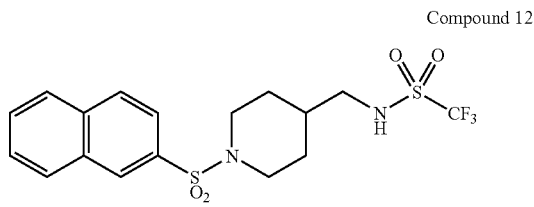

Step 3. A solution of Compound 11 (62 mg, 0.202 mmol) and triethylamine (42 μL, 31 mg, 0.303 mmol) in CH$_2$Cl$_2$ (200 μL) was cooled to 0° C. and trifluoromethanesulfonic anhydride (34 μL, 57 mg, 0.202 mmol) was added. The ice bath was removed and the reaction was allowed to proceed for 12 h at rt. The reaction mixture was diluted with CH$_2$Cl$_2$ and washed successively with 1 N HCl, water, and brine. The organic phase was dried over MgSO$_4$ and filtered. Evaporation of the solvent afforded a solid that was then purified by sgc (1:1 hexanes-EtOAc) to give 25 mg (29%) of Compound 12.

EXAMPLE V

Compound 13

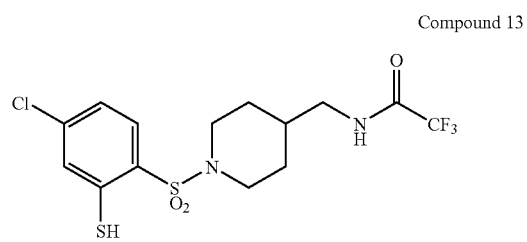

Step 1. A solution of Compound 1 (10.0 g, 28.5 mmol) in THF (150 mL) was cooled to −78° C. and MeLi (22 mL, 1.0 M in THF-cumene, 31 mmol) was added dropwise over ~5 min. n-BuLi (20 mL, 2.5 M in hexane, 31 mmol) was added dropwise over ~5 min, and the resulting solution was stirred at −78° C. for 30 min. Sulfur powder (1.095 g, 34 mmol) was added in one portion. The reaction mixture was stirred at −78° C. for 1 h and then at rt for 18 h. The reaction mixture was poured into saturated aq. NH$_4$Cl solution (~500 mL) and diluted with EtOAc (500 mL). The aq layer was extracted with another portion of EtOAc (~250 mL). The combined extracts were washed with brine, dried over MgSO$_4$, and filtered. Removal of solvent gave a syrup. Purification by sgc (1:1 hexanes-EtOAc) afforded 7.23 g (61%) of Compound 13.

Compound 14

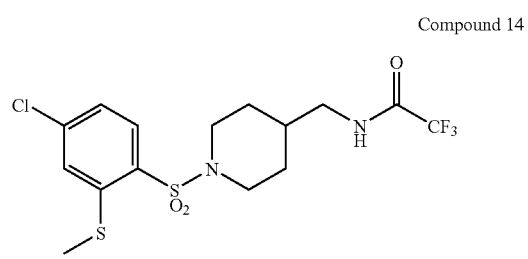

Step 2. To a suspension of sodium hydride (78 mg, 60% dispersion in oil, 2.0 mmol) in THF (2 mL) at 0° C. was added, dropwise by cannula over 5 min, a solution of Compound 13 (628 mg, 1.51 mmol) in THF (13 mL). The solution was stirred at 0° C. for 30 min. Iodomethane (122 mL, 278 mg, 2.0 mmol) was added in one portion and the reaction mixture was stirred at 0° C. for 5 min and then at rt for 15 h. The reaction mixture was diluted with EtOAc and poured into brine. The organic layer was withdrawn, dried over MgSO$_4$, and filtered. Evaporation of the solvent provided an oil. Purification by sgc (3:1 hexanes-EtOAc) gave 432 mg (67%) of Compound 14 as a viscous syrup.

Compound 15

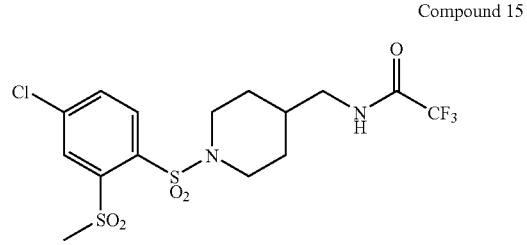

Step 3. To a solution of Compound 14 (424 mg, 0.983 mmol) in CH$_2$Cl$_2$ (5 mL) at 0° C. was added MCPBA (615 mg, ~70 wt %, 431 mg, 2.50 mmol) in one portion. The reaction mixture was stirred at 0° C. for 1 min, then at rt for 16 h. The reaction mixture was diluted with EtOAc, then washed successively with saturated aq. NaHCO$_3$ and brine. The organic layer was dried over MgSO$_4$ and filtered. Evaporation of the solvent, followed by purification of the resulting oil by sgc (5:3 hexanes-EtOAc) gave 272 mg (60%) of Compound 15.

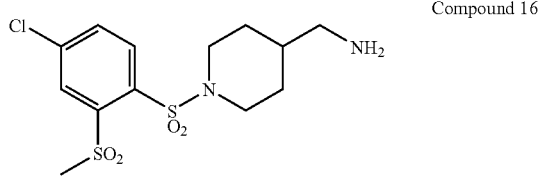

Compound 16

Step 4. Solid potassium carbonate (342 mg, 2.47 mmol) was added to a solution of Compound 15 (229 mg, 0.494 mmol) in MeOH (5 mL) and water (1.5 mL). The reaction mixture was stirred at rt for 16 h, then diluted with EtOAc (40 mL), and washed with water (20 mL). The organic phase was washed with brine, dried over MgSO$_4$, and filtered. Evaporation of the solvent afforded 148 mg (83%) of Compound 16.

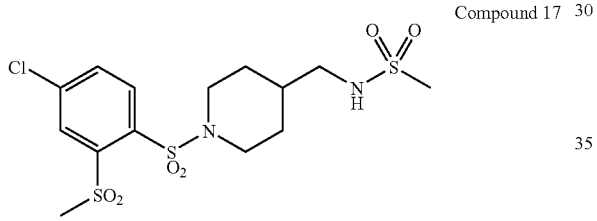

Compound 17

Step 5. Compound DT A solution of Compound 16 (66 mg, 0.18 mmol) and triethylamine (33 µL, 27 mg, 0.24 mmol) in CH$_2$Cl$_2$ (450 µL) was cooled to 0° C. and MsCl (18 µL, 27 mg, 0.24 mmol) was added dropwise. The solution was stirred at 0° C. for 2 min and then at rt for 2 h. The reaction mixture was diluted with EtOAc and washed successively with water and brine. The organic phase was dried over MgSO$_4$ and filtered. Removal of the solvent afforded a solid that was then purified by sgc (1:1 hexanes-EtOAc) to yield 59 mg (74%) of Compound 17(DT).

EXAMPLE VI

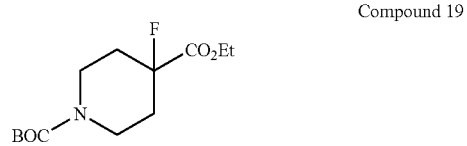

Compound 18

Step 1. To a solution of ethyl isonipecotate (50 g, 0.318 mol) in CH$_2$Cl$_2$ (150 mL) at 0° C. was added a solution of di-t-butyl dicarbonate (73 g, 0.334 mol) in CH$_2$Cl$_2$ (150 mL) over 15 min. The ice bath was removed and the reaction mixture was stirred at rt for 12 h. The solvent was evaporated to yield a liquid. Subsequent purification by sgc (4:1 hexanes-Et$_2$O) gave 80 g (98%) of Compound 18.

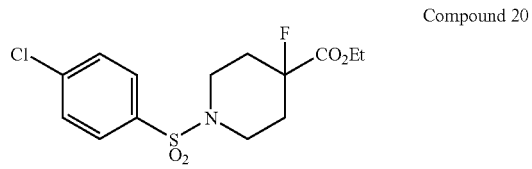

Compound 19

Step 2. To a solution of LDA (233 mL, 2.0 M in THF/heptane/ethylbenzene, 0.466 mol) in THF (300 mL) at 0° C. was added, dropwise over 1.0 h, a solution of Compound 18 (100 g, 0.389 mol) in THF (~400 mL). The solution was stirred at 0° C. for 30, and then transferred by cannula to a pre-cooled (0° C.) solution of N-fluorobenzenesulfonimide (153 g, 0.485 mol) in dry THF (~600 mL). The reaction mixture was stirred at 0° C. for 30 min, and then at rt for 18 h. The total solvent volume was reduced to approximately one third, and EtOAc (~1 L) was added. The solution was washed successively with water, 0.1 N aq. HCl, water, saturated aq. NaHCO$_3$, and brine. The organic layer was dried over MgSO$_4$, filtered, and concentrated under reduced pressure to yield a crude liquid. Separation by sgc (6:1 hexanes-EtOAc) gave 93.5 g (87%) of Compound 19.

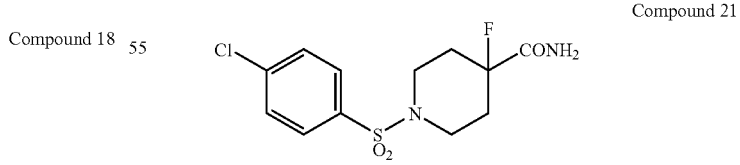

Compound 20

Step 3. To Compound 19 (182 g, 0.66 mol) was added HCl (800 mL, 4.0 M in dioxane). The solution was stirred at rt for 12 h, after which the solvent was removed under reduced pressure to afford a solid. The solid was redissolved in CH$_2$Cl$_2$ (1 L) and triethylamine (275 mL, 200 g, 1.97 mol) was added. The reaction mixture was cooled to 0° C., and a solution of p-chlorobenzenesulfonyl chloride (139 g, 0.66 mol) in CH$_2$Cl$_2$ (500 mL) was added over 10 min. The ice bath was removed and the reaction was allowed to proceed at rt for 3 h. The reaction mixture was diluted with CH$_2$Cl$_2$ (1 L) and washed successively with 1 N HCl, water, and brine. The organic layer was dried over MgSO$_4$ and then filtered. Evaporation of the solvent afforded 163 g (71% over two steps) of Compound 20.

Compound 21

Step 4. Compound 20 (30 g, 86 mmol) was suspended in an ammonia solution (1 L; 7 N in MeOH) and was stirred at rt for 24 h. The solvent was removed under reduced pressure to afford a solid. CH$_2$Cl$_2$ (500 mL) was added, and then removed under reduced pressure to yield 28.7 g (100%) of Compound Compound 22

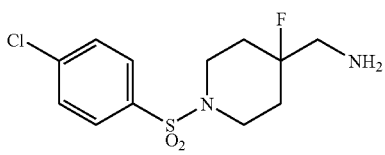

Step 5. Borane-methyl sulfide complex (25 mL, 10 M in THF, 250 mmol) was added to a suspension of Compound 21 (15.0 g, 46.7 mmol) in THF (200 mL). The reaction mixture was stirred at reflux for 3 h, then cooled to 0° C. THF (500 mL) was added. Concentrated hydrochloric acid (13 mL) was added dropwise over 45 min. The pH of the solution was adjusted to neutrality via addition of 0.5 M NaOH solution (~350 mL). The mixture was diluted with EtOAc (~500 mL) and water (1 L). The organic layer was separated and the aq. layer extracted again with EtOAc (2×500 mL). The combined extracts were washed with brine (1×1 L), dried over MgSO$_4$, and filtered. The solvent was evaporated to give 10.6 g (74%) of Compound 22.

Compound 23

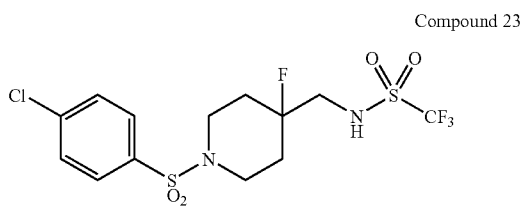

Step 6. To a solution of Compound 22 (10.6 g, 34.6 mmol) and triethylamine (15 mL, 11 g, 104 mmol) in CH$_2$Cl$_2$ (300 mL) at −78° C. was added, dropwise over 30 min, a solution of trifluoromethanesulfonic anhydride (5.8 mL, 9.8 g, 35 mmol) in CH$_2$Cl$_2$ (100 mL). The solution was stirred at −78° C. for 3 h, then diluted with CH$_2$Cl$_2$ (300 mL), and washed successively with 1 N HCl, water, and brine. The organic phase was dried over MgSO$_4$ and filtered. Removal of the solvent under reduced pressure afforded a solid that was purified by sgc (3:1 hexanes-EtOAc) to give 6.3 g (42%) of Compound 23.

Compound 24

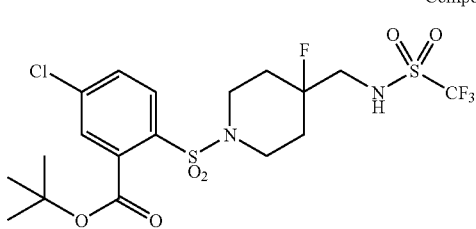

Step 7. Compound AR To a solution of Compound 23 (1.6 g, 3.7 mmol) in THF (30 mL) at −78° C. was added n-BuLi (3.2 mL, 2.5 M in hexane, 8.0 mmol). The reaction mixture was stirred at −78° C. for 1 h, after which a solution of di-t-butyl dicarbonate (1.6 g, 7.3 mmol) in THF (10 mL) was added. The reaction was allowed to proceed for 4 h. Dilute HCl (50 mL, 1.0 M) was added, and the solution was extracted with EtOAc. The organic phase was washed successively with 1 N NaHCO$_3$ and brine, dried over MgSO$_4$, and filtered. Removal of solvent afforded a clear paste that was purified by sgc (3:1 hexanes-EtOAc) to give 1.28 g (65%) of Compound 24 (AR).

EXAMPLE VII

Compound 25

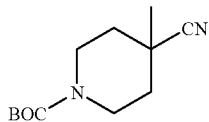

Step 1. To a solution of 1-(t-butoxycarbonyl)-4-cyanopiperidine (1.05 g, 5.00 mmol) in THF (15 mL) at −78° C. was added a solution of LDA (3.0 mL, 2.0 M in THF/cumene/ethylbenzene, 6.0 mmol). The resulting solution was stirred at −78° C. for 30 min. Iodomethane (0.4 mL, 6 mmol) was added. The reaction mixture was allowed to warm to rt, and was stirred at rt for 18 h. The reaction mixture was diluted with EtOAc and washed successively with 1 N HCl, 1 M aq NaHCO$_3$, and brine. The organic layer was dried over Na$_2$SO$_4$ and filtered. Removal of solvent afforded an oily residue that was purified by sgc (4:1 hexanes-EtOAc) to give 1.05 g (94%) of Compound 25.

Compound 26

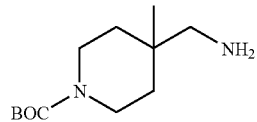

Step 2. A mixture of Compound 25 (1.00 g, 4.46 mmol) and Rh/Al$_2$O$_3$ catalyst (300 mg, 5 wt %, 0.14 mmol) in methanolic ammonia solution (15 mL, ~3.5 N NH$_3$ in MeOH) was shaken under hydrogen atmosphere (~40 psi). The solution was filtered through a silica gel pad, and the filtrate was concentrated to give 1.00 g (98%) of Compound 26.

Compound 27

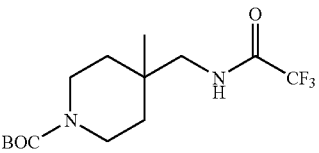

Step 3. To a solution of Compound 26 (2.0 g, 8.8 mmol) and triethylamine (5.0 mL, 3.6 g, 36 mmol) in CH$_2$Cl$_2$ at 0° C. was added TFAA (1.5 mL, 2.2 g, 11 mmol). The reaction mixture was allowed to warm to rt, and was stirred for 18 h. The reaction mixture was diluted with CH$_2$Cl$_2$ and washed successively with 1 N HCl, water, 1 M aq NaHCO$_3$, and brine. The organic layer was dried over Na$_2$SO$_4$ and filtered. Removal of the solvent gave 2.8 g (100%) of Compound 27.

Compound 28

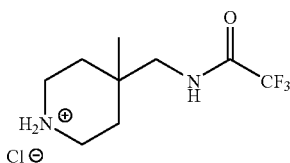

Step 4. A mixture of Compound 27 (2.8 g, 8.8 mmol) and hydrogen chloride solution (20 mL, 4.0 M in dioxane) was stirred at rt for 15 h. Evaporation of the solvent gave 2.3 g (100%) of Compound 28.

Compound 29

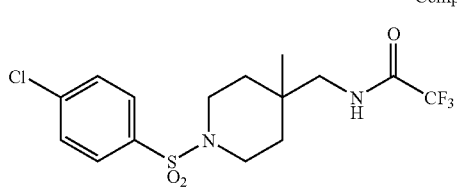

Step 5. To a solution of Compound 28 (1.30 g, 5.00 mmol) and triethylamine (5.0 mL, 3.6 g, 36 mmol) was added p-chlorobenzenesulfonyl chloride (1.06 g, 5.02 mmol). The reaction mixture was stirred at rt for 18 h, then diluted with $CH_2Cl_2$, and washed successively with 1 N HCl, 1 M aq $NaHCO_3$, and brine. The organic layer was dried over $Na_2SO_4$ and filtered. Evaporation of the solvent afforded a solid that was then purified by sgc (0.5% MeOH in $CH_2Cl_2$) to give 1.8 g (90%) of Compound 29.

Compound 30

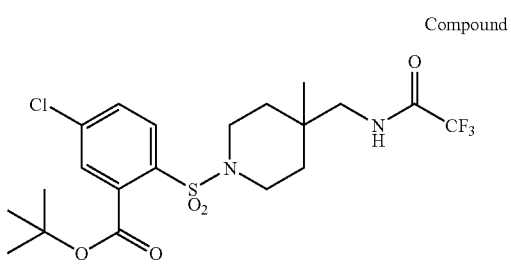

Step 6. To a solution of Compound 29 (420 mg, 1.06 mmol) in THF (10 mL) at −78° C. was added n-BuLi (1.5 mL, 1.6 M in hexanes, 2.4 mmol). The solution was stirred at −78° C. for 30 min. A solution of di-t-butyl dicarbonate (220 mg, 1.01 mmol) in THF (2 mL) was added. The reaction mixture was allowed to warm to rt, and was stirred for 18 h. The reaction mixture was diluted with EtOAc and washed with water and brine, dried over $Na_2SO_4$, and filtered. Evaporation of the solvent gave a crude solid that was then purified by sgc (3:1 hexanes-EtOAc) to give 530 mg (100%) of Compound 30.

Compound 31

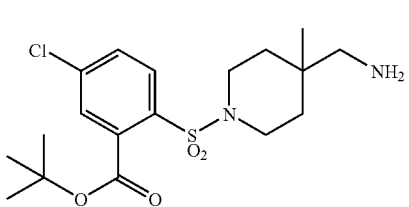

Step 7. To a solution of Compound 30 (530 mg, 1.06 mmol) in MeOH (20 mL) was added a solution of potassium carbonate (1.5 g, 11 mmol) in water (8 mL). The reaction mixture was stirred at rt for 18 h. The solvent was evaporated and the residue was partitioned between EtOAc and water. The aq. layer was extracted further with EtOAc. The combined extracts were washed with brine, dried over $Na_2SO_4$, and filtered. Evaporation of the solvent gave 350 mg (87%) of Compound 31.

Compound 32

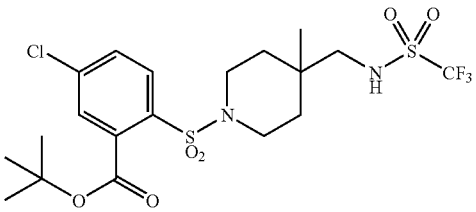

Step 8. Compound AN To a solution of Compound 31 (300 mg, 0.75 mmol) and triethylamine (2 mL, 1.5 g, 14 mmol) in $CH_2Cl_2$ (10 mL) at −78° C. was added a solution of trifluoromethanesulfonic anhydride (0.15 mL, 0.25 g, 0.089 mmol) in $CH_2Cl_2$ (5 mL). The reaction mixture was stirred at −78° C. for 2 h, then diluted with $CH_2Cl_2$, and washed successively with 1 N HCl, 1 M aq. $NaHCO_3$, and brine. The organic layer was dried over $MgSO_4$ and filtered. Evaporation of the solvent yielded a solid that was purified by sgc (3:1 hexane-EtOAc) to give 270 mg (67%) of Compound 32 (AN).

EXAMPLE VIII

Compound 33

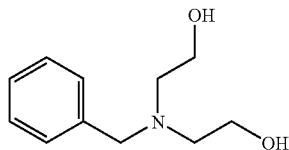

Step 1. Benzyl chloride (62.7 g, 0.496 mol) and diethanolamine (167.1 g, 1.589 mol) were dissolved in ethanol (115 mL, Pharmco 190 proof) and heated to 100° C. The reaction mixture was stirred for 68 h at 100° C. then allowed to cool to rt. Water (200 mL), brine (200 mL), and $CH_2Cl_2$ (300 mL) were added and the layers were separated. The aqueous layer was extracted with 100 mL of $CH_2Cl_2$. The combined organic layers were washed with brine and dried with $MgSO_4$. Approximately half the solvent was evaporated and hexanes (200 mL) was added. The solvents were evaporated under reduced pressure. The resulting oil was left under vacuum overnight to give 106 g of an oil. Additional hexanes (250 mL) was added, followed by enough $CH_2Cl_2$ to bring the oil into solution. The solvents were evaporated to give 103 g of an oil. $^1$H NMR indicated that this was the desired product, mixed with traces of ethanol. It was used in the next step without additional purification.

Compound 34

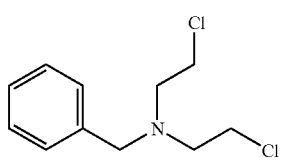

Step 2. Compound 33 (103 g, 0.528 mol) was dissolved in 1,2-dichloroethane (1050 mL) and added to a 3-necked, 3 L round-bottom flask equipped with a stir bar, addition funnel, and reflux condenser. The flask was placed in an oil bath and thionyl chloride (90 mL, 1.23 mol) was added dropwise via addition funnel over 50 min. The flask was kept under $N_2$ flow, with the exhaust gases bubbled through aq. NaOH. During the addition of the thionyl chloride, the reaction mixture was heated to 50° C.-(gas evolution). Once the addition was complete, the reaction mixture was stirred at 60° C. for 1 h and at 70-80° C. for 3 h. The heat was turned off, and the reaction mixture was left stirring overnight. The reaction mixture was concentrated to dryness under reduced pressure. 141.3 g of Compound 34 was obtained. This material was used in the next step without further purification.

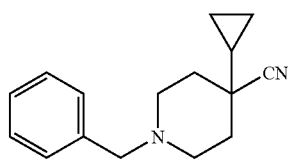

Compound 35

Step 3. A 3-necked, 2 L round-bottom flask was flame dried under $N_2$ flow and allowed to cool to rt. Compound 34 (21.4 g, 79.6 mmol), anhydrous THF (245 mL), and cyclopropyl acetonitrile (7.4 g, 91 mmol) were added. The flask was reblanketed with $N_2$ and cooled in an ice-water bath. Sodium bis(trimethylsilyl)amide (133 mL, 0.5 M in THF, 266 mmol) was added via addition funnel over 1 h. After the addition of the base was complete, additional anhydrous THF was added (250 mL) and the reaction mixture was stirred for 3 h at 0° C. Water (150 mL) was added followed by EtOAc. The layers were separated. The aqueous layer was extracted with EtOAc and the combined organic layer was washed with brine and dried with $MgSO_4$. The solvents were evaporated under reduced pressure to give 38.7 g of an oil. The crude product was purified via sgc using 0-2% $MeOH/CH_2Cl_2$ as the mobile phase. 5.12 g of Compound 35 was obtained.

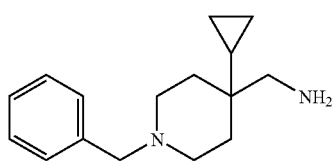

Compound 36

Step 4. In a Parr shaker bottle, Raney Nickel (1 teaspoon— Aldrich 50%) was washed with absolute ethanol, which was decanted off. Methanolic ammonia (60 mL-7N) was added, followed by Compound 35 (1.5 g, 6.2 mmol). The bottle was shaken under 28 psi of hydrogen at rt overnight-(28 psi=0.1 mol). The flask was recharged with 26 psi of $H_2$ and shaken at rt for 3 h and 15 min. The resulting material was filtered through a pad of Celite®, which was rinsed with MeOH. The filtrate was concentrated to give an oil which was purified via sgc using 5:95 $MeOH/CH_2Cl_2$ as the mobile phase, followed by 3:97 $MeOH(NH_3)/CH_2Cl_2$. Approximately 0.5 g of starting material and 0.9 g of Compound 36 were isolated.

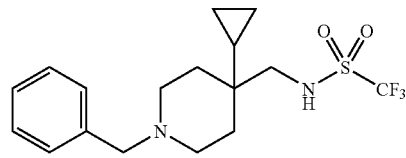

Compound 37

Step 5. Compound 36 (0.8 g, 3.3 mmol) was dissolved in triethylamine (1 mL) and $CH_2Cl_2$ (17 mL), placed under $N_2$ blanket, and cooled to −78° C. Trifluoromethanesulfonic anhydride (0.65 mL, 1.09 mmol) was added. The reaction mixture was stirred at −78° C. for 3 h. MeOH was added (10 mL) and the Dry Ice bath was removed. The solvents were evaporated and the crude reaction mixture was purified via sgc using a 2%-5% $MeOH/CH_2Cl_2$ gradient as the mobile phase. 1.15 g of Compound 37 was obtained.

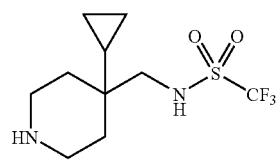

Compound 38

Step 6. Compound 37 (1.11 g, 2.94 mmol) was dissolved in 1,2-dichloroethane (14 mL) and α-chloroethyl chloroformate (0.335 mL, 3.1 mmol) was added. The reaction mixture was placed under $N_2$ blanket and heated to 80° C. The reaction mixture was stirred at 80° C. for 1.5 h. The heat was turned off, and the reaction mixture was stirred at rt over the weekend. Additional α-chloroethyl chloroformate (0.250 mL) was added and the reaction mixture was stirred at 80° C. for 2 h. The reaction mixture was allowed to cool to rt, then concentrated to dryness. MeOH (50 mL) was added and the reaction mixture was refluxed overnight under $N_2$ blanket. The reaction mixture was concentrated to dryness and purified via sgc using a 1.5%-10% $MeOH/CH_2Cl_2$ gradient. 0.627 g of a foam was isolated and identified as the desired Compound 38.

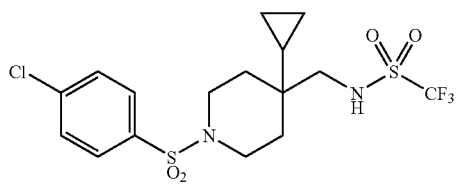

Compound 39

Step 7. Compound 38 (115 mg, 0.401 mmol), 4-chlorobenzenesulfonyl chloride (120 mg, 0.569 mmol), N,N-dimethylaminopyridine (40 mg, 0.327), and tributylamine (200 μL, 0.839 mmol) were dissolved in $CH_2Cl_2$ (2 mL) and left stirring over the weekend at rt. The reaction mixture was diluted with $CH_2Cl_2$ and washed with 1.0 M aq. $NaHSO_4$ and brine. The organic layer was dried with $MgSO_4$ and concentrated to give 0.36 g of an oil. The crude product was purified via sgc using 20-25% EtOAc/hexanes as the mobile phase. 115 mg of Compound 39 was obtained.

Compound 40

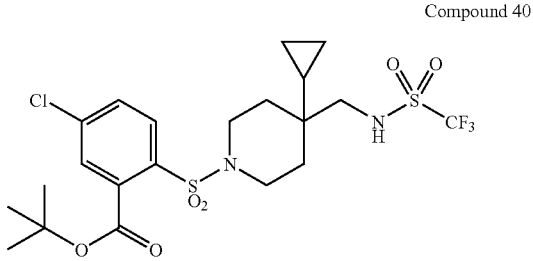

Step 8. Compound BZ Compound 39 (81 mg, 0.175 mmol) was added to a flame dried Schlenk flask equipped with a stir bar. Anhydrous THF (1.5 mL) was added and the flask was blanketed with $N_2$. The flask was placed in a Dry Ice/IPA bath and a solution of n-BuLi in hexanes (155 µL, 0.387 mmol) was added. The reaction mixture was stirred at −78° C. for 1 h and 15 min. Di-t-butyl dicarbonate (108 mg, 0.495 mmol) was added and the reaction mixture was left stirring overnight. The reaction mixture was quenched with 1.0 M, pH 7.0 phosphate buffer and diluted with EtOAc. The layers were separated and the organic layer was washed with water and brine, then dried with $MgSO_4$. Evaporation of the solvent afforded an oil. The crude product was purified via sgc to give 0.04 g of Compound 40 (BZ).

EXAMPLE IX

Compound 41

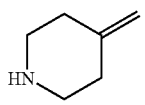

Step 1. 1-(t-Butoxycarbonyl)-4-methylenepiperidine (0.5 g, 2.6 mmol) was stirred in 3:1 $CH_2Cl_2$-TFA (15 mL) at rt for 3 h. The reaction mixture was concentrated under vacuum to give Compound 41 as an oil.

Compound 42

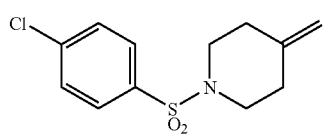

Step 2. Compound 41 (1.55 g, 7.94 mmol) was then dissolved in $CH_2Cl_2$ (50 mL) and the solution was cooled to 0° C. Triethylamine (4.43 mL, 31.8 mmol) and 4-chlorobenzenesulfonyl chloride (2.01 g, 9.53 mmol) were added and the resulting solution was stirred rt for 1.5 h. Water was added and the mixture was extracted with $CH_2Cl_2$ (20 mL). The organic layer was dried over $Na_2SO_4$ and concentrated to dryness. The crude material was purified by sgc (10% EtOAc in hexanes) to give 1.05 g (51%) of Compound 42.

Compound 43

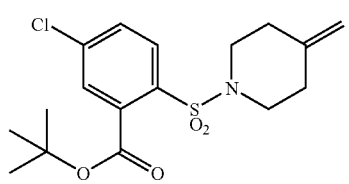

Step 3. In a flame dried flask under $N_2$ blanket, Compound 42 (0.31 g, 1.2 mmol) was dissolved in dry THF (50 mL) and cooled to −78° C. n-BuLi (0.69 mL, 1.90 M solution in hexanes, 1.3 mmol) was added, and the mixture was stirred at −78° C. for 40 min. Di-t-butyl dicarbonate (0.75 g, 3.4 mmol) was added to the reaction mixture, which was stirred at −78° C. for 1.5 h. The reaction mixture was slowly warmed to rt. Water was added to quench the reaction. The reaction mixture was extracted with EtOAc (3×20 mL). The organic layer was dried over $Na_2SO_4$ and concentrated to dryness to give 0.42 g (100%) of crude product, which could be used in the subsequent reaction without further purification. A small portion of the crude product (35 mg) was purified via sgc (10% EtOAc in hexanes) to give 31 mg of Compound 43.

Compound 44

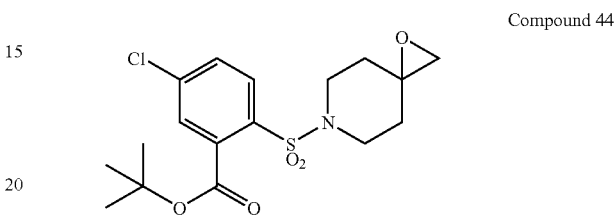

Step 4. Compound 43 (1.22 g, 3.27 mmol) was dissolved in $CH_2Cl_2$ (30 mL). MCPBA (1.41 g, 8.18 mmol) was added and the solution was stirred overnight at rt. The reaction mixture was diluted with $CH_2Cl_2$, and washed with aq. $NaHSO_3$ and aq. $NaHCO_3$. The organic layers were combined, dried over $Na_2SO_4$ and concentrated. The crude material was purified via sgc (25% EtOAc in hexanes) to give 1.25 g (20%) of Compound 44.

Compound 45

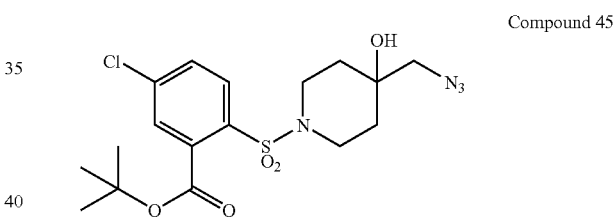

Step 5. Compound 44 (0.52 g, 1.3 mmol) was dissolved in 1,4-dioxane (20 mL) and water (2 mL), and $NaN_3$ (0.26 g, 4.0 mmol) was added. The solution was heated overnight at reflux. The solvent was evaporated under reduced pressure and the residue was taken up by water and extracted with EtOAc (3×10 mL). The organic layers were combined and dried with $Na_2SO_4$. Evaporation of the solvent yielded Compound 45 (100% yield). This material was used in the next step without further purification.

Compound 46

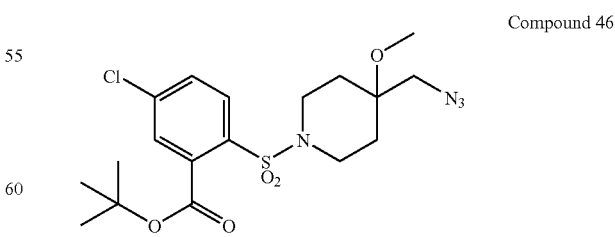

Step 6. Compound 45 (0.30 g, 0.69 mmol) was dissolved in THF (20 mL). Sodium hydride (67 mg, 2.1 mmol) and iodomethane (0.174 mL. 2.1 mmol) were added successively at rt. The resulting mixture was stirred overnight at rt. Water was added. The mixture was extracted with EtOAc (3×10 mL). The combined organic layers were dried over Na₂SO₄ and concentrated to dryness. The crude material was purified via sgc (25% EtOAc in hexanes) to give 81 mg (26%) of Compound 46.

Compound 47

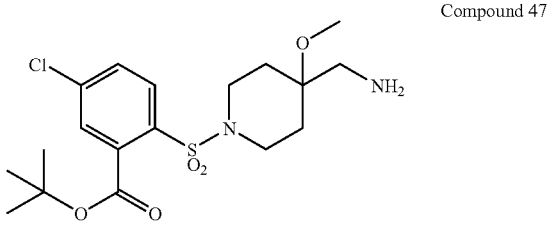

Step 7. Compound 46 (47 mg, 0.11 mmol) was dissolved in THF (5 mL) and water (1 mL). Triphenylphosphine (55 mg, 0.21 mmol) was added and the resulting mixture was stirred overnight at rt. Water was added and the mixture was extracted with EtOAc (3×25 mL). The combined organic layers were dried over Na₂SO₄ and concentrated to dryness. The crude material was purified via sgc (10% 7N NH₃/MeOH solution in EtOAc) to give 25 mg (50%) of Compound 47.

Compound 48

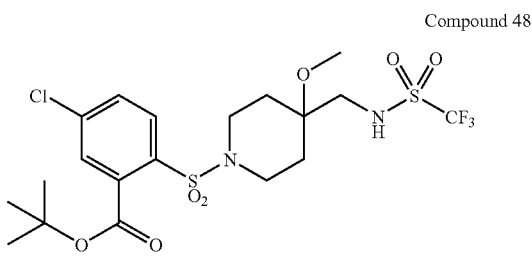

Step 8. Compound AX Compound 47 (25 mg, 0.060 mmol) was dissolved in CH₂Cl₂ (5 mL). Triethylamine (16.6 μL, 0.063 mmol) was added. The solution was cooled to −78° C. Triflic anhydride (10.5 μL) was added dropwise. The reaction mixture was stirred at −78° C. for 1.5 h. The solvent was evaporated and the crude material purified by PTLC plate (25% EtOAc-hexanes) to give 22 mg (80%) of Compound 48 (AX).

EXAMPLE X

Compound 49

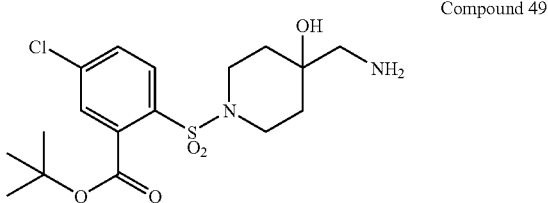

Step 1. Compound 45 (0.19 g, 0.44 mmol) was dissolved in EtOAc (15 mL). Lindlar's catalyst (palladium, 5 wt % in calcium carbonate, poisoned with lead; 0.19 g) was added. The reaction mixture was shaken on a Parr apparatus under hydrogen atmosphere (52 psi) for 48 hrs. The reaction mixture was filtered and the solvent was evaporated. The crude product was purified via sgc to give 50 mg (28%) of Compound 49.

Compound 50

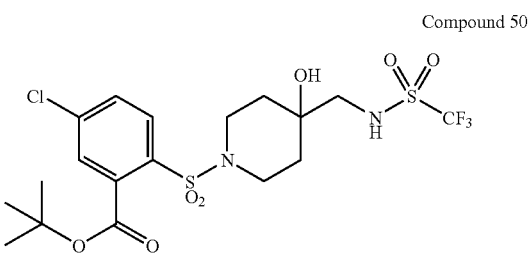

Step 2. Compound BP Compound 49 (48 mg, 0.12 mmol) was dissolved in CH₂Cl₂ (5 mL). NEt₃ (33.0 μL, 0.237 mmol) was added. The mixture was cooled to −78° C. Trifluoromethanesulfonic anhydride (19.9 μL, 0.12 mmol) was added and the reaction mixture was stirred for 1.5 h. The solvent was removed and the resulting crude material purified by PTLC (50% EtOAc in hexanes) to give 37.3 mg (67%) of Compound 50 (BP).

EXAMPLE XI

Compound 51

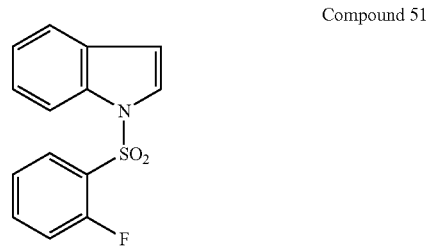

Step 1. In a flame dried flask under N₂ blanket, Indole (5.0 g, 43 mmol) was dissolved in THF (50 mL) and cooled to −78° C. A solution of n-BuLi (1.6 M in hexanes, 29 mL, 47 mmol) was added over 15 min. The resulting anion precipitated as a solid. The reaction mixture was warmed 0° C. and stirred for 1 h before being cooled to −78° C. again. A solution of 2-fluorobenzenesulfonyl chloride (9.1 g, 47 mmol) in THF (30 mL) was added over 20 min. The reaction mixture was allowed to warm slowly to rt and was then stirred overnight at rt. The reaction mixture was poured into 2% aq. NaHCO₃ (120 mL). The aq. layer was extracted with Et₂O (4×50 mL). The combined organic layers were washed with 2% aq. NaHCO₃ (30 mL), H₂O (2×75 mL) and brine (2×50 mL). The organic phase was dried over Na₂SO₄ and concentrated to dryness. The crude product was purified via sgc (5-8% EtOAc in hexanes) to give 11.6 g (98%) of Compound 51.

Compound 52

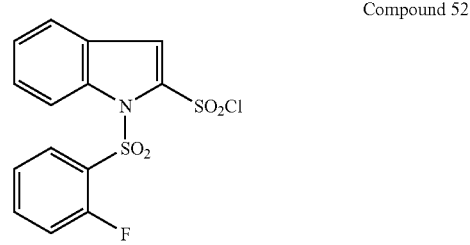

Step 2. In a flame dried flask under N₂ blanket, Compound 51 (1.74 g, 6.3 mmol) was dissolved in dry THF (30 mL) and cooled to −78° C. n-BuLi (1.84 M in hexanes, 3.4 mL, 6.3 mmol) was added and the reaction mixture was stirred for 50 min. SO₂ was bubbled slowly into the reaction vessel for 1 h. The reaction was warmed to rt. The reaction mixture was concentrated to 5 mL. Ice-cold hexanes (200 mL) was added, and precipitation of a solid occurred. The solid was collected reaction mixture was extracted with brine (30 mL). The organic layer was dried over Na₂SO₄, and concentrated to dryness. The crude product was purified by PTLC (33% EtOAc in hexanes) to give 136 mg (50%) of Compound 53 (AT).

Compound 53A:

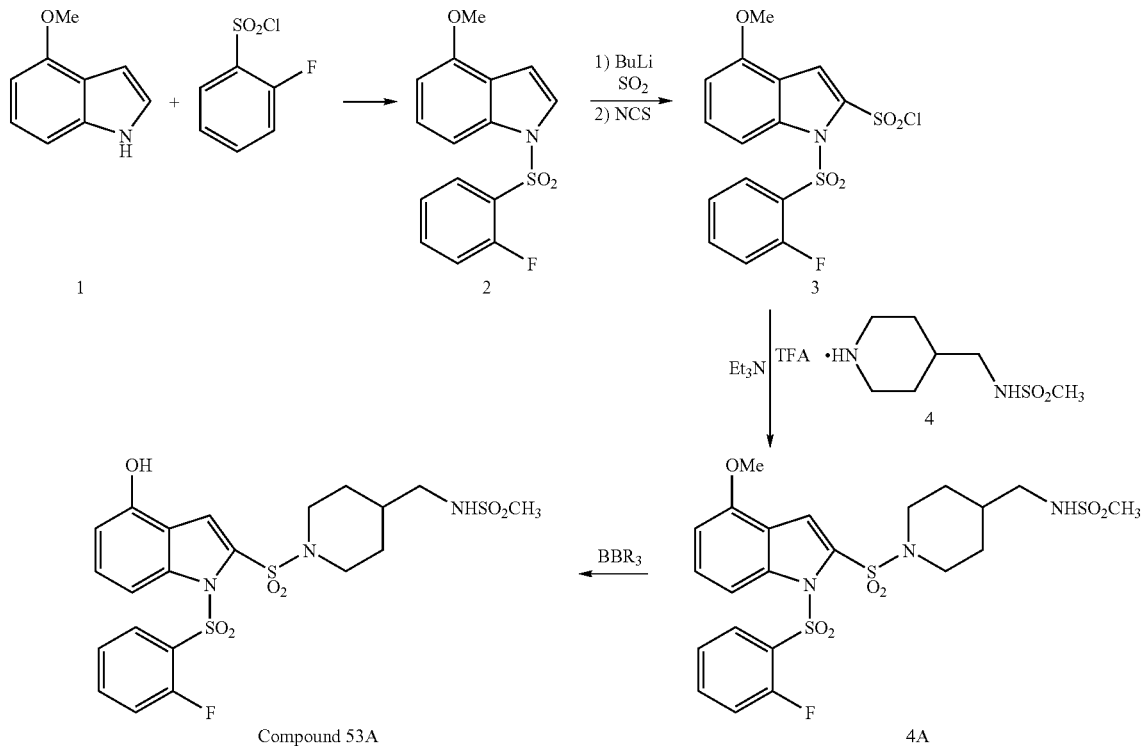

Compound 53A

4A by filtration and was washed with cold hexanes. This solid was dissolved in CH₂Cl₂ (200 mL) at rt. NCS (0.93 g, 7.0 mmol) was added and the reaction was stirred overnight. The mixture was washed with brine and the organic layer was dried over Na₂SO₄ and concentrated to dryness. The crude product was purified via sgc (9% EtOAc in hexanes) to give 800 mg (34%) of Compound 52.

Compound 53

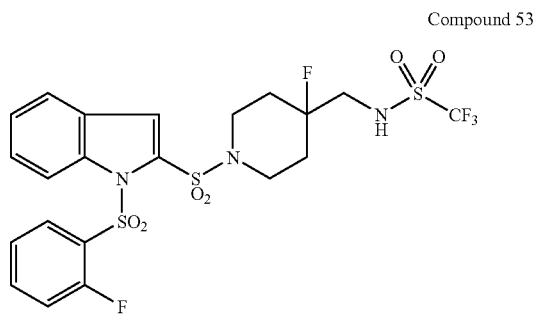

Step 3. Compound AT Compound 52 (170 mg, 0.46 mmol) was dissolved in CH₂Cl₂ (20 mL) at rt. 4-Fluoro-4-(trifluoromethanesulfonamidomethyl)piperidinium trifluoroacetate (344 mg, 0.91 mmol) and triethylamine (92 mg, 0.92 mmol) were added successively. The mixture was stirred for 4 h. The Compound 2: Compound 1 (1 g, 6.79 mmol) was dissolved in CH₂Cl₂ (5 mL). NaOH (50%, 4 mL) was added followed by addition of 2-fluorophenylsulphonyl chloride (1.6 g, 8.22 mmol) and tetrabutylammonium hydrogensulfate (cat.). The reaction mixture was stirred at room temperature overnight. The aqueous layer was then removed, and the organic layer was dried over Na₂SO₄ and concentrated to dryness. The crude product was purified via PTLC (10% EtOAc/hexanes) to give 2 g (97%) of compound 2 as a white solid.

Compound 3: In a flame dried flask under N₂ blanket, compound 2 (2.0 g, 6.55 mmol) was dissolved in dry TFA (30 mL) and cooled to −78° C. A solution of n-butyl lithium (2.04 M in hexanes, 3.3 mL, 6.6 mmol) was added and the reaction mixture was stirred for 45 min. SO₂ was bubbled in the reaction vessel at a slow rate for 45 min. The reaction was warmed to room temperature. The reaction mixture was concentrated to 5 mL. Ice cold hexanes (200 mL) was added, and precipitation occurred. The solid was collected by filtration and it was washed by cold hexanes. This solid was dissolved in CH₂Cl₂ (200 mL) at room temperature. NCS (1.05 g, 7.87 mmol) was added and the reaction was stirred overnight. The mixture was washed with brine and the organic layer was dried over Na₂SO₄, and concentrated to dryness. The crude product was purified via sgc (9% EtOAc/hexanes) to give 780 mg (30%) compound 3 as a light brown solid.

Compound 4A: Compound 3 (100 mg, 0.25 mmol) was dissolved in CH₂Cl₂ (10 mL) at room temperature. Compound 4 (100 mg, 0.33 mmol) was added followed by addition of triethylamine (63 mg, 0.62 mmol). The mixture was stirred at rt overnight. It was extracted with brine (30 mL). The organic layer was dried over Na$_2$SO$_4$, and concentrated to dryness. The crude product was purified with preparative TLC plate (50% EtOAc/hexanes) to give 78 mg (56%) compound 4A as a white powder.

Compound 53A: Compound 4A (78 mg, 0.14 mmol) was dissolved in CH$_2$Cl$_2$ (10 mL) at 0° C. BBr$_3$ (1.0 M in CH$_2$Cl$_2$, 1 mL, 1 mmol) was added. The reaction mixture was slowly warmed up to rt and stirred overnight. The mixture was washed with brine and the organic layer was dried over Na$_2$SO$_4$, and concentrated to dryness. The crude product was purified via sgc (33% EtOAc/hexanes) to give 58 mg (78%) Compound 53A as a white solid.

EXAMPLE XIa

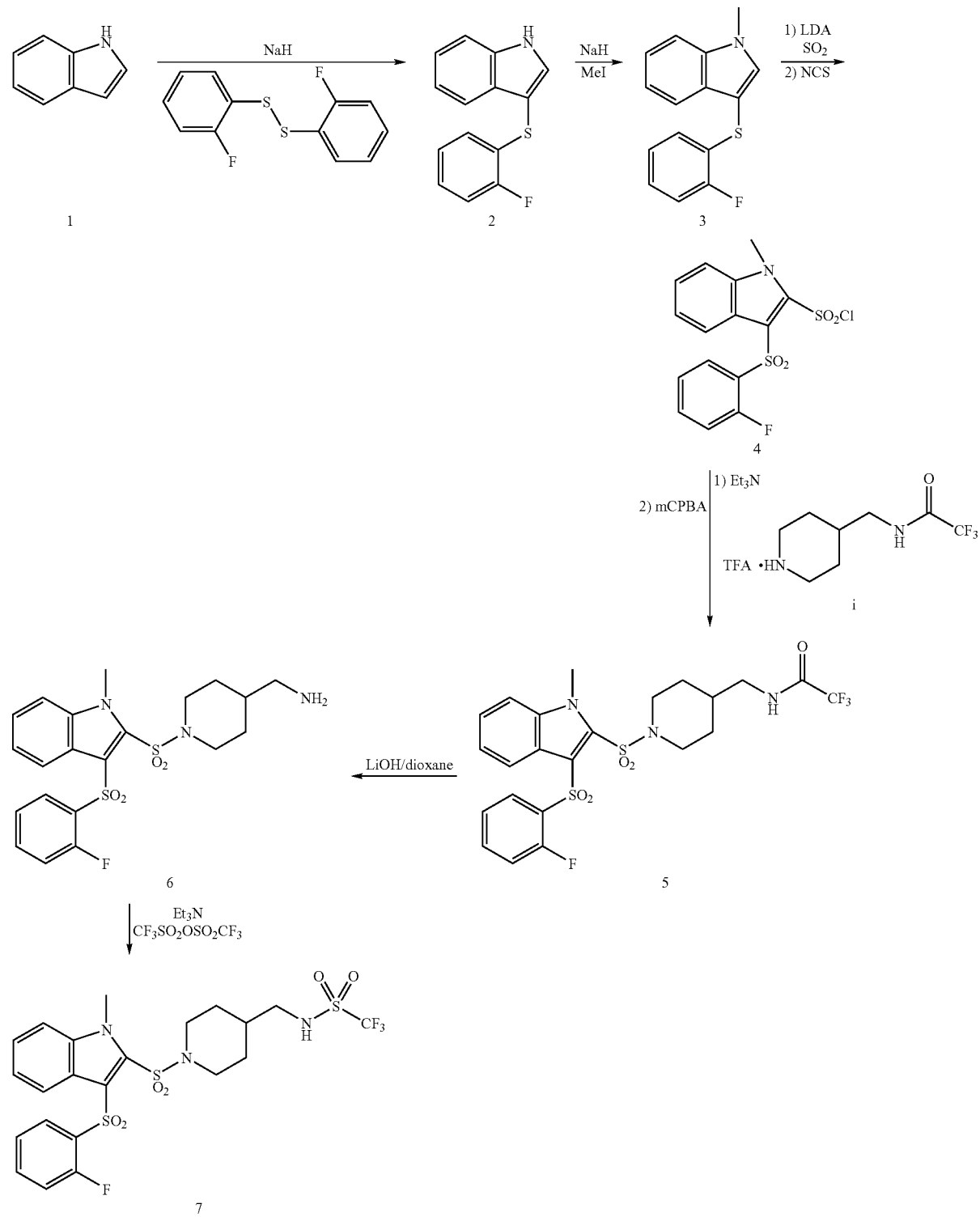

Compound 2: Compound 1 (3 g, 0.026 mol) was dissolved in DMF (150 mL), and cooled to 0° C. NaH (dry, 95%, 0.97 g, 0.038 mol) was added, and the reaction was stirred for 15 min. A solution of 2-fluorophenyl disulphide (6.5 g, 0.026 mol) in DMF (5 mL) was added, and the reaction was allowed to proceed at r.t. overnight. The reaction was quenched with H$_2$O. Solvent was removed. CH$_2$Cl$_2$ was added to dilution the reaction mixture. The organics were extracted with brine (50 ml×2) and H$_2$O (50 ml×2). The organic layer was dried over Na$_2$SO$_4$ and concentrated to dryness. The crude product was purified via (10% EtOAc/hexanes) to give 5.33 g (85%) of compound 2 as a white solid.

Compound 3: Compound 2 (2.1 g, 8.63 mmol) was dissolved in THF (35 mL). NaH (dry, 95%, 1.04 g, 43 mmol) was added, and the reaction was stirred for 15 min. CH$_3$I (4.1 mL, 43 mmol) was added and the reaction was stirred at rt overnight. H$_2$O was added to quench the reaction. EtOAc (20 mL) was added to dilute the reaction mixture. It was washed with brine (40 mL×2). The organic layer was dried and concentrated to give 2.2 g (99%) compound 3 as a white solid.

Compound 4: In a flame dried flask under N$_2$ blanket, compound 3 (2.2 g, 8.6 mmol) was dissolved in dry THF (30 mL) and cooled to −78° C. A solution of LDA (1.4 M in cyclohexanes, 4.65 mL, 6.51 mmol) was added and the reaction mixture was stirred for 20 min. SO$_2$ was bubbled in the reaction for 20 min. It was slowly warmed up to rt. The reaction mixture was concentrated to dryness. The crude material was dissolved in CH$_2$Cl$_2$ (5 mL). Cold hexane was added and precipitation occurred. The solid was collected by filtration and it was washed by cold hexanes. The material was dissolved in CH$_2$Cl$_2$ (40 mL). NCS (2.3 g, 17.2 mmol) was added and it was stirred at rt overnight. The reaction mixture was washed with brine (100 mL×2). The organic layer was dried over Na$_2$SO$_4$ and then concentrated to dryness to give crude compound 41.55 g (100%).

Compound 5: Compound 4 (0.83 g, 2.3 mmol) was dissolved in CH$_2$Cl$_2$ (30 mL) at room temperature. Compound I (0.76 g, 2.3 mmol) was added followed by addition of triethylamine (0.82 mL, 5.87 mmol). The mixture was stirred at rt overnight. It was extracted with brine (30 mL). The organic layer was dried over Na$_2$SO$_4$, and concentrated to dryness. The crude product was dissolved in CH$_2$Cl$_2$ (40 mL) and cooled to 0° C. MCPBA (3.24 g, ca 13.2 mmol) was added. The ice bath was removed and the reaction mixture was stirred at rt overnight. Aqueous NaHCO$_3$ (200 mL) and CH$_2$Cl$_2$ were added and the layers were separated. The organic layer was washed with aq NaHSO$_3$, NaHCO$_3$, H$_2$O, and brine then dried with Na$_2$SO$_4$. The crude product is purified by sgc (33% EtOAc/hexanes) to give 0.57 g (44%) of compound 5 as a white solid.

Compound 6: Compound 5 (0.57 g, 1.01 mmol) was dissolved in dioxane (4 mL) at room temperature. LiOH (1.0 M, 4.0 mL, 4.0 mmol) was added and the mixture was stirred at room temperature for overnight. The solvent was removed and CH$_2$Cl$_2$ (15 mL) and brine (15 mL) was added and the layers were separated. The aqueous layer was extracted with additional CH$_2$Cl$_2$ (15 mL) and the combined organic layers were dried over Na$_2$SO$_4$ and concentrated to dryness to give compound 6 0.44 g (92%).

Compound 7: Compound 6 (70 mg, 0.15 mmol) was dissolved in CH$_2$Cl$_2$ (15 mL) and cooled to −78° C. Et$_3$N (0.053 mL, 0.38 mmol) was added followed by the addition of trifluoromethanesulfonic anhydride (42 mg, 0.15 mmol). The reaction mixture was stirred for 30 min before warming up to 0° C. Brine (15 mL) was added and the product was extracted with CH$_2$Cl$_2$ (50 mL). The organic layer was dried over Na$_2$SO$_4$ and concentrated to dryness. The crude product was purified via PTLC (33% EtOAc/hexanes) to give 40 mg (45%) compound 7 as a white solid.

EXAMPLE XII

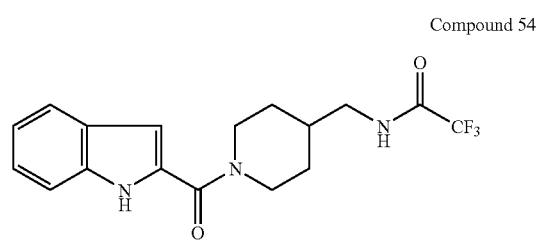

Compound 54

Step 1. Indole-2-carboxylic acid (1.0 g, 6.2 mmol) and 4-(trifluoroacetamidomethyl)piperidinium trifluoroacetate (2.2 g, 6.8 mmol) were dissolved in CH$_2$Cl$_2$ (15 mL). HOBT (1.1 g, 8.1 mmol), EDCl (1.6 g, 8.1 mmol) and triethylamine (815 mg, 8.1 mmol) were added and the mixture was stirred overnight at rt. The crude mixture was washed with brine (2×15 mL). The organic layer was dried over Na$_2$SO$_4$ and concentrated to dryness. The crude product was purified by sgc (EtOAc) to give 1.36 g (62%) of Compound 54.

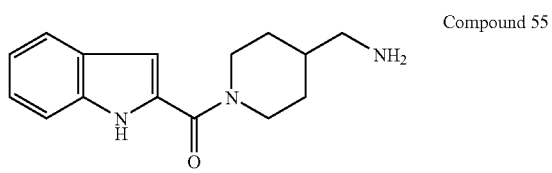

Compound 55

Step 2. Compound 54 (1.0 g, 2.8 mmol) was dissolved in MeOH (10 mL) at rt. NaOH (1.0 M, aq., 10 mL, 10.0 mmol) was added and the mixture was stirred at rt for 4 h. The solvent was removed and CH$_2$Cl$_2$ (30 mL) and brine (30 mL) were added and the layers were separated. The aq. layer was extracted with additional CH$_2$Cl$_2$ (15 mL) and the combined organic layers were dried over Na$_2$SO$_4$ and concentrated to dryness to give 670 mg (100%) of Compound 55.

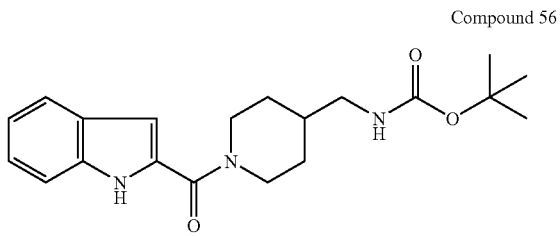

Compound 56

Step 3. Compound 55 (105 mg, 0.40 mmol) was dissolved in 1:1 CH$_2$Cl$_2$-THF(20 mL). BOC-ON (100 mg, 0.40 mmol) and DMAP (catalytic amount) were added and the reaction mixture was stirred overnight at rt. The mixture was then washed with brine, and the organic layer was dried over Na$_2$SO$_4$ and concentrated to dryness. The crude product was purified by PTLC (50% EtOAc in hexanes) to give 144 mg (99%) of Compound 56.

Compound 57

Step 4. Compound 56 (140 mg, 0.39 mmol) was dissolved in CH₂Cl₂ (5 mL). NaOH (1.0 M, aq., 5 mL), 2-fluorobenzenesulfonyl chloride (76 mg, 0.39 mmol), and tetrabutylammonium hydrogen sulfate (catalytic amount) were added successively. The reaction mixture was stirred overnight at rt. The aq. layer was then removed, and the organic layer was dried over Na₂SO₄ and concentrated to dryness. The crude product was purified by PTLC (4% MeOH(NH₃) in CH₂Cl₂) to give 44 mg (22%) of Compound 57.

Compound 58

Step 5. Compound CZ Compound 57 (40 mg, 0.078 mmol) was stirred in 3:1 CH₂Cl₂-TFA (4 mL) at rt for 30 min. The solvent was removed and the crude material was dried under vacuum. This material was dissolved in CH₂Cl₂ (15 mL) and cooled to −78° C. Trifluoromethanesulfonic anhydride (22 mg, 0.078 mmol) and triethylamine (31 mg, 0.31 mmol) were added successively. The reaction mixture was stirred at −78° C. for 1.5 h, allowed to warm slowly to rt, and was stirred for an additional 1 h. The reaction mixture was washed with brine (15 mL). The organic layer was dried over Na₂SO₄ and concentrated to dryness. The crude product was purified by PTLC (50% EtOAc in hexanes) to give 14 mg (33%) of Compound 58 (CZ).

EXAMPLE XIII

Compound 59

Step 1. Lithium aluminum hydride (0.82 g, 22 mmol) was stirred in THF (0.4 mL) at 0° C. A solution of ethyl indole-2-carboxylate (2.0 g, 10 mmol) in THF (13 mL) was added dropwise. The reaction mixture was slowly warmed up to rt and was stirred for 30 min. It was then cooled to 0° C. Water (2 mL), NaOH (1 N, aq., 5 mL), and water (6 mL) were added successively. The mixture was stirred at rt for 15 min, then filtered through Celite® and washed with 10:1 CH₂Cl₂-MeOH (150 mL). The filtrate was washed with brine. The organic layer was dried over Na₂SO₄ and concentrated to give 1.55 g (99%) of Compound 59.

Compound 60

Step 2. Compound 59 (1.5 g, 10 mmol) was dissolved in CH₂Cl₂ (30 mL) at rt. Manganese dioxide (85%, 7.5 g, 73 mmol) was added and the mixture was stirred at rt for 4 h. Another portion of manganese dioxide (85%, 6.0 g, 59 mmol) was added and the mixture was stirred for another 0.5 h. The reaction mixture was filtered through Celite®. The Celite® pad was washed with 10:1 CH₂Cl₂:MeOH (250 mL). The filtrate was concentrated to dryness to give 1.22 g (82%) of Compound 60.

Compound 61

Step 3. Compound 60 (1.0 g, 6.9 mmol) was dissolved in CH₂Cl₂ (20 mL). NaOH (1.0 M, aq., 10 mL), 2-fluorobenzenesulfonyl chloride (1.48 g, 7.59 mmol), and tetrabutylammonium hydrogen sulfate (catalytic amount) were added successively. The reaction mixture was stirred at rt for 3 h. The aq. layer was removed, and the organic layer was dried over Na₂SO₄, then concentrated to dryness. The crude product was purified sgc (25% EtOAc in hexanes) to give 951 mg (46%) of Compound 61.

Compound 62

Step 4. Compound 61 (200 mg, 0.66 mmol) and 4-(trifluoroacetamidomethyl) piperidinium trifluoroacetate (214 mg, 0.66 mmol) were dissolved in CH₂Cl₂ (20 mL) at rt. Titanium tetrachloride (1.0 M in CH₂Cl₂, 0.34 mL, 0.34 mmol) was added followed by addition of triethylamine (0.30 mL, 0.64 mmol). The reaction mixture was stirred overnight at rt. Sodium cyanoborohydride (125 mg, 1.99 mmol) in MeOH (1 mL) was added and the reaction mixture was stirred at rt for 2 h. The reaction mixture was washed with brine (40 mL), and the organic layer was separated, then dried over Na₂SO₄ and concentrated to dryness. The crude material was purified by PTLC (33% EtOAc in hexanes) to give 92 mg (25%) of Compound 62.

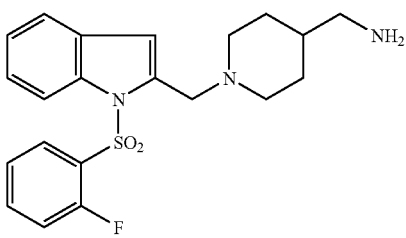

Compound 63

Step 5. Compound 62 (87 mg, 0.18 mmol) was dissolved in 1,4-dioxane (2 mL) at rt. LiOH (1.0 M, aq., 2 mL, 2.0 mmol) was added and the mixture was stirred at rt for 4 h. The solvent was removed and CH$_2$Cl$_2$ (30 mL) and brine (30 mL) were added. The layers were separated. The aq. layer was extracted with additional CH$_2$Cl$_2$ (15 mL). The combined organic layers were dried over Na$_2$SO$_4$ and concentrated to dryness to give 70 mg (100%) of Compound 63.

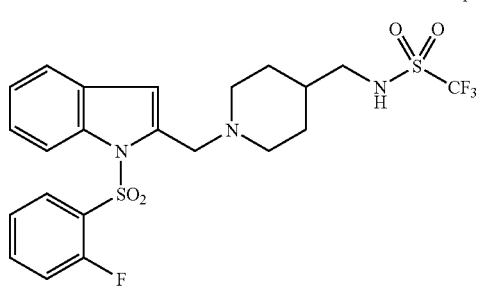

Compound 64

Step 6. Compound DU Compound 63 (50 mg, 0.12 mmol) was dissolved in CH$_2$Cl$_2$ (10 mL) and cooled to −78° C. Trifluoromethanesulfonic anhydride (36 mg, 0.12 mmol) was added followed by addition of triethylamine (25 mg, 0.25 mmol). The reaction mixture was stirred at −78° C. for 45 min. The reaction mixture was washed with brine (15 mL). The organic layer was dried over Na$_2$SO$_4$ and concentrated to dryness. The crude product was purified by PTLC (33% EtOAc in hexanes) to give 43 mg (65%) of Compound 64 (DU).

EXAMPLE XIV

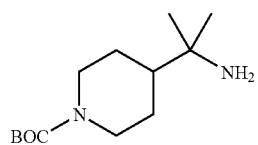

Compound 65

Step 1. Cerium(III) chloride heptahydrate (25.5 g, 68.4 mmol) powder was stirred under vacuum (<0.1 mm Hg) at 145° C. for 18 h. The solid was allowed to cool to rt. THF (120 mL) was added and the solid was stirred at rt for 2 h. The suspension was cooled to −78° C. MeLi (45 mL, 1.4 M in Et$_2$O, 63 mmol) was added dropwise over 30 min. The reaction mixture was stirred −78° C. for 30 min. A solution of 1-(t-butoxycarbonyl)-4-cyanopiperidine (4.35 g, 20.7 mmol) in THF (15 mL) was introduced by cannula, and the reaction was allowed to proceed at −78° C. for 4.5 h. Conc. ammonium hydroxide (40 mL) was added and the reaction mixture was allowed to warm to rt. CH$_2$Cl$_2$ (100 mL) was added and the mixture was stirred at rt for 1 h, then filtered through a Celite® pad. The Celite® pad was washed with CH$_2$Cl$_2$ (3×50 mL). The combined filtrates were concentrated under reduced pressure to afford 5.0 g (99%) of Compound 65.

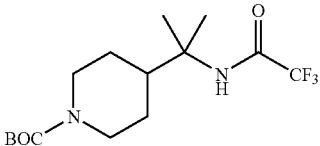

Compound 66

Step 2. To a solution of Compound 65 (5.0 g, 20.7 mmol) and triethylamine (10 mL, 7.3 g, 72 mmol) in CH$_2$Cl$_2$ (100 mL) at 0° C. was added TFAA (3.0 mL, 4.5 g, 21 mmol). The reaction mixture was allowed to warm to rt, and was stirred for 18 h. The reaction mixture was diluted with CH$_2$Cl$_2$ and washed successively with water, 1 M aq NaHCO$_3$, and brine. The organic layer was dried over Na$_2$SO$_4$ and filtered. Removal of the solvent gave a crude solid that was purified by sgc (0.5% MeOH in CH$_2$Cl$_2$) to give 5.8 g (83%) of Compound 66.

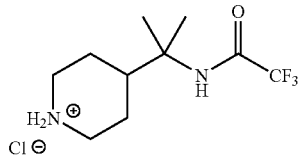

Compound 67

Step 3. A mixture of Compound 66 (5.0 g, 14.8 mmol) and hydrogen chloride solution (100 mL, 4.0 M in dioxane) was stirred at rt for 18 h. Evaporation of the solvent gave 4.0 g (99%) of Compound 67.

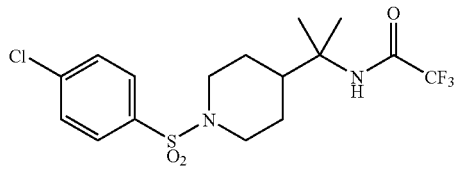

Compound 68

Step 4. To a solution of Compound 67 (500 mg, 1.82 mmol) and triethylamine (1.5 mL, 1.1 g, 11 mmol) was added p-chlorobenzenesulfonyl chloride (390 mg, 1.85 mmol) in portions. The reaction mixture was stirred at rt for 18 h, then diluted with CH$_2$Cl$_2$, and washed successively with 1 N HCl, 1 M aq NaHCO$_3$, and brine. The organic layer was dried over Na$_2$SO$_4$ and filtered. Evaporation of the solvent afforded a solid that was then purified by sgc (3:1 hexanes-EtOAc) to give 690 mg (92%) of Compound 68.

Compound 69

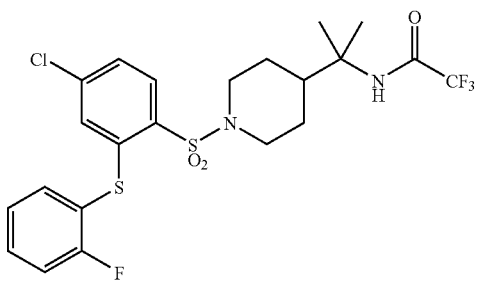

Step 5. To a solution of Compound 68 (380 mg, 0.92 mmol) in THF (10 mL) at −78° C. was added n-BuLi (0.81 mL, 2.5 M in hexanes, 2.0 mmol). The solution was stirred at −78° C. for 30 min. Bis(2-fluorophenyl) disulfide (467 mg, 1.84 mmol) in THF (5 mL) was added dropwise. The reaction mixture was allowed to warm slowly to rt, and was stirred for 18 h. The reaction mixture was diluted with EtOAc and washed with water and brine, dried over Na$_2$SO$_4$, and filtered. Evaporation of the solvent gave a crude solid that was then purified by sgc (3:1 hexanes-EtOAc) to give 400 mg (81%) of Compound 69.

Compound 70

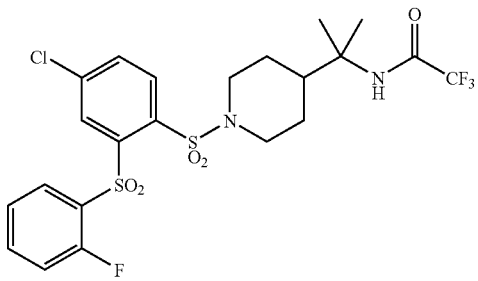

Step 6. A mixture of Compound 69 (340 mg, 0.63 mmol) and MCPBA (550 mg, 3.187 mmol) in CH$_2$Cl$_2$ (30 mL) was stirred at rt for 18 h. The reaction mixture was diluted with CH$_2$Cl$_2$, washed successively with 1 M aq. NaHCO$_3$ and brine, dried over Na$_2$SO$_4$, and filtered. Removal of solvent yielded a white solid that was purified by sgc (3:1 hexanes-EtOAc) to give 218 mg (61%) of Compound 70.

Compound 71

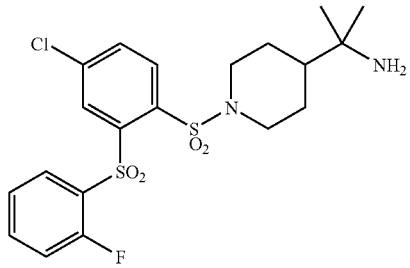

Step 7. To a solution of Compound 70 (210 mg, 0.37 mmol) in 1,4-dioxane (5 mL) was added a solution of lithium hydroxide hydrate (155 mg, 3.7 mmol) in water (1 mL). The reaction mixture was stirred at rt for 18 h, then extracted with EtOAc. The organic phase was washed successively with water and brine, dried over Na$_2$SO$_4$, and filtered. Removal of solvent afforded 165 mg (94%) of Compound 71.

Compound 72

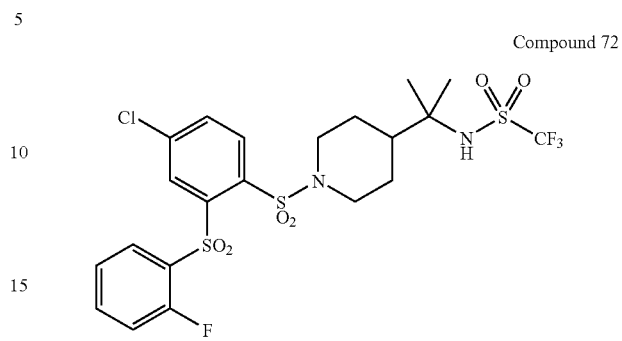

Step 8. Compound BF To a solution of Compound 71 (160 mg, 0.34 mmol) and triethylamine (1 mL, 0.73 g, 7.1 mmol) in CH$_2$Cl$_2$ (10 mL) at −78° C. was added a solution of trifluoromethanesulfonic anhydride (0.06 mL, 100 mg, 0.36 mmol) in CH$_2$Cl$_2$ (2 mL). The reaction mixture was stirred at −78° C. for 15 min, then diluted with CH$_2$Cl$_2$, and washed successively with 1 N HCl, 1 M aq. NaHCO$_3$, and brine. The organic layer was dried over Na$_2$SO$_4$ and filtered. Evaporation of the solvent yielded a solid that was purified by sgc (3:1 hexane-EtOAc) to give 110 mg (53%) of Compound 72 (BF).

EXAMPLE XV

Compound 73

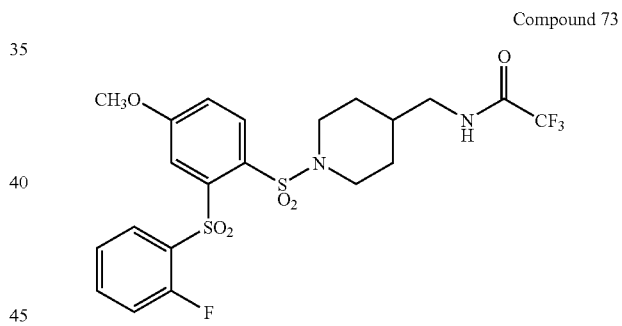

Step 1. Compound 73 was prepared in essentially the same manner as described in Example XIV starting at Step 2 substituting 4-(aminomethyl) piperidine for compound 65 and substituting p-methoxybenzenesulfonyl chloride for p-chlorobenzenesulfonyl chloride in Step 4.

Compound 74

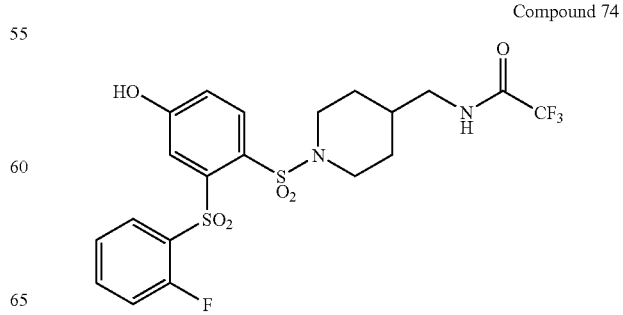

Step 2. To a solution of Compound 73 (837 mg, 1.55 mmol) in CH$_2$Cl$_2$ (10 mL) at −78° C. was added boron tribromide solution (4.6 mL, 1.0 M in CH$_2$Cl$_2$, 4.6 mmol). The reaction mixture was stirred at −78° C. for 15 min, then at 0° C. for 2 h, and then at rt for 48 hr. The reaction mixture was diluted with Et$_2$O and CH$_2$Cl$_2$, and saturated aq. NaHCO$_3$ was added. The aq. phase was extracted further with CH$_2$Cl$_2$. The combined organic layers were washed successively with saturated aq. NaHCO$_3$ and brine, dried over Na$_2$SO$_4$, and filtered. Removal of the solvent afforded 300 mg of Compound 74.

Compound 75

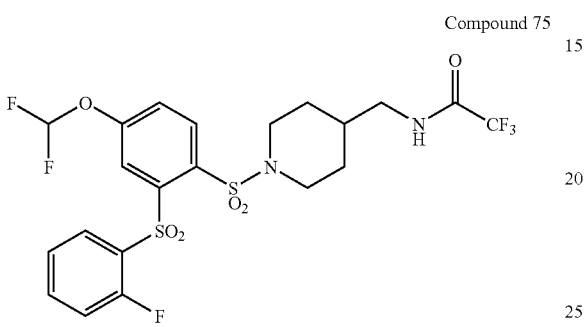

Step 3. Compound CE A solution of Compound 74 (300 mg, 0.572 mmol) and cesium carbonate (1 g, 3.1 mmol) in DMF (5 mL) was heated to 90° C. and allowed to return to rt. Bromodifluoromethane gas was bubbled through the solution for 5 min. The reaction mixture was stirred at 90° C. for 3 h, then at rt for 15 h. The reaction mixture was diluted with EtOAc and washed successively with water and brine. The organic layer was dried over Na$_2$SO$_4$ and filtered. Evaporation of the solvent, followed by purification of the crude product by sgc (30% EtOAc in hexanes) gave 220 mg of Compound 75 (CE).

EXAMPLE XVI

Compound 76

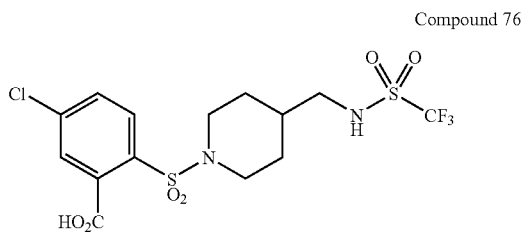

Step 1. A solution of Compound 4 (832 mg, 1.60 mmol) and TFA (1.2 mL, 1.8 g, 16 mmol) in CH$_2$Cl$_2$ (10 mL) was stirred at rt for 15 h, and then partitioned between EtOAc and 0.1 M aq. NaOH solution. The organic layer was extracted further 0.1 M aq. NaOH solution. The combined aq. layers were adjusted to pH 1 with 1 N hydrochloric acid, then extracted with EtOAc (5×50 mL). The combined organic extracts were washed with brine, dried over MgSO$_4$, and filtered. Removal of the solvent, followed by storage under reduced (~0.1 mm Hg) pressure gave 673 mg (91%) of Compound 76.

Compound 77

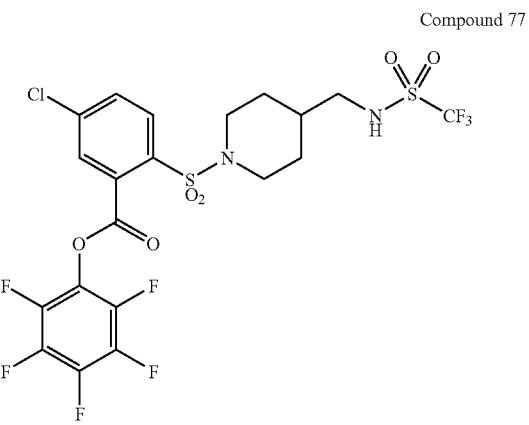

Step 2. Pentafluorophenol (1.85 g, 10.1 mmol) and EDCl.HCl (1.93 g, 10.1 mmol) were added successively to a solution of Compound 76 (2.34 g, 5.03 mmol) in CH$_2$Cl$_2$ (10 mL). The reaction mixture was stirred at rt for 18 h, then diluted with CH$_2$Cl$_2$ and washed successively with water, saturated aq. NaHCO$_3$, and brine. The organic layer was dried over MgSO$_4$ and filtered. Removal of solvent, followed by purification of the resulting crude residue by sgc (2:1 hexanes-EtOAc) gave 3.02 g (95%) of Compound 77.

Compound 78

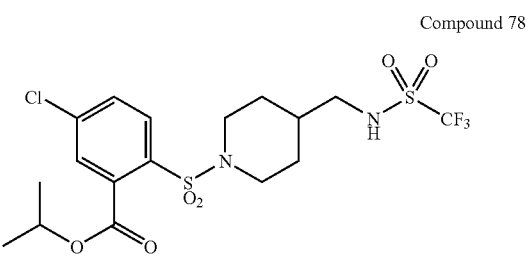

Step 3. Compound H To a suspension of sodium hydride (15 mg, 60% dispersion in mineral oil; 9.2 mg, 0.38 mmol) in DMF (275 μL) was added 2-propanol (40 μL, 31 mg, 0.52 mmol). The resulting solution was stirred at rt for 5 min. Compound 77 (110 mg, 0.174 mmol) was then added in one portion. The reaction mixture was stirred for 75 min, then diluted with EtOAc and poured into saturated aq. NaHSO$_4$ solution. The aq. layer was extracted further with EtOAc. The combined extracts were washed with saturated aq. NaHCO$_3$, water, and brine, then dried over MgSO$_4$, and filtered. Removal of solvent, followed by purification of the resulting oil by sgc (2:1 hexanes-EtOAc) gave 55 mg (63%) of Compound 78 (H).

EXAMPLE XVII

Compound 79

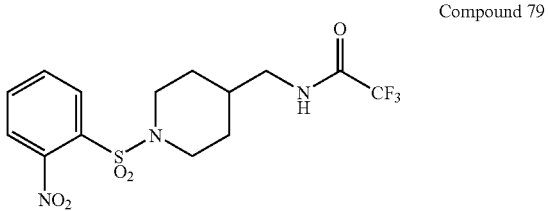

Step 1. A mixture of 4-(trifluoroacetamidomethyl)piperidinium trifluoroacetate (5.0 g, 11.4 mmol) and triethylamine (3.5 mL, 2.5 g, 25 mmol) in CH$_2$Cl$_2$ (40 mL) was cooled to 0° C. and a solution of 2-nitrobenzenesulfonyl chloride (2.53 g, 11.4 mmol) in CH$_2$Cl$_2$ (20 mL) was added. The ice bath was removed and the reaction was allowed to proceed at rt for 18 h. The reaction mixture was poured into water. The layers were separated and the aq. layer was extracted with CH$_2$Cl$_2$. The combined organic layers were washed with brine, dried over MgSO$_4$, and filtered. The solvent was evaporated to afford 4.4 g (97%) of Compound 79.

Compound 80

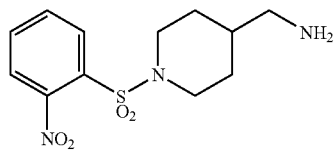

Step 2. To a solution of Compound 79 (2.7 g, 6.8 mmol) in MeOH (27 mL) was added a solution of lithium hydroxide (0.20 g, 8.4 mmol) in water (6 mL). The reaction mixture was stirred at rt for 18 h, then diluted with CH$_2$Cl$_2$ and washed with water. The organic layer was dried over Na$_2$SO$_4$ and filtered. Evaporation of the solvent afforded 1.95 g (95%) of Compound 80.

Compound 81

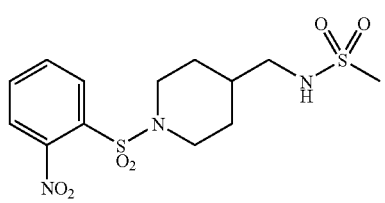

Step 3. A solution of Compound 80 (1.29 g, 4.31 mmol) and triethylamine (0.66 mL, 0.48 g, 4.7 mmol) in CH$_2$Cl$_2$ (40 mL) was cooled to 0° C. and MsCl (0.74 mL, 0.54 g, 4.7 mmol) was added dropwise. The solution was allowed to warm to rt and was then stirred at rt for 18 h. The reaction mixture was diluted with CH$_2$Cl$_2$ and washed successively with water and brine. The organic phase was dried over Na$_2$SO$_4$ and filtered. Removal of the solvent afforded a 1.59 g (98%) of Compound 81.

Compound 82

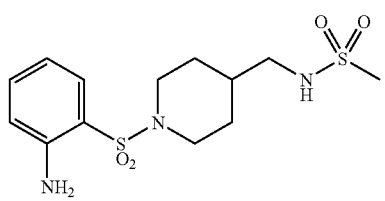

Step 4. A mixture of Compound 81 (1.59 g, 4.21 mmol), conc. hydrochloric acid (0.1 mL), and 10% palladium on carbon (0.1 g) in MeOH (30 mL) was shaken under hydrogen atmosphere (30 psi) for 1 h. The catalyst was removed by filtration. The filtrate was diluted with CH$_2$Cl$_2$ and washed successively with saturated NaHCO$_3$ and water. The organic extracts were dried over Na$_2$SO$_4$ and filtered. Evaporation of the solvent afforded 1.42 g (97%) of Compound 82.

Compound 83

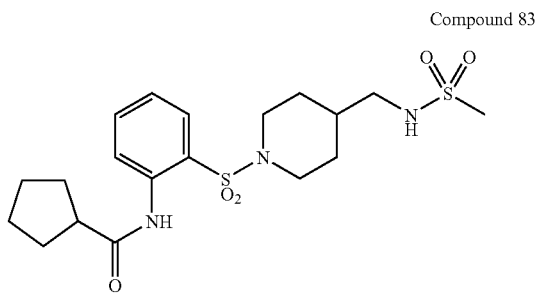

Step 5. Compound AJ A solution of Compound 82 (0.10 g, 0.29 mmol), triethylamine (44 µL, 32 mg, 0.32 mmol), and cyclopentanecarbonyl chloride (42 mg, 0.32 mmol) in CH$_2$Cl$_2$ was stirred at rt for 18 h. The reaction mixture was diluted with CH$_2$Cl$_2$ and washed with 1 N HCl and water. The organic phase was dried over Na$_2$SO$_4$ and filtered. Removal of the solvent afforded a crude solid that was purified by PTLC (5:1 CH$_2$Cl$_2$-Et$_2$O) to give 72 mg (56%) of Compound 83 (AJ).

EXAMPLE XVIII

Compound 84

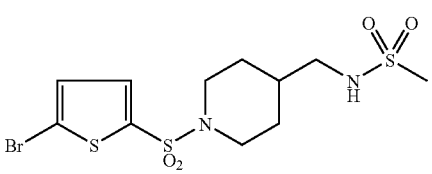

Step 1. A mixture of 4-(methanesulfonamidomethyl)piperidinium trifluoroacetate (0.5 g, 1.6 mmol) and triethylamine (0.5 mL, 0.36 g, 3.6 mmol) in CH$_2$Cl$_2$ (10 mL) was cooled to 0° C. and a solution of 5-bromo-2-thiophenesulfonyl chloride (0.37 g, 1.6 mmol) in CH$_2$Cl$_2$ (5 mL) was added. The ice bath was removed and the reaction was allowed to proceed at rt for 18 h. The reaction mixture was poured into water. The layers were separated and the aq. layer was extracted with CH$_2$Cl$_2$. The combined organic layers were washed with water, dried over MgSO$_4$, and filtered. The solvent was evaporated to afford 0.60 g (89%) of Compound 84.

Compound 85

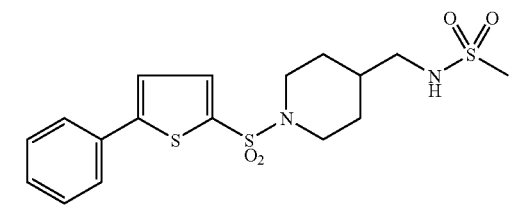

Step 2. Compound W

Tetrakis(triphenylphosphine)palladium(0) (20 mg, 0.017 mmol). was added to a solution of Compound 84 (0.21 g, 0.50 mmol) in THF (6 mL) and the resulting solution was stirred under a nitrogen atmosphere, at rt for 30 min. A solution of potassium carbonate (70 mg, 0.51 mmol) in water (1 mL), followed by phenylboronic acid (74 mg, 0.61 mmol), was added. The reaction mixture was stirred at reflux, under a nitrogen atmosphere for 24 h, then allowed to cool to rt. The reaction was diluted with EtOAc and washed successively with water and brine, dried over Na₂SO₄, and filtered. Removal of the solvent yielded a crude product that was purified by PTLC (3:1 CH₂Cl₂-Et₂O) to give 72 mg (35%) of Compound 85 (W).

EXAMPLE XIX

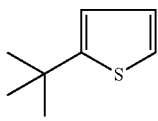

Compound 86

Step 1. To a suspension of aluminum trichloride (19.1 g, 0.143 mol) in CH₂Cl₂ (30 mL) at −78° C. was added, dropwise over 1 h, a solution of thiophene (12.0 g, 0.143 mol) and t-butyl bromide (19.6 g, 0.143 mol) in CH₂Cl₂ (30 mL). The reaction mixture was stirred at −78° C. for 2 h, then allowed to warm to rt, and stirred for a further 18 h. The reaction mixture was diluted with CH₂Cl₂, and washed with water, 5% NaOH, and water. The organic layer was dried over Na₂SO₄ and filtered. Removal of the solvent under reduced pressure afforded a liquid that was purified by vacuum distillation (~20 mmHg) to give 10.7 g (53%) of Compound 86.

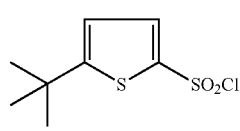

Compound 87

Step 2. A solution of Compound 86 (1.40 g, 9.98 mmol) in CH₂Cl₂ (10 mL) was added dropwise to an ice-cold solution of chlorosulfonic acid (3.5 g, 30 mmol) in CH₂Cl₂ (30 mL). The reaction mixture was stirred for 30 min at 0° C., and then poured into ice. The aq. solution was extracted with CH₂Cl₂. The organic phase was washed with H₂O, dried over Na₂SO₄, and filtered. Evaporation of the solvent gave 2.11 g (89%) of Compound 87.

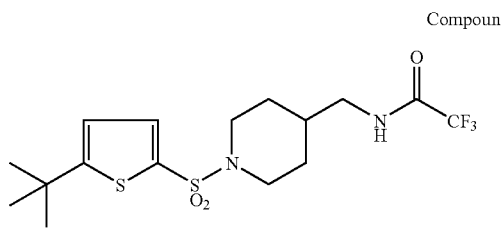

Compound 88

Step 3. A mixture of 4-(trifluoroacetamidomethyl)piperidinium trifluoroacetate (3.87 g, 8.8 mmol) and triethylamine (2.7 mL, 2.0 g, 19.5 mmol) in CH₂Cl₂ (30 mL) was cooled to 0° C. and a solution of Compound 87 (2.11 g, 8.84 mmol) in CH₂Cl₂ (5 mL) was added. The ice bath was removed and the reaction was allowed to proceed at rt for 4 h. The reaction mixture was poured into water. The layers were separated and the aq. layer was extracted with EtOAc. The combined organic layers were washed with water, dried over Na₂SO₄, and filtered. The solvent was evaporated to afford a solid that was then purified by sgc (3:1 hexanes-EtOAc) to give 3.30 g (90%) of Compound 88.

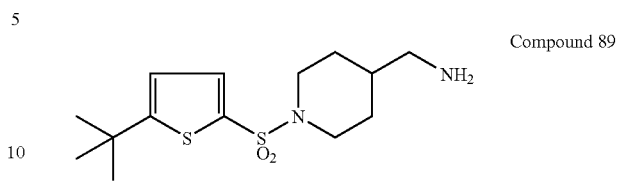

Compound 89

Step 4. To a solution of Compound 88 (1.82 g, 4.41 mmol) in 1,4-dioxane (90 mL) was added aq. lithium hydroxide solution (90 mL, 1.0 M). The reaction mixture was stirred at rt for 3 h, then diluted with CH₂Cl₂ and washed with water. The organic phase was dried over Na₂SO₄ and filtered. Evaporation of the solvent gave 1.52 g (100%) of Compound 89.

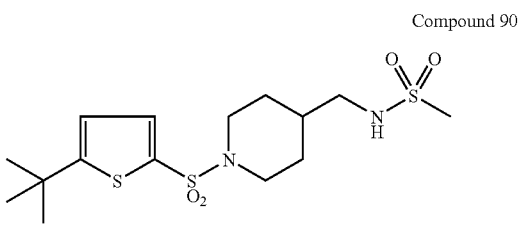

Compound 90

Step 5. Compound CU A solution of Compound 89 (0.17 g, 0.54 mmol) and triethylamine (0.087 mL, 0.063 g, 0.60 mmol) in CH₂Cl₂ (5 mL) was cooled to 0° C. and MsCl (0.046 mL, 68 mg, 0.59 mmol) was added dropwise. The solution was allowed to warm to rt and was then stirred at rt for 3 h. The reaction mixture was diluted with CH₂Cl₂ and washed with water. The organic phase was dried over Na₂SO₄ and filtered. Removal of the solvent afforded a residue that was then purified by sgc (2:1 hexanes-EtOAc) to give 74 mg (35%) of Compound 90 (CU).

It will be understood that various modifications may be made to the embodiments and examples disclosed herein. Therefore, the above description should not be construed as limiting, but merely as exemplifications of preferred embodiments. Those skilled in the art will envision various modifications within the scope and spirit of the claims appended hereto.

We claim:
1. A compound of the formula I:

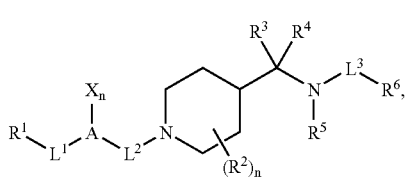

I or a pharmaceutically acceptable salt said compound, wherein:
$L^1$ is —C(O)—, —C(O)O—, —S(O₂)—, —S(O)—, or —S—;
$L^2$ is —S(O₂)—;
$L^3$ is —C(O)— or —S(O₂)—;

R¹ is selected from the group consisting of alkyl, haloalkyl, cycloalkyl, cycloalkylalkyl, heterocyclylalkyl, —Si(alkyl)$_n$(aryl)$_{3-n}$, aryl and heteroaryl, wherein each of said aryl or heteroaryl can be unsubstituted or optionally independently substituted with one to five moieties which can be the same or different and are independently selected from the group consisting of halogen, alkyl, cycloalkyl, cycloalkylalkyl, haloalkyl, haloalkoxy, alkoxy, —N(R⁷)$_2$, —C(O)OR⁷, —C(O)N(R⁷)$_2$, —NC(O)R⁷, —NC(O)OR⁷, —NC(O)N(R⁷)$_2$, —NO$_2$, —CN, —S(O$_2$)R⁷, —S(O$_2$)N(R⁷)$_2$, —NC(=N—CN)NHR⁷, and OH, with the proviso that:
when R¹ is —NHR⁷ or —N(R⁷)$_2$, L¹ —C(O)—, —S(O$_2$)— or —SO—;
R² is H, —OH, halogen, —N(R⁷)$_2$, —CF$_3$, alkoxy, alkyl, haloalkyl, cycloalkyl or cycloalkylalkyl;
R³ and R⁴ are the same or different, and are independently H or alkyl, or R³ and R⁴ taken together form a carbonyl group, i.e. C(=O);
R⁵ is H or alkyl;
R⁶ is selected from the group consisting of H, alkyl, haloalkyl, cycloalkyl, NHR⁷, N(R⁷)$_2$, aryl and heteroaryl, wherein each of said aryl and heteroaryl can be unsubstituted or optionally independently substituted with one to five moieties which moieties can be the same or different and are independently selected from the group consisting of halogen, alkyl, cycloalkyl, haloalkyl, haloalkoxy, alkoxy and OH;
R⁷ is selected from H, alkyl, haloalkyl, cycloalkyl, heterocyclylalkyl, aryl and heteroaryl, wherein each of said aryl and heteroaryl can be unsubstituted or optionally independently substituted with one to five moieties which moieties can be the same or different and are independently selected from the group consisting of halogen, alkyl, cycloalkyl, haloalkyl, haloalkoxy, alkoxy and/or OH;
A is phenyl;
X is independently selected from the group consisting of H, halogen, alkyl, cycloalkyl, haloalkyl, hydroxy, alkoxy, alkoxycarbonyl, haloalkoxy, —N(R⁷)$_2$, —N(R⁷)(C(O)R⁷), —N(R⁷)(C(O)OR⁷), —NO$_2$ and —CN, and when A is selected from the group consisting of pyridyl, thienyl, thiazolyl, quinolyl, isoquinolyl, pyrazinyl, pyridazinyl, pyrrolyl, pyrimidyl, cinnolinyl, quinazolinyl, quinoxalinyl, phthalazinyl, and benzothienyl, X can be oxide; and
n is 0-3,
with the proviso that (i) the two R⁷ moieties in —N(R⁷)$_2$ can be the same or different and are independently selected, and (ii) the moiety —N(R⁵)-L³—R⁶ can optionally form a ring system.

2. A compound according to claim 1 wherein
L¹ is —C(O)—, —S(O)—, —C(O)O—, or —S(O$_2$)—;
L² is —S(O$_2$)—;
L³ is —C(O)— or —S(O$_2$)—;
R¹ is alkyl, haloalkyl, cycloalkyl, aryl or heteroaryl, wherein said aryl and heteroaryl can be unsubstituted or optionally independently substituted with one to five moieties which can be the same or different and are independently selected from the group consisting of halogen, alkyl, cycloalkyl, haloalkyl, haloalkoxy, —CN, (C$_1$-C$_6$)alkoxy and OH;
R² is H, OH, halogen, CF$_3$, alkoxy, —N(R⁷)$_2$, (C$_1$-C$_6$)alkyl, (C$_1$-C$_6$)haloalkyl, —CH$_2$—(C$_3$-C$_5$)cycloalkyl, or (C$_3$-C$_5$)cycloalkyl;
R³ and R⁴ are the same or different, and are independently selected from H or (C$_1$-C$_6$)alkyl;

R⁵ is H or (C$_1$-C$_6$)alkyl;
R⁶ is H, (C$_1$-C$_6$)alkyl, or haloalkyl;
A is phenyl;
X is selected from the group consisting of H, halogen, alkyl, haloalkyl, (C$_3$-C$_5$)cycloalkyl, hydroxy, alkoxy, and haloalkoxy and
n is 0-2.

3. A compound according to claim 1 wherein
L¹ is —C(O)O— or —S(O$_2$)—;
L² is —S(O$_2$)—;
L³ is —C(O)— or S(O$_2$)—;
R¹ is alkyl, haloalkyl, cycloalkyl, aryl or heteroaryl, wherein said aryl and heteroaryl can be unsubstituted or optionally independently substituted with one to five moieties which can be the same or different and are independently selected from the group consisting of halogen, alkyl, cycloalkyl, haloalkyl, haloalkoxy, (C$_1$-C$_6$)alkoxy and OH;
R² is H, OH, halogen, CF$_3$, alkoxy, (C$_1$-C$_6$)alkyl, (C$_1$-C$_6$)haloalkyl, —CH$_2$—(C$_3$-C$_5$)cycloalkyl or (C$_3$-C$_5$)cycloalkyl;
R³ and R⁴ are H;
R⁵ is H or C$_1$-C$_6$ alkyl;
R⁶ is H, C$_1$-C$_6$ alkyl, or haloalkyl;
A is phenyl;
X is selected from the group consisting of H, halogen, alkyl, haloalkyl, (C$_3$-C$_5$)cycloalkyl, hydroxy, alkoxy, and haloalkoxy and
n is 0-2.

4. The compound according to claim 1 having the formula 2:

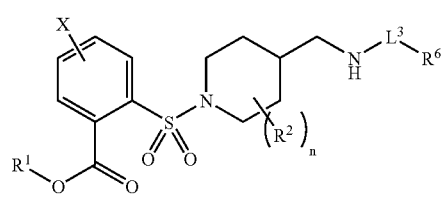

wherein:
L³ is —C(O)— or —S(O$_2$)—;
R¹ is alkyl, haloalkyl, cycloalkyl, aryl or heteroaryl, wherein said aryl and heteroaryl can be unsubstituted or optionally independently substituted with one to five moieties which can be the same or different and are independently selected from the group consisting of halogen, alkyl, cycloalkyl, haloalkyl, haloalkoxy, (C$_1$-C$_6$)alkoxy and OH;
R² is H, OH, F, (C$_1$-C$_6$)alkyl, (C$_1$-C$_6$)haloalkyl, alkoxy or (C$_3$-C$_5$)cycloalkyl;
R⁶ is H, C$_1$-C$_6$ alkyl, or haloalkyl;
X is selected from the group consisting of H, halogen, alkyl, haloalkyl, (C$_3$-C$_5$)cycloalkyl alkoxy, hydroxy and haloalkoxy and
n is 0-2.

5. The compound according to claim 1 having the formula 3:

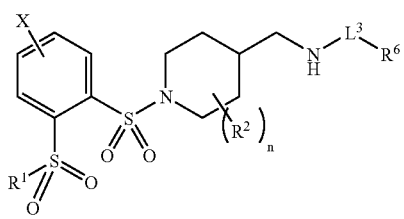

wherein:
L³ is —C(O)— or —S(O₂)—;
R¹ is alkyl, haloalkyl, cycloalkyl, aryl or heteroaryl, wherein said aryl and heteroaryl can be unsubstituted or optionally independently substituted with one to five moieties which can be the same or different and are independently selected from the group consisting of halogen, alkyl, cycloalkyl, haloalkyl, haloalkoxy, (C₁-C₆)alkoxy and OH;
R² is H, OH, F, (C₁-C₆)alkyl, (C₁-C₆)haloalkyl, alkoxy or (C₃-C₅)cycloalkyl;
R⁶ is H, C₁-C₆ alkyl, or haloalkyl;
X is selected from the group consisting of H, halogen, alkyl, haloalkyl, (C₃-C₅)cycloalkyl, alkoxy, hydroxy and haloalkoxy and
n is 0-2.

6. The compound according to claim 1 wherein:
L¹ is —C(O)O— or —S(O₂)—;
L² is —S(O₂)—;
L³ is —C(O)— or —S(O₂)—;
R¹ is selected from the group consisting of t-butyl, i-propyl, neopentyl, 2-trifluoromethyl-2-propyl, 1,1-bis(trifluoromethyl)-1-ethyl, 2-fluorophenyl, 2,6-difluorophenyl, 2-pyridyl, and 2-pyrimidyl;
R² is H, F, (C₁-C₆)alkyl, OH, or alkoxy;
R³ =R⁴ =H;
R⁵ is H;
R⁶ is CH₃ or CF₃;
A is phenyl;
X is selected from the group consisting of H, F, Cl, Br, CF₃, —OCH₃, —OCF₃ and —OCHF₂; and
n is 0-2.

7. The compound according to claim 1 of the formula:

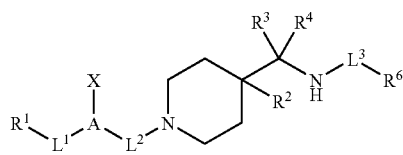

or a pharmaceutically acceptable salt thereof, wherein R¹, R², R³, R⁴, R⁶, A, L¹, L², L³ and X are as set forth in the following table:

| Cmp | R¹ | R² | R³ | R⁴ | R⁶ | A = | L¹ | L² | L³ | X |
|---|---|---|---|---|---|---|---|---|---|---|
| A | 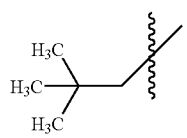 | H | H | H | CF₃ | 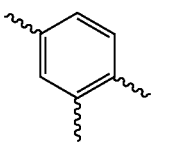 | CO₂ | SO₂ | SO₂ | Cl |
| B | 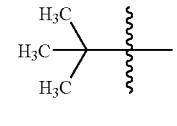 | H | H | H | CH₃ | 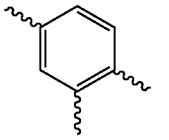 | CO₂ | SO₂ | SO₂ | OCF₃ |
| C | 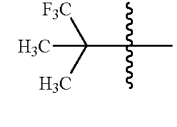 | H | H | H | CF₃ | 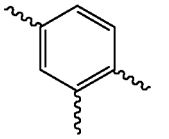 | CO₂ | SO₂ | SO₂ | Cl |
| D | 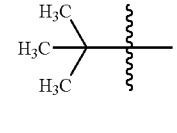 | H | H | H | CF₃ | 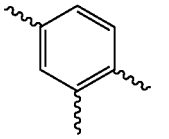 | CO₂ | SO₂ | SO₂ | H |
| E | 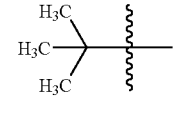 | H | H | H | CF₃ | 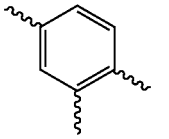 | CO₂ | SO₂ | SO₂ | Cl |

-continued

| Cmp | R$^1$ | R$^2$ | R$^3$ | R$^4$ | R$^6$ | A = | L$^1$ | L$^2$ | L$^3$ | X |
|---|---|---|---|---|---|---|---|---|---|---|
| F | (CH$_3$)$_3$C- | H | H | H | CH$_3$ | phenyl | CO$_2$ | SO$_2$ | SO$_2$ | Cl |
| G | cyclobutyl | H | H | H | CF$_3$ | phenyl | CO$_2$ | SO$_2$ | SO$_2$ | Cl |
| H | i-propyl | H | H | H | CF$_3$ | phenyl | CO$_2$ | SO$_2$ | SO$_2$ | Cl |
| I | (CH$_3$)$_3$C- | H | H | H | CH$_3$ | phenyl | CO$_2$ | SO$_2$ | SO$_2$ | H |
| J | 2-F-phenyl | H | H | H | CH$_3$ | phenyl | SO$_2$ | SO$_2$ | SO$_2$ | OCH$_3$ |
| K | phenyl | H | H | H | CH$_3$ | phenyl | SO$_2$ | SO$_2$ | SO$_2$ | OCH$_3$ |
| L | 2-F-phenyl | H | H | H | CH$_3$ | phenyl | SO$_2$ | SO$_2$ | SO$_2$ | OCF$_2$H |
| M | 2-F-phenyl | H | H | H | CH$_3$ | phenyl | SO$_2$ | SO$_2$ | SO$_2$ | OCF$_3$ |
| N | 2-F-phenyl | H | H | H | C$_2$H$_5$ | phenyl | SO$_2$ | SO$_2$ | SO$_2$ | OCF$_2$H |
| O | 2-F-phenyl | H | H | H | CH$_3$ | phenyl | SO$_2$ | SO$_2$ | SO$_2$ | Cl |

-continued

| Cmp | R¹ | R² | R³ | R⁴ | R⁶ | A = | L¹ | L² | L³ | X |
|---|---|---|---|---|---|---|---|---|---|---|
| P | 2-F-phenyl | H | H | H | $C_2H_5$ | 1,4-phenylene | $SO_2$ | $SO_2$ | $SO_2$ | $OCF_3$ |
| Q | 2-F-phenyl | H | H | H | $CF_3$ | 1,4-phenylene | $SO_2$ | $SO_2$ | $SO_2$ | $CF_3$ |
| R | 2,3-diF-phenyl | H | H | H | $CF_3$ | 1,4-phenylene | $SO_2$ | $SO_2$ | $SO_2$ | Cl |
| S | 2-F-phenyl | H | H | H | $CF_3$ | 1,4-phenylene | $SO_2$ | $SO_2$ | C=O | $OCH_3$ |
| T | 2-F-phenyl | H | H | H | $CH_3$ | phenyl | $SO_2$ | $SO_2$ | $SO_2$ | H |
| U | 2-Cl-phenyl | H | H | H | $CF_3$ | 1,4-phenylene | $SO_2$ | $SO_2$ | C=O | $OCH_3$ |
| X | $C_3H_7$ | H | H | H | $CH_3$ | 1,4-phenylene | $SO_2$ | $SO_2$ | $SO_2$ | $OCH_3$ |
| Y | 2-F-phenyl | H | H | H | $CF_3$ | 1,4-phenylene | SO | $SO_2$ | C=O | Cl |
| AB | 2-F-phenyl | H | H | H | $CH_3$ | 1,4-phenylene | $CH_2$ | $SO_2$ | $SO_2$ | Cl |
| AC | 3-F-phenyl | H | H | H | $CH_3$ | 1,4-phenylene | $CH_2$ | $SO_2$ | $SO_2$ | Cl |

-continued

| Cmp | R¹ | R² | R³ | R⁴ | R⁶ | A = | L¹ | L² | L³ | X |
|---|---|---|---|---|---|---|---|---|---|---|
| AD | 4-F-phenyl | H | H | H | CH₃ | phenyl | C=O | SO₂ | SO₂ | Cl |
| AK | tert-butyl | OCH₃ | H | H | CH₃ | phenyl | CO₂ | SO₂ | SO₂ | Cl |
| AL | 2-F-phenyl | CH₃ | H | H | CF₃ | phenyl | SO₂ | SO₂ | SO₂ | Cl |
| AM | 2-F-phenyl | CH₃ | H | H | CH₃ | phenyl | SO₂ | SO₂ | SO₂ | Cl |
| AN | tert-butyl | CH₃ | H | H | CF₃ | phenyl | CO₂ | SO₂ | SO₂ | Cl |
| AP | tert-butyl | H | H | H | CF₃ | phenyl | CO₂ | SO₂ | SO₂ | OCH₃ |
| AQ | 2-F-phenyl | F | H | H | CF₃ | phenyl | SO₂ | SO₂ | SO₂ | Cl |
| AR | tert-butyl | F | H | H | CF₃ | phenyl | CO₂ | SO₂ | SO₂ | Cl |
| AS | pyridin-2-yl | F | H | H | CF₃ | phenyl | SO₂ | SO₂ | SO₂ | Cl |
| AU | 2,6-diF-phenyl | F | H | H | CF₃ | phenyl | SO₂ | SO₂ | SO₂ | Cl |

-continued

| Cmp | R¹ | R² | R³ | R⁴ | R⁶ | A = | L¹ | L² | L³ | X |
|---|---|---|---|---|---|---|---|---|---|---|
| AV | 2-fluorophenyl | OCH₃ | H | H | CF₃ | 1,3,4-phenyl | SO₂ | SO₂ | SO₂ | Cl |
| AW | 2-fluorophenyl | OCH₃ | H | H | CF₃ | 1,3,4-phenyl | SO₂ | SO₂ | SO₂ | Cl |
| AX | tert-butyl | OCH₃ | H | H | CF₃ | 1,3,4-phenyl | CO₂ | SO₂ | SO₂ | Cl |
| AY | phenyl | H | H | H | CH₃ | 1,3,4-phenyl | SO₂ | SO₂ | SO₂ | OCF₃ |
| AZ | 2-fluorophenyl | H | H | H | CF₃ | 1,3,4-phenyl | SO₂ | SO₂ | SO₂ | OCF₃ |
| BA | 2-fluorophenyl | H | H | H | CF₃ | 1,3,4-phenyl | SO₂ | SO₂ | SO₂ | Cl |
| BD | tert-butyl | H | H | H | CF₃ | 1,3,4-phenyl | CO₂ | SO₂ | SO₂ | OCF₃ |
| BE | C(CF₃)₂CH₃ | H | H | H | CF₃ | 1,3,4-phenyl | CO₂ | SO₂ | SO₂ | Cl |
| BF | 2-fluorophenyl | H | CH₃ | CH₃ | CF₃ | 1,3,4-phenyl | SO₂ | SO₂ | SO₂ | Cl |
| BG | 2-fluorophenyl | H | CH₃ | CH₃ | CF₃ | 1,3,4-phenyl | SO₂ | SO₂ | C=O | CF₃ |

-continued
| Cmp | R¹ | R² | R³ | R⁴ | R⁶ | A = | L¹ | L² | L³ | X |
|---|---|---|---|---|---|---|---|---|---|---|
| BH | 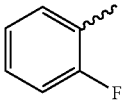 | H | CH₃ | CH₃ | CF₃ | 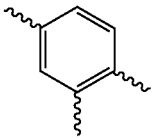 | SO₂ | SO₂ | C=O | Cl |
| BI | 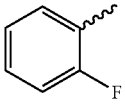 | H | CH₃ | CH₃ | CF₃ | 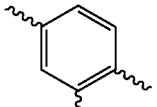 | SO₂ | SO₂ | SO₂ | CF₃ |
| BK | 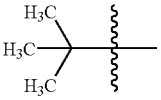 | H | CH₃ | CH₃ | CF₃ | 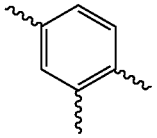 | CO₂ | SO₂ | SO₂ | Cl |
| BL | 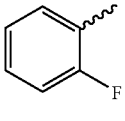 | F | H | H | CF₃ | 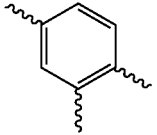 | SO₂ | SO₂ | SO₂ | CF₃ |
| BM | 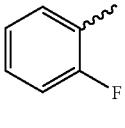 | OCH₃ | H | H | CF₃ | 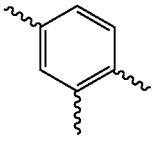 | S | SO₂ | SO₂ | Cl |
| BN | 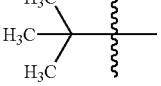 | F | H | H | CF₃ | 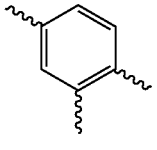 | CO₂ | SO₂ | SO₂ | CF₃ |
| BO | 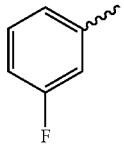 | F | H | H | CF₃ | 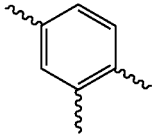 | SO₂ | SO₂ | SO₂ | Cl |
| BP | 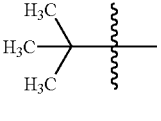 | OH | H | H | CF₃ | 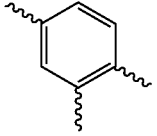 | CO₂ | SO₂ | SO₂ | Cl |
| BQ | 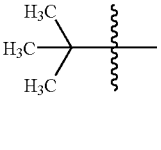 | 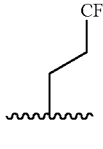 | H | H | CH₃ | 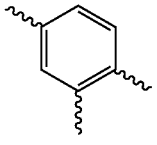 | CO₂ | SO₂ | SO₂ | Cl |
| BR | 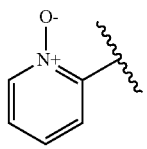 | F | H | H | CF₃ | 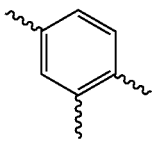 | SO₂ | SO₂ | SO₂ | Cl |

-continued

| Cmp | R¹ | R² | R³ | R⁴ | R⁶ | A = | L¹ | L² | L³ | X |
|---|---|---|---|---|---|---|---|---|---|---|
| BS | tert-butyl | CH₂-cyclopropyl | H | H | CH₃ | phenyl (1,3) | CO₂ | SO₂ | SO₂ | Cl |
| BT | 2-fluorophenyl | CH₃ | H | H | CF₃ | phenyl (1,3) | SO₂ | SO₂ | C=O | Cl |
| BU | tert-butyl | CH₂-cyclopropyl | H | H | CF₃ | phenyl (1,3) | CO₂ | SO₂ | SO₂ | Cl |
| BV | tert-butyl | OH | H | H | CH₃ | phenyl (1,3) | CO₂ | SO₂ | SO₂ | Cl |
| BW | 2-fluorophenyl | F | H | H | CF₃ | phenyl (1,3) | SO₂ | SO₂ | C=O | Cl |
| BX | tert-butyl | $C_3H_7$ | H | H | CF₃ | phenyl (1,3) | CO₂ | SO₂ | SO₂ | Cl |
| BY | 2-(trifluoromethoxy)phenyl | F | H | H | CF₃ | phenyl (1,3) | SO₂ | SO₂ | SO₂ | Cl |
| BZ | tert-butyl | cyclopropyl | H | H | CF₃ | phenyl (1,3) | CO₂ | SO₂ | SO₂ | Cl |
| CA | 2,3-difluorophenyl | H | H | H | CF₃ | phenyl (1,3) | SO₂ | SO₂ | C=O | Cl |
| CB | 2-fluorophenyl | H | H | H | CF₃ | phenyl | SO₂ | SO₂ | SO₂ | H |

-continued
| Cmp | R¹ | R² | R³ | R⁴ | R⁶ | A = | L¹ | L² | L³ | X |
|---|---|---|---|---|---|---|---|---|---|---|
| CC |  | H | H | H | CF₃ | 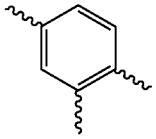 | SO₂ | SO₂ | SO₂ | Cl |
| CD | 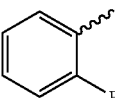 | H | H | H | CF₃ | 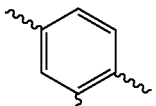 | SO₂ | SO₂ | C=O | Cl |
| CE | 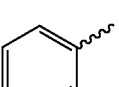 | H | H | H | CF₃ | 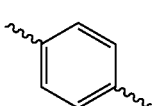 | SO₂ | SO₂ | C=O | OCF₂H |
| CF |  | H | H | H | CH₃ | 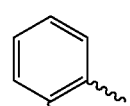 | SO₂ | SO₂ | SO₂ | H |
| CG |  | H | H | H | CF₃ | 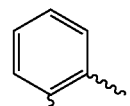 | SO₂ | SO₂ | C=O | H |
| CH |  | H | H | H | CF₃ | 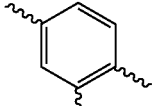 | SO₂ | SO₂ | C=O | OCH₃ |
| CI |  | H | H | H | C₂H₅ | 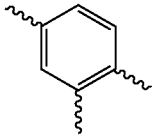 | SO₂ | SO₂ | SO₂ | OCF₃ |
| CJ | 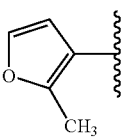 | H | H | H | CH₃ | 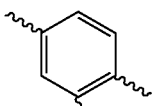 | SO₂ | SO₂ | SO₂ | OCF₃ |
| CK | 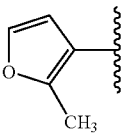 | H | H | H | CF₃ | 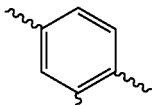 | SO₂ | SO₂ | SO₂ | OCF₃ |
| CL |  | H | H | H | CF₃ | 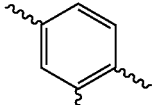 | SO₂ | SO₂ | C=O | OCF₃ |

-continued
| Cmp | R¹ | R² | R³ | R⁴ | R⁶ | A = | L¹ | L² | L³ | X |
|---|---|---|---|---|---|---|---|---|---|---|
| CM | 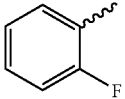 | H | H | H | CF₃ | 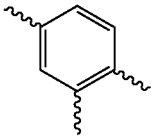 | SO₂ | SO₂ | C=O | CF₃ |
| CN | 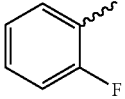 | H | H | H | CF₃ | 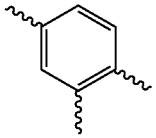 | SO₂ | SO₂ | C=O | OCF₃ |
| CO | 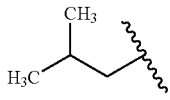 | H | H | H | CH₃ | 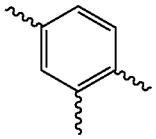 | SO₂ | SO₂ | SO₂ | Cl |
| CP | C₄H₉ | H | H | H | CH₃ | 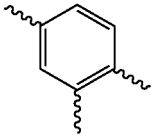 | SO₂ | SO₂ | SO₂ | Cl |
| CQ | 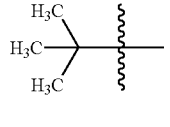 | H | H | H | C₂H₅ | 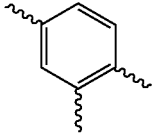 | CO₂ | SO₂ | SO₂ | Cl |
| CR | CH₃ | H | H | H | CF₃ | 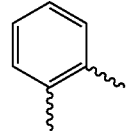 | CO₂ | SO₂ | C=O | H |
| CS | 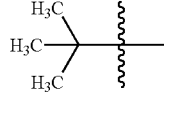 | H | H | H | CF₃ | 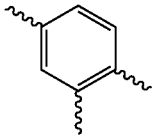 | CO₂ | SO₂ | SO₂ | CF₃ |
| CX | 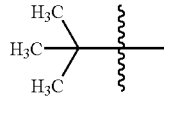 | F | H | H | CF₃ | 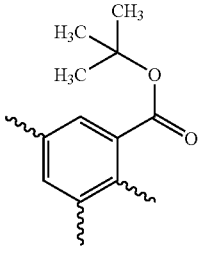 | CO₂ | SO₂ | C=O | Cl |
| DA | 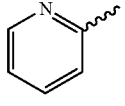 | F | H | H | CF₃ | 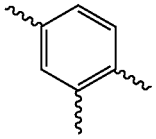 | SO | SO₂ | SO₂ | Cl |

-continued

| Cmp | R¹ | R² | R³ | R⁴ | R⁶ | A = | L¹ | L² | L³ | X |
|---|---|---|---|---|---|---|---|---|---|---|
| DB | 2-(OCF₃)-phenyl | F | H | H | CF₃ | phenyl | SO | SO₂ | SO₂ | Cl |
| DG | tert-butyl | H | H | H | N(CH₃)₂ | phenyl | CO₂ | SO₂ | SO₂ | Cl |
| DK | 2-pyridyl | OCH₃ | H | H | CF₃ | phenyl | SO₂ | SO₂ | SO₂ | Cl |
| DM | 2-F-phenyl | OCH₃ | H | H | CH₃ | phenyl | SO₂ | SO₂ | SO₂ | Cl |
| DN | 2-pyrimidinyl | F | H | H | CF₃ | phenyl | SO | SO₂ | SO₂ | Cl |
| DO | 2-F-phenyl | OC₂H₅ | H | H | CF₃ | phenyl | SO₂ | SO₂ | SO₂ | Cl |
| DP | 1-(2-pyridyl)ethyl | OCH₃ | H | H | CH₃ | phenyl | SO₂ | SO₂ | SO₂ | Cl |
| DQ | 4-(OCF₃)-phenyl | F | H | H | CF₃ | phenyl | SO₂ | SO₂ | SO₂ | Cl |
| DR | piperidin-1-yl | F | H | H | CF₃ | phenyl | SO₂ | SO₂ | SO₂ | Cl |
| DS | N-methyl-tert-butylamino | F | H | H | CF₃ | phenyl | SO₂ | SO₂ | SO₂ | Cl |

-continued

| Cmp | R¹ | R² | R³ | R⁴ | R⁶ | A = | L¹ | L² | L³ | X |
|---|---|---|---|---|---|---|---|---|---|---|
| DT | CH₃ | H | H | H | CH₃ | 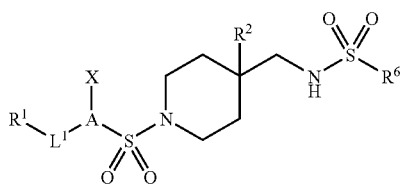 | SO₂ | SO₂ | SO₂ | Cl |

CB = covalent bond
*R³ and R⁴ taken together form a carbonyl group (C=O).

8. The compound according to claim 1 having the formula:

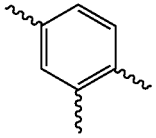

or a pharmaceutically acceptable salt thereof, wherein R¹, R², R⁶, A, L¹, and X are as set forth in the following table:

| Cmp. | R¹ | R² | R⁶ | A | L¹ | X |
|---|---|---|---|---|---|---|
| A | (CH₃)₃C-CH< | H | CF₃ | phenyl | CO₂ | Cl |
| C | (CF₃)(CH₃)₂C- | H | CF₃ | phenyl | CO₂ | Cl |
| D | (CH₃)₃C- | H | CF₃ | phenyl | CO₂ | H |
| E | (CH₃)₃C- | H | CF₃ | phenyl | CO₂ | Cl |
| F | (CH₃)₃C- | H | CH₃ | phenyl | CO₂ | Cl |
| G | cyclobutyl-CH₂- | H | CF₃ | phenyl | CO₂ | Cl |
| H | i-propyl | H | CF₃ | phenyl | CO₂ | Cl |
| J | 2-F-phenyl | H | CH₃ | phenyl | SO₂ | OCH₃ |
| L | 2-F-phenyl | H | CH₃ | phenyl | SO₂ | OCF₂H |
| M | 2-F-phenyl | H | CH₃ | phenyl | SO₂ | OCF₃ |
| N | 2-F-phenyl | H | C₂H₅ | phenyl | SO₂ | OCF₂H |
| Q | 2-F-phenyl | H | CF₃ | phenyl | SO₂ | CF₃ |
| AK | (CH₃)₃C- | OCH₃ | CH₃ | phenyl | CO₂ | Cl |
| AL | 2-F-phenyl | CH₃ | CF₃ | phenyl | SO₂ | Cl |
| AM | 2-F-phenyl | CH₃ | CH₃ | phenyl | SO₂ | Cl |
| AN | (CH₃)₃C- | CH₃ | CF₃ | phenyl | CO₂ | Cl |
| AP | 2-F-phenyl | H | CF₃ | phenyl | CO₂ | OCH₃ |

-continued

| Cmp. | R¹ | R² | R⁶ | A | L¹ | X |
|---|---|---|---|---|---|---|
| AQ | 2-F-phenyl | F | CF₃ | phenyl | SO₂ | Cl |
| AR | tert-butyl | F | CF₃ | phenyl | CO₂ | Cl |
| AS | pyridin-2-yl | F | CF₃ | phenyl | SO₂ | Cl |
| AU | 2,6-difluorophenyl | F | CF₃ | phenyl | SO₂ | Cl |
| AV | 2-F-phenyl | OCH₃ | CF₃ | phenyl | SO₂ | Cl |
| AW | 2-F-phenyl | OCH₃ | CF₃ | phenyl | SO | Cl |
| AX | tert-butyl | OCH₃ | CF₃ | phenyl | CO₂ | Cl |
| AZ | 2-F-phenyl | H | CF₃ | phenyl | SO₂ | OCF₃ |
| BD | tert-butyl | H | CF₃ | phenyl | CO₂ | OCF₃ |
| BE | (CF₃)₂C(CH₃)- | H | CF₃ | phenyl | CO₂ | Cl |
| DK | pyridin-2-yl | OCH₃ | CF₃ | phenyl | SO₂ | Cl |
| DM | 2-F-phenyl | OCH₃ | CH₃ | phenyl | SO₂ | Cl |
| DO | 2-F-phenyl | OC₂H₅ | CF₃ | phenyl | SO₂ | Cl |
| DP | pyridin-2-yl | OCH₃ | CH₃ | phenyl | SO₂ | Cl |

CB = covalent bond
* R³ and R⁴ taken together form a carbonyl group (C=O).

9. The compound according to claim 1 having the formula:

10. The compound according to claim 1 having the formula:

11. The compound according to claim 1 having the formula:

12. The compound according to claim 1 having the formula:

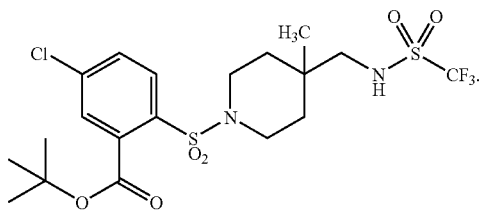

13. The compound according to claim 1 having the formula:

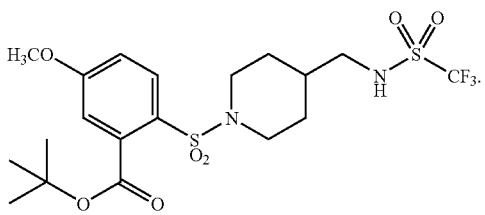

14. The compound according to claim 1 having the formula:

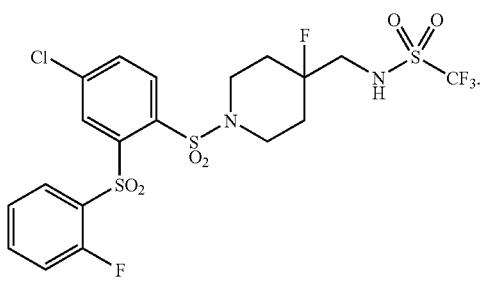

15. The compound according to claim 1 having the formula:

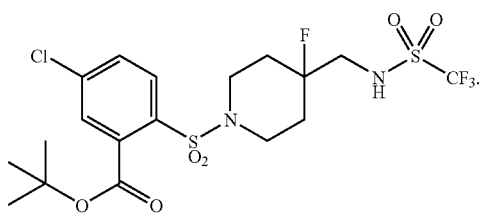

16. The compound according to claim 1 having the formula:

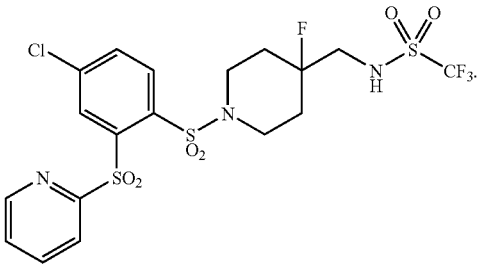

17. The compound according to claim 1 having the formula:

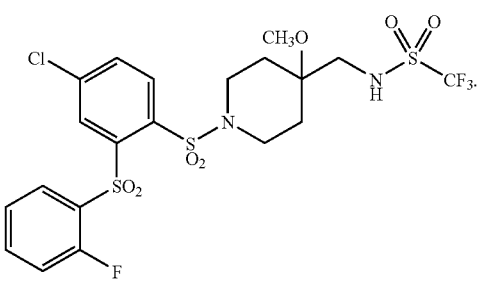

18. The compound according to claim 1 having the formula:

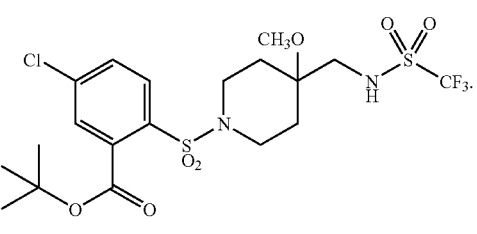

19. The compound according to claim 1 having the formula:

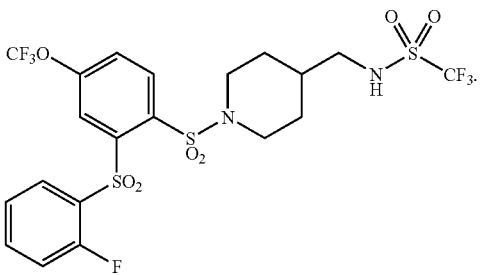

20. The compound according to claim 1 having the formula:

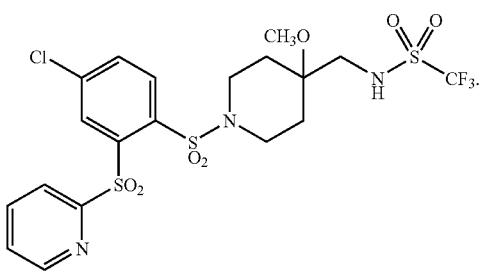

21. The compound according to claim 1 having the formula:

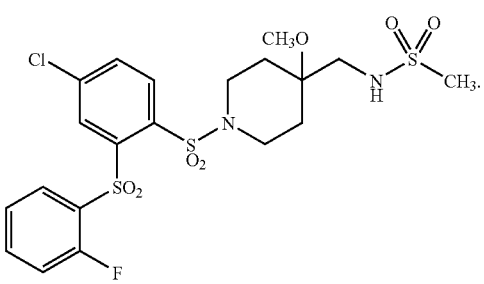

22. A pharmaceutical composition comprising an effective amount of a compound according to claim 1 and a pharmaceutically acceptable carrier.

23. A pharmaceutical composition comprising an effective amount of a compound according to claim 9 and a pharmaceutically acceptable carrier.

24. A pharmaceutical composition comprising an effective amount of a compound according to claim 10 and a pharmaceutically acceptable carrier.

25. A method of inflammatory diseases comprising administering to a mammal in need of such treatment an effective amount of a compound according to claim 1.

26. A method of treating allergy, seasonal allergic rhinitis, reversible airway obstruction, adult respiratory distress syndrome, asthma, or bronchitis comprising administering to a mammal in need of such treatment an effective amount of a compound according to claim 1.

27. The method of claim 25 wherein the condition or disease treated is seasonal allergic rhinitis.

28. The method of claim 25 wherein the condition or disease treated is asthma.

29. The method of claim 25 wherein the condition or disease treated is bronchitis.

30. A process for making a pharmaceutical composition comprising combining a compound of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,645,774 B2 | Page 1 of 1 |
| APPLICATION NO. | : 11/197979 | |
| DATED | : January 12, 2010 | |
| INVENTOR(S) | : Richard J. Friary et al. | |

It is certified that error appears in the above-identified patent and that said Letters Patent is hereby corrected as shown below:

On the Title page,

[*] Notice:   Subject to any disclaimer, the term of this patent is extended or adjusted under 35 U.S.C. 154(b) by 506 days.

Delete the phrase "by 506 days" and insert -- by 1030 days --

Signed and Sealed this

Twenty-fourth Day of August, 2010

David J. Kappos
*Director of the United States Patent and Trademark Office*